(12) United States Patent
Gilchrest et al.

(10) Patent No.: US 7,033,829 B2
(45) Date of Patent: *Apr. 25, 2006

(54) METHOD TO INHIBIT CELL GROWTH USING OLIGONUCLEOTIDES

(75) Inventors: Barbara A. Gilchrest, Boston, MA (US); Mark S. Eller, Boston, MA (US); Mina Yaar, Sharon, MA (US)

(73) Assignee: Trustees of Boston University, Boston, MA (US)

( * ) Notice: Subject to any disclaimer, the term of this patent is extended or adjusted under 35 U.S.C. 154(b) by 424 days.

This patent is subject to a terminal disclaimer.

(21) Appl. No.: 10/122,633

(22) Filed: Apr. 12, 2002

(65) Prior Publication Data

US 2003/0032611 A1   Feb. 13, 2003

Related U.S. Application Data

(63) Continuation-in-part of application No. PCT/US01/10162, filed on Mar. 30, 2001, which is a continuation-in-part of application No. 09/540,843, filed on Mar. 31, 2000.

(51) Int. Cl.
C12Q 3/00         (2006.01)

(52) U.S. Cl. .................. 435/375; 435/6; 435/325; 435/377; 514/44; 536/23.1; 536/24.5

(58) Field of Classification Search .............. 536/23.1, 536/24.5
See application file for complete search history.

(56) References Cited

U.S. PATENT DOCUMENTS

| | | | |
|---|---|---|---|
| 3,937,809 A | 2/1976 | Jacobi | |
| 4,419,343 A | 12/1983 | Pauly | |
| 4,508,703 A | 4/1985 | Redziniak et al. | |
| 4,621,023 A | 11/1986 | Redziniak et al. | |
| 5,077,211 A | 12/1991 | Yarosh | |
| 5,455,029 A | 10/1995 | Hartman et al. | |
| 5,470,577 A | 11/1995 | Gilchrest et al. | |
| 5,489,508 A | 2/1996 | West et al. | |
| 5,532,001 A | 7/1996 | Gilchrest et al. | |
| 5,580,547 A | 12/1996 | Gilchrest et al. | |
| 5,599,672 A | 2/1997 | Liang et al. | |
| 5,643,556 A | 7/1997 | Gilchrest et al. | |
| 5,643,890 A | 7/1997 | Iversen et al. | |
| 5,645,986 A | 7/1997 | West et al. | |
| 5,837,857 A | 11/1998 | Villaponteau et al. | |
| 5,858,987 A | 1/1999 | Beer-Romero et al. | |
| 5,879,713 A | 3/1999 | Roth et al. | |
| 6,007,989 A | 12/1999 | West et al. | |
| 6,015,710 A | 1/2000 | Shay et al. | |
| 6,046,307 A | 4/2000 | Shay et al. | |
| 6,147,056 A * | 11/2000 | Gilchrest et al. | ............. 514/44 |
| 6,194,206 B1 | 2/2001 | West et al. | |
| 6,320,039 B1 | 11/2001 | Villeponteau et al. | |
| 6,440,650 B1 | 8/2002 | Matsuda et al. | |

FOREIGN PATENT DOCUMENTS

| EP | 0 035 384 A1 | 9/1981 |
|---|---|---|
| WO | WO 93/09788 | 5/1993 |
| WO | WO 93/22431 | 11/1993 |
| WO | WO 95/01773 | 1/1995 |
| WO | WO 95/07362 | 3/1995 |
| WO | WO 95/09175 | 4/1995 |
| WO | WO 96/23508 | 8/1996 |
| WO | WO 97/08314 | 8/1996 |
| WO | WO 96/40989 | 12/1996 |
| WO | WO 97/44450 | 11/1997 |
| WO | WO 98/36066 | 12/1998 |
| WO | WO 99 03507 | 1/1999 |
| WO | WO 01/18015 | 3/2001 |

OTHER PUBLICATIONS

U.S. Appl. No. 10/122,630.*
U.S. Appl. No. 09/540,843.*
Akiyama, M., et al., "Cytostatic Concentrations of Anticancer Agents do not Affect Telomerase Activity of Leukaemic Cells In Vitro", *Eur. J. Cancer*, 35 (2):309-315 (1999).
Balasubramanian, S. et al., "Activation of telomerase and its association with G1-phase of the cell cycle during UVB-induced skin tumorigenesis in SKH-1 hairless mouse," *Oncogene*, 18:1297-1302 (1999).
Beltz, L. et al., "The Effects of Telomerase Inhibitors on Lymphocyte Function,", *Anticancer Research*, 19:3205-3212 (1999).

(Continued)

*Primary Examiner*—J. D. Schultz
(74) *Attorney, Agent, or Firm*—Howrey LLP; David W. Clough

(57) ABSTRACT

Described are methods for treating hyperproliferative disorders, including cancers, by administering to the affected mammal (e.g., human) an effective amount of a composition comprising pTT or a composition comprising one or more oligonucleotides which share at least 50% nucleotide sequence identity with the human telomere overhang repeat. Methods of treatment or prevention of hyperproliferative diseases or pre-cancerous conditions affecting epithelial cells, such as psoriasis, atopic dermatitis, or hyperproliferative or UV-responsive dermatoses, hyperproliferative diseases of other epithelia and methods for reducing photoaging, or oxidative stress or for prophylaxis against or reduction in the likelihood of the development of skin cancer, are also disclosed.

10 Claims, 34 Drawing Sheets

OTHER PUBLICATIONS

Cruz, P.D., Jr., et al, "Thymidine Dinucleotides Inhibit Contact Hypersensitivity and Activate the Gene for Tumor Necrosis Factor α," *J. Investigative Dermatology*, 114:253-258 (2000).

de Vries, T. J., et al, "Expression of gp100, MART-1, Tyrosinase and S100 in Paraffin-Embedded Primary Melanomas and Locoregional, Lymph Node, and Visceral Metastases: Implications for Diagnosis and Immunotherapy. A study conducted by the EORTC Melanoma Cooperative Group," *J. Pathology*, 193:13-20 (2001).

El-Deiry, W.S., et al., "WAF1, a Potential Mediator of p53 Tumor Suppression,", *Cell*, 75:817-825 (1993).

Eller, M. S., et al., "The Effects of Oligonucleotide Size and 500l' Phosphate on Stimulation of Melanogenesis", *Journal of Investigative Dermatology*, Abstract No. 113, vol. 112, No. 4, p. 542 (1999).

Eller, M.S., et al., "Enhancement of DNA Repair in Human Skin Cells by Thymidine Dinucleotides: Evidence for a p53-Mediated Mammalian SOS Response", Proc. Natl. Acad. Sci. USA, 94:12627-12632 (1997).

Fritsche, M. et al., "Induction of nuclear accumulation of the tumor-suppressor protein p53 by DNA-damaging agents," *Oncogene* 8:307-318 (1993).

Hadshiew, I.M., et al., "Stimulation of Melanogenesis by DNA Oligonucleotides: Effect of Size, Sequences and 5' Phosphorylation," *Journal of Dermatological Science*, 127-138 (2001).

Harley, C. B., et al., "Telomerase, Checkpoints and Cancer," In Cancer Surveys—Advances and Prospects in Clinical, Epidemiological and Laboratory Oncology, Cold Spring Harbor Laboratory Press, 29:263-284 (1997).

Hupp, T. R., et al., "Small Peptides Activate the Latent Sequence-Specific DNA Binding Function of p53,", *Cell*, 83:237-245 (1995).

Jayaraman, L. et al., "Activation of p53 Sequence-Specific DNA Binding by Short Single Strands of DNA Requires the p53 C-terminus," *Cell*, 81:1021-1029 (1995).

Kastan, M. B., et al., "A Mammalian Cell Cycle Checkpoint Pathway Utilizing p53 and GADD45 Is Defective in Ataxia-Telangiectasia," *Cell*, 71:587-597 (1992).

Kern, S. E., et al., "Oncogenic Forms of p53 Inhibit p53-Regulated Gene Expression", *Science*, 256:827-830 (1992).

Lu, X. et al., "Differential Induction of Transcriptional Active p53 Following UV or Ionizing Radiation: Defects in Chromosome Instability Syndromes?", *Cell*, 75:765-778 (1993).

Mata, J., et al., "A Hexameric Phosphorothioate Oligonucleotide Telomerase Inhibitor Arrests Growth of Burkitt's Lymphoma Cells *in Vitro* and *in Vivo,"* *Toxicol. Appl. Pharmacol.*, 144:189-197 (1997).

Mitchell, D. L., et al., "The Induction and Repair of DNA Photodamage in the Environment", In *Environment UV Photobiology*, A.R. Young et al., eds. (NY:Plenum Press), pp. 345-377 (1993).

Mitsudomi, T., et al., "p53 gene mutations in non-small-cell lung cancer cell lines and their correlation with the presence of *ras* mutations and clinical features,", *Oncogene* 7:171-180 (1992).

Nelson, W. G., et al., "DNA Strand Breaks: the DNA Template Alterations That Trigger p53-Dependent DNA Damage Response Pathways," *Mol. and Cell Biol*, 14(3):1815-1823 (1994).

Nicolaus, B. J. R., "Symbiotic Approach to Drug Design", *Decision Making in Drug Research*, 173-186 (1983).

Niggli, H. J., et al., "Sunlight-Induced Pyrimidine Dimers in Human Skin Fibroblasts in Comparison with Dimerization After Artificial UV-Irradiation," *Photochemistry and Photobiology*, 48(3):353-356 (1988).

Norton, J. C. et al., "Inhibition of Human Telomerase Activity by Peptide Nucleic Acids," *Nature Biotechnology*, 14:615-619 (1996).

Ohnuma, T., et al., "Inhibitory Effects of Telomere-Mimic Phosphorothiote Oligonucleotides on Various Human Tumor Cells *in Vitro,"*, *Anticancer Research*, 17:2455-2458 (1997).

Page, T. J., et al., "The Cytotoxic Effects of Single-Stranded Telomere Mimics on 0MA-BL1 Cells," *Experimental Cell Research*, 252:41-49 (1999).

Parris, C. N., et al., "Telomerase activity in melanoma and non-melanoma skin cancer", *British J. of Cancer*, 79 (1):47-53 (1999).

Pedeux, R., et al., "Thymidine Dinucleotides Induce S Phase Cell Cycle Arrest in Addition to Increased Melanogenesis in Human Melanocytes", *J. of Investigative Dermatology*, 111:472-477 (1998).

Saeki, T., et al., "Inhibitory Effect of Telomere-Mimic Phosphorothioate Oligodeoxy Nucleotides (S-ODNS) in Human Tumor Cell Lines," *Onocology*, 57:27-36 (1999).

Sanchez, Y., et al., "Regulation of RAD53 by the ATM-Like Kinases MEC1 and TEL1 in Yeast Cell Cycle Checkpoint Pathways," *Science*, 271:357-360 (1996).

Saretzki, G., et al., "Telomere Shortening Triggers a p53-Dependent Cell Cycle Arrest Via Accumulation of G-Rich Single Stranded DNA Fragments," *Oncogene*, 18:5148-5158 (1999).

Walworth, N.C., et al., "rad-Dependent Response of the chk1-Encoded Protein Kinase at the DNA Damage Checkpoint," *Science*, 271:353-356 (1996).

Wei, Q., et al., "DNA repair and aging in basal cell carcinoma: A molecular epidemiology study," *Proc. Natl. Acad. Sci. USA*, 90:1614-1618. (1993).

Wright, W. E., et al., "Experimental elongation of telomeres extends the lifespan of immortal x normal cell hybrids," *The EMBO Journal*, 15(7):1734-1741 (1996).

Wu, K., et al., "Telomerase Activity and Telomere Length in Lymphocytes from Patients with Cutaneous T-Cell Lymphoma," *Cancer*, 86(6):1056-1063 (1999).

Yaar, M., et al., "The trk Family of Receptors Mediates Nerve Growth Factor and Neurotrophin-3 Effects in Melanocytes," *J. Clin. Invest*, 94:1550-1562 (1994).

Yaar, M., et al., "Aging Versus Photoaging: Postulated Mechanisms and Effectors," *The Society for Investigative Dermatology Symposium Proceedings*, 3:47-51 (1998).

* cited by examiner

Fig. 19A     Fig. 19B     Fig. 19C     Fig. 19D
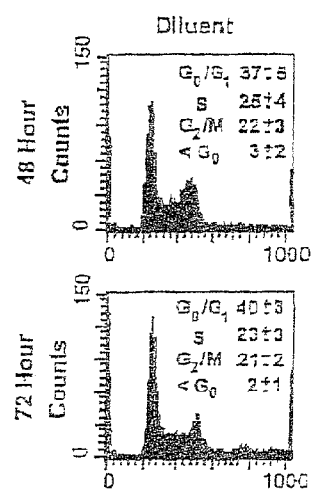
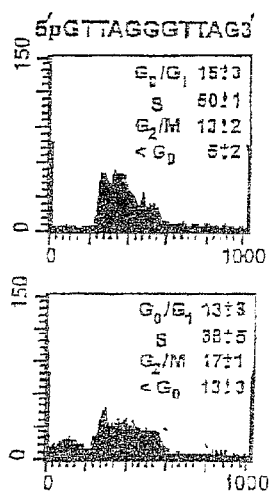
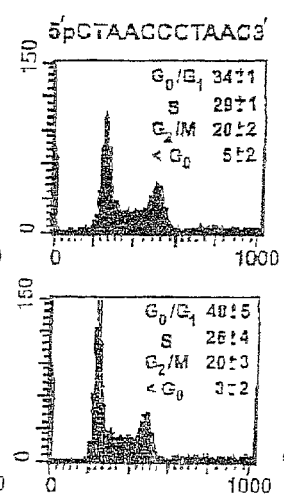
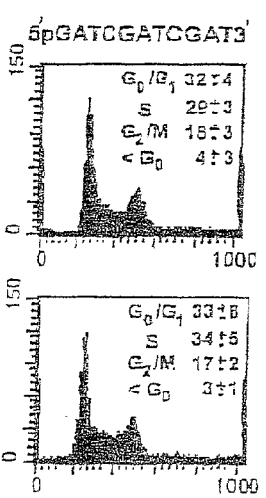
Fig. 19E     Fig. 19F     Fig. 19G     Fig. 19H

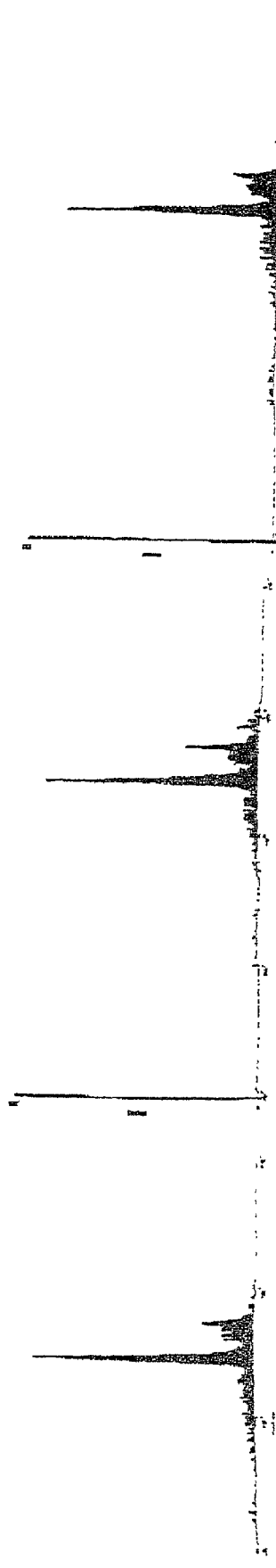

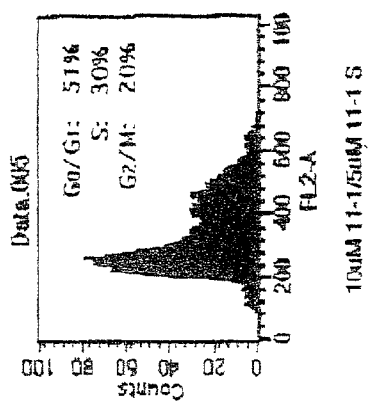
Fig. 21A
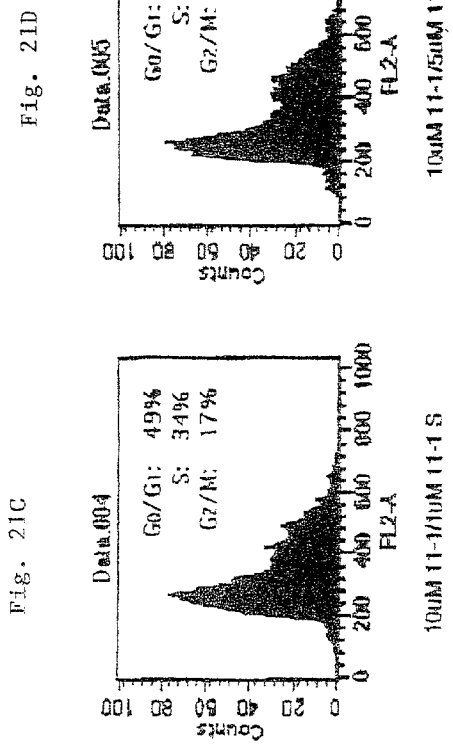
Fig. 21B
Fig. 21C
Fig. 21D
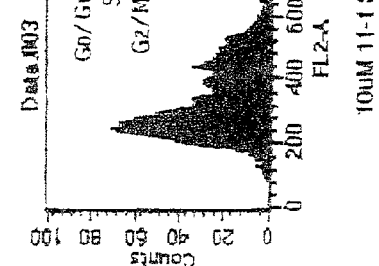
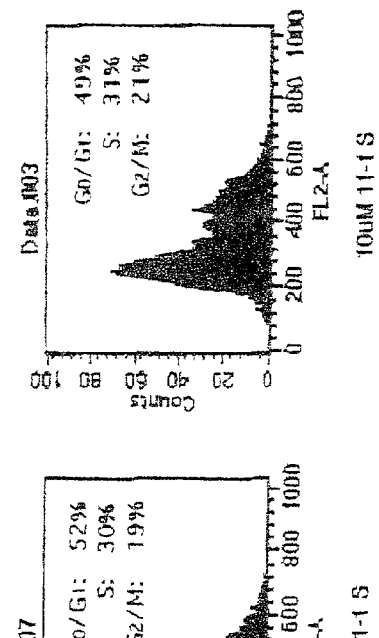
Fig. 21E
Fig. 21F
Fig. 21G

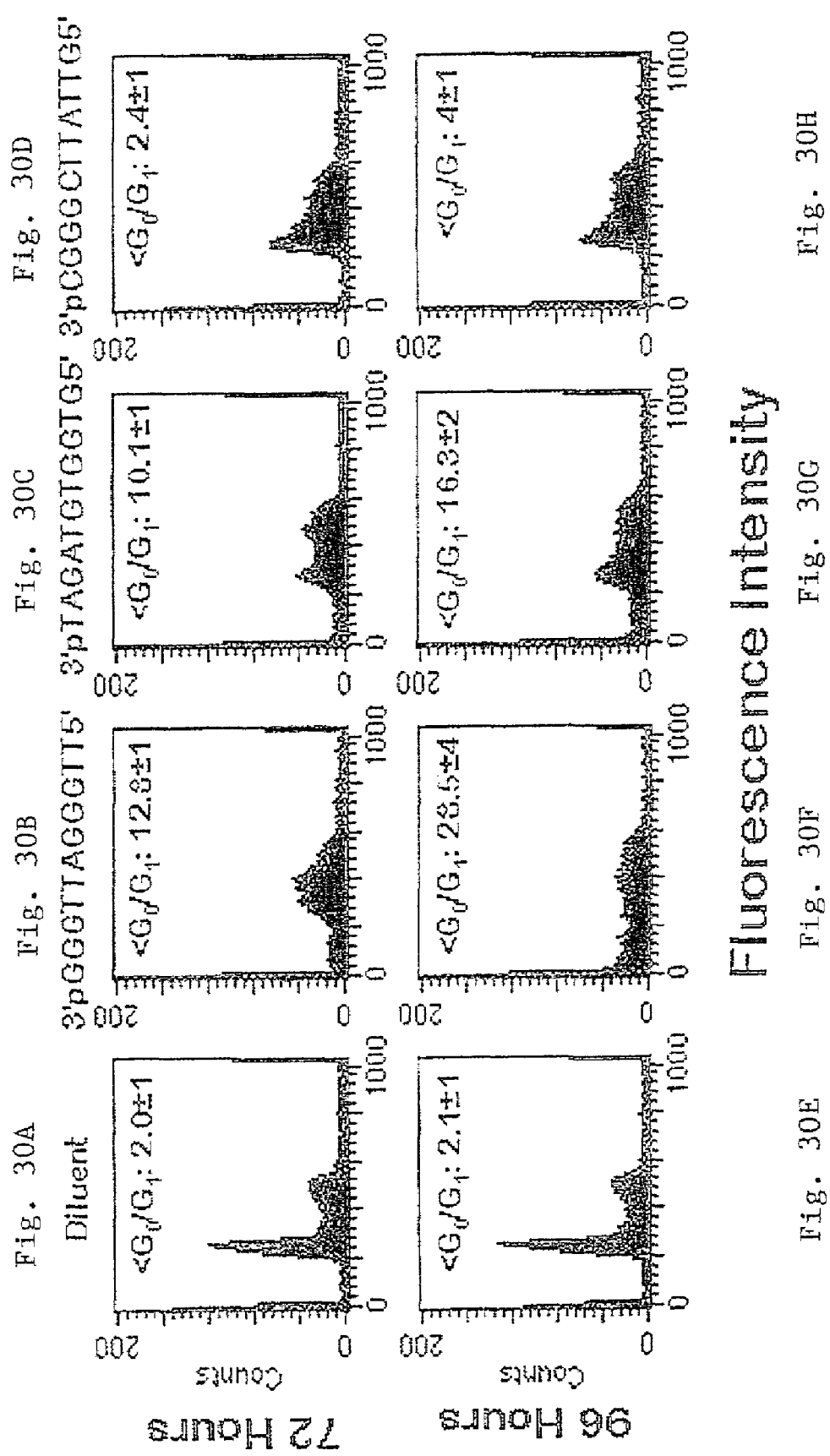

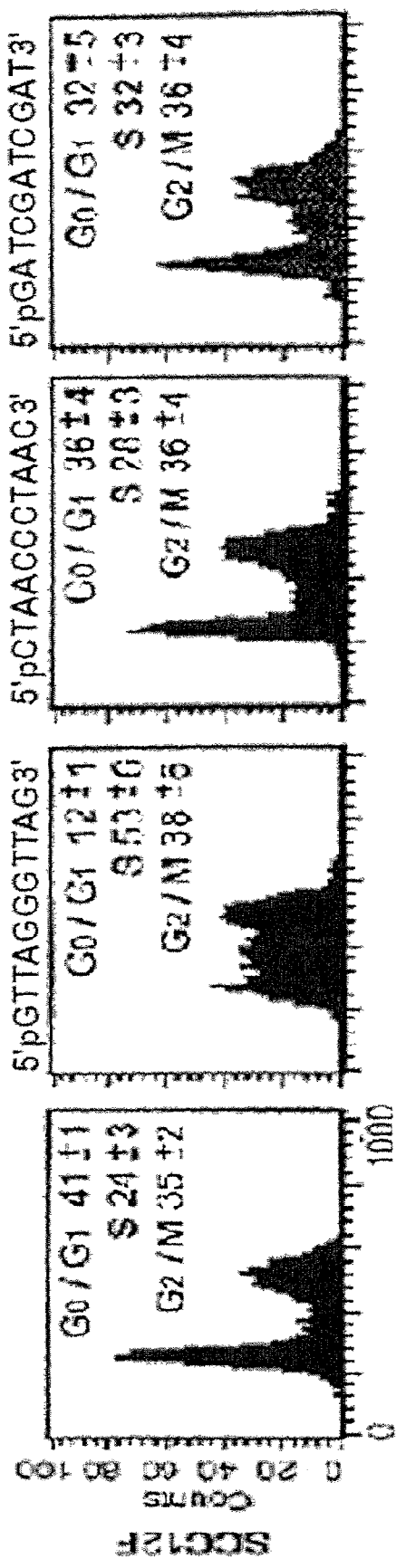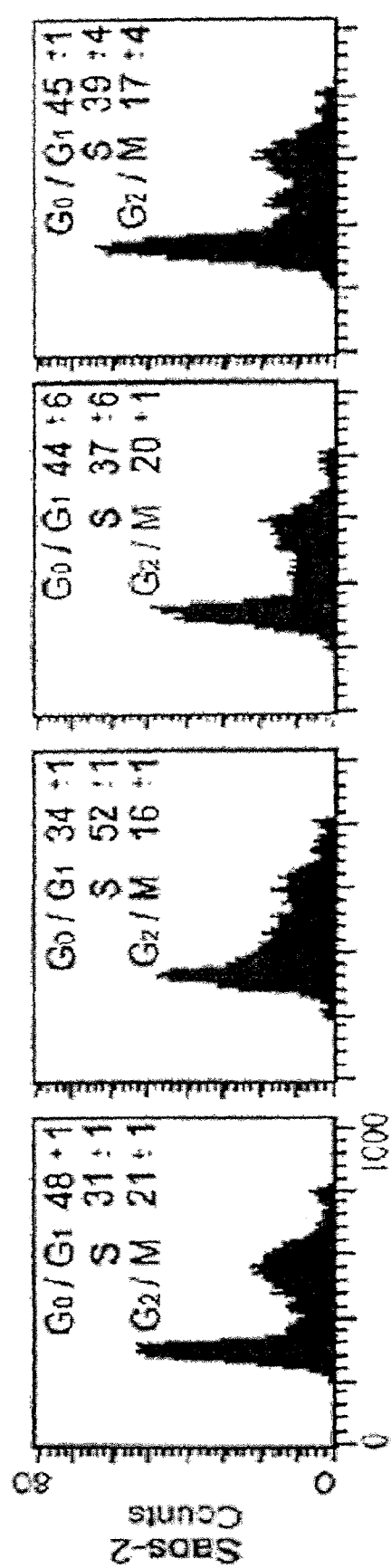
Fig. 33A Fig. 33B Fig. 33C Fig. 33D Fig. 33E Fig. 33F Fig. 33G Fig. 33H

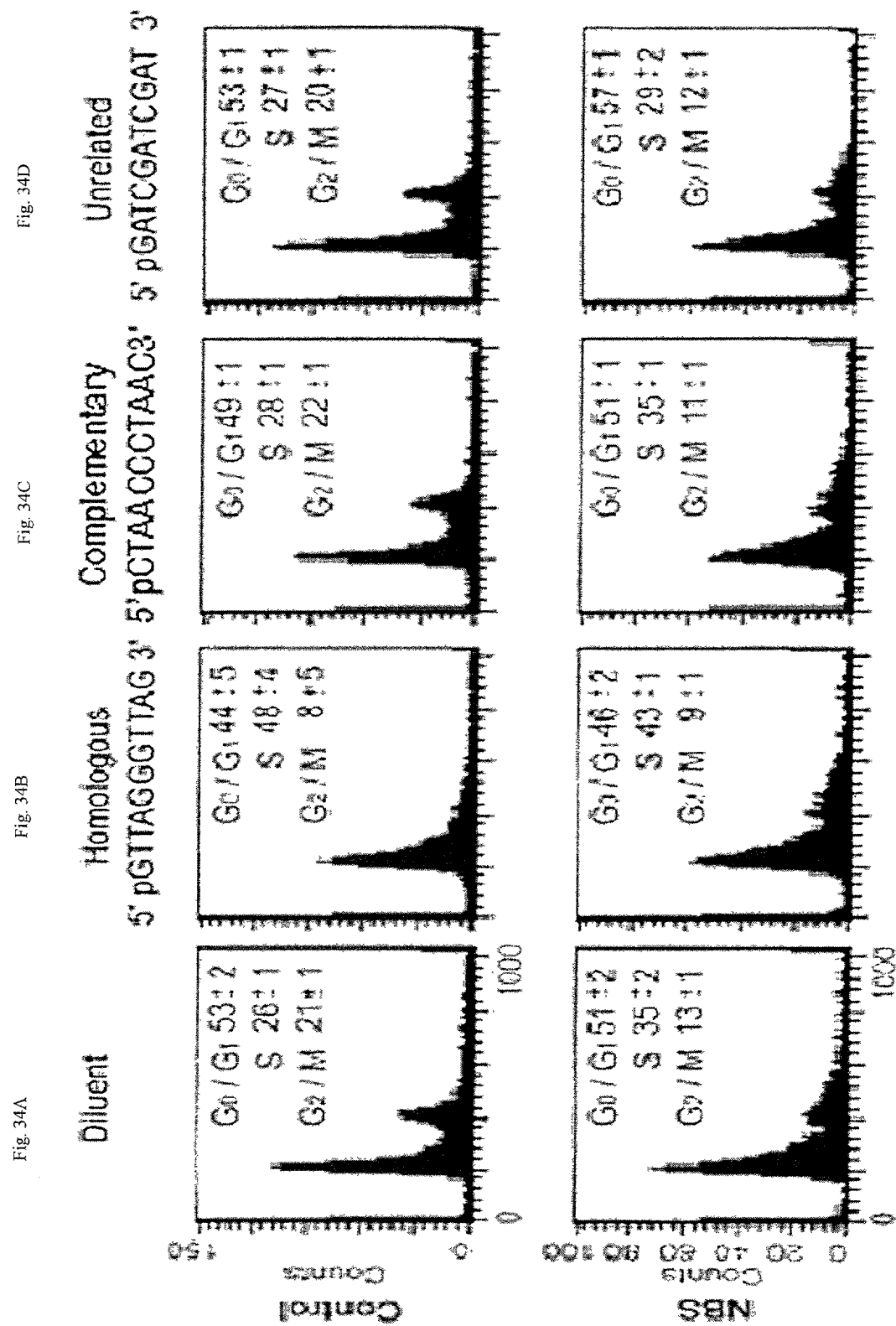

SEQUENCE LISTING

<160> NUMBER OF SEQ ID NOS: 15

<210> SEQ ID NO 1
<211> LENGTH: 9
<212> TYPE: DNA
<213> ORGANISM: Artificial Sequence

```
<220> FEATURE:
<223> OTHER INFORMATION: Synthetic DNA Fragment

<400> SEQUENCE: 1 gagtatgag                                                                 9

<210> SEQ ID NO 2
<211> LENGTH: 9
<212> TYPE: DNA
<213> ORGANISM: Artificial Sequence
<220> FEATURE:
<223> OTHER INFORMATION: Synthetic DNA Fragment

<400> SEQUENCE: 2 taggaggat                                                                 9

<210> SEQ ID NO 3
<211> LENGTH: 7
<212> TYPE: DNA
<213> ORGANISM: Artificial Sequence
<220> FEATURE:
<223> OTHER INFORMATION: Synthetic DNA Fragment

<400> SEQUENCE: 3 agtatga                                                                   7

<210> SEQ ID NO 4
<211> LENGTH: 5
<212> TYPE: DNA
<213> ORGANISM: Artificial Sequence
<220> FEATURE:
<223> OTHER INFORMATION: Synthetic DNA Fragment

<400> SEQUENCE: 4 gtatg                                                                     5

<210> SEQ ID NO 5
<211> LENGTH: 11
<212> TYPE: DNA
<213> ORGANISM: Artificial Sequence
<220> FEATURE:
<223> OTHER INFORMATION: Synthetic DNA Fragment

<400> SEQUENCE: 5
gttagggtta g                                                             11

<210> SEQ ID NO 6
<211> LENGTH: 5
<212> TYPE: DNA
<213> ORGANISM: Artificial Sequence
<220> FEATURE:
<223> OTHER INFORMATION: Synthetic DNA Fragment

<400> SEQUENCE: 6 catac                                                                     5

<210> SEQ ID NO 7
<211> LENGTH: 7
<212> TYPE: DNA
<213> ORGANISM: Artificial Sequence
<220> FEATURE:
<223> OTHER INFORMATION: Synthetic DNA Fragment

<400> SEQUENCE: 7 agtatga                                                                   7
```

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA Fragment

<400> SEQUENCE: 8
gcatgcatgc attacgtacg                                           20

<210> SEQ ID NO 9
<211> LENGTH: 11
<212> TYPE: DNA
<213> ORGANISM: Artificial Sequence
<220> FEATURE:
<223> OTHER INFORMATION: Synthetic DNA Fragment

<400> SEQUENCE: 9
ctaaccctaa c                                                    11

<210> SEQ ID NO 10
<211> LENGTH: 11
<212> TYPE: DNA
<213> ORGANISM: Artificial Sequence
<220> FEATURE:
<223> OTHER INFORMATION: Synthetic DNA Fragment

<400> SEQUENCE: 10
gatcgatcga t                                                    11

<210> SEQ ID NO 11
<211> LENGTH: 6
<212> TYPE: DNA
<213> ORGANISM: Artificial Sequence
<220> FEATURE:
<223> OTHER INFORMATION: Synthetic DNA Fragment

<400> SEQUENCE: 11 ttaggg                                                           6

<210> SEQ ID NO 12
<211> LENGTH: 6
<212> TYPE: DNA
<213> ORGANISM: Artificial Sequence
<220> FEATURE:
<223> OTHER INFORMATION: Synthetic DNA Fragment

<400> SEQUENCE: 12 ccctaa                                                           6

<210> SEQ ID NO 13
<211> LENGTH: 10
<212> TYPE: DNA
<213> ORGANISM: Artificial Sequence
<220> FEATURE:
<223> OTHER INFORMATION: Synthetic DNA Fragment

<400> SEQUENCE: 13
gggttaggtt                                                      10

<210> SEQ ID NO 14
<211> LENGTH: 11
<212> TYPE: DNA
<213> ORGANISM: Artificial Sequence
<220> FEATURE:
<223> OTHER INFORMATION: Synthetic DNA Fragment

```
<400> SEQUENCE: 14
tagatgtggt g                                                        11

<210> SEQ ID NO 15
<211> LENGTH: 11
<212> TYPE: DNA
<213> ORGANISM: Artificial Sequence
<220> FEATURE:
<223> OTHER INFORMATION: Synthetic DNA Fragment

<400> SEQUENCE: 15
cgggcttatt g                                                        11
```

METHOD TO INHIBIT CELL GROWTH USING OLIGONUCLEOTIDES

RELATED APPLICATIONS

This application is a continuation-in-part of International Application No. PCT/US01/10162, which designated the United States and was filed on Mar. 30, 2001, published in English, which is a continuation-in-part of application Ser. No. 09/540,843 filed Mar. 31, 2000. The entire teachings of the above applications are incorporated herein by reference.

BACKGROUND OF THE INVENTION

Mammalian cells have a complex response to DNA damage, as well as a tightly regulated program of replicative senescence, all suggested to be fundamental defenses against cancer [Campisi, J. (1996). Cell 84, 497–500]. In mammals, cell senescence is precipitated by critical shortening of telomeres, tandem repeats of the DNA sequence TTAGGG that cap the ends of chromosomes [Greider, C. W. (1996) Annu Rev Biochem 65, 337–365] and become shorter with each round of DNA replication. In germline cells and most cancer cells, immortality is associated with maintenance of telomere length by telomerase, an enzyme complex that adds TTAGGG repeats dues to the 3' terminus at the chromosome ends [Feng, J., et al. Science 269, 1236–1241; Harrington, L., et al., (1997) Science 275, 973–977; Nakamura, T. M., et al., (1997) Science 277, 955–957]. The catalytic subunit of telomerase is generally not expressed in normal somatic cells [Greider, C. W. (1996) Annu Rev Biochem 65, 337–365], and after multiple rounds of cell division critically shortened telomeres trigger either replicative senescence or death by apoptosis, largely dependent on cell type [de Lange, T. (1998) Science 279, 334–335], although the detailed mechanism is unknown. The mechanism by which telomeres participate in DNA damage responses has been less clear.

The frequency of cancer in humans has increased in the developed world as the population has aged. Melanoma and other skin cancers have increased greatly among aging populations with significant accumulated exposure to sunlight. For some types of cancers and stages of disease at diagnosis, morbidity and mortality rates have not improved significantly in recent years in spite of extensive research. Cancers are currently often treated with highly toxic therapies. Alternative therapies are needed that could take advantage of the natural mechanisms of the cells to repair environmental damage.

SUMMARY OF THE INVENTION

One embodiment of the invention is a method for treating a hyperproliferative disorder in a human, the method comprising administering to the human an effective amount of a composition comprising one or more oligonucleotides which share at least 50% nucleotide sequence identity with the human telomere overhang repeat. Herein, where it is said that an oligonucleotide is homologous to the telomere overhang repeat, it is meant that the oligonucleotide shares at least 50% nucleotide sequence identity with the human telomere overhang repeat. In this method, the oligonucleotides can be at least 2 nucleotides long, for example 2–200 nucleotides long, or at least 3 nucleotides long, for example, 3–20 oligonucleotides long, and preferably can be 2–20 nucleotides long, and more preferably are 5–11 nucleotides long. Oligonucleotides having a 5' phosphate group are preferred. Where the 5' phosphate is a part of the oligonucleotide, it is indicated, where the sequence is given, by preceding the 5' to 3' nucleotide sequence with a "p." Preferred oligonucleotides in the treatment of hyperproliferative disorders are pTT, pGAGTATGAG (SEQ ID NO:1), pGTTAGGGTTAG (SEQ ID NO:5), pGGGTTAGGTT (SEQ ID NO:13), and pTAGATGTGGTG (SEQ ID NO:14).

A part of the above method is a method for inhibiting the growth of cancer cells in a human, comprising administering to the human an effective amount of a composition comprising one or more oligonucleotides which share at least 50% nucleotide sequence identity with the human telomere overhang repeat. The cancer cells can be derived from any cell type, but in particular embodiments are lymphoma, osteosarcoma, melanoma, leukemia or carcinomas.

Another part of the invention is a method for promoting differentiation of malignant cells in a mammal, the method comprising administering to the mammal an effective amount of a composition comprising one or more oligonucleotides which share at least 50% nucleotide sequence identity with $(TTAGGG)_n$.

A further method, useful in the treatment of cancers, is a method for enhancing the expression of one or more surface antigens indicative of differentiation of cancer cells in a human, the method comprising administering to the human an effective amount of one or more oligonucleotides which share at least 50% nucleotide sequence identity with the human telomere overhang repeat. The cells in this method can be, for example, melanoma, and the antigen can be, for example, MART-1, tyrosinase, TRP-1 or gp-100. Another oligonucleotide to be used in this method is pTT; a combination of one or more telomere-homologous oligonucleotides and pTT can also be used. pGTTAGGGTTAG (SEQ ID NO:5) is one oligonucleotide applicable in this method.

Further, the invention is a method for inducing apoptosis in cancer cells in a human, said method comprising administering to the human an effective amount of a composition comprising one or more oligonucleotides which share at least 50% nucleotide sequence identity with the human telomere overhang repeat. This method can be applied, for example, to melanoma and lymphoma.

Also a part of the invention is a method for inhibiting the growth of cancer cells in a human, the method being independent of the presence or activity of telomerase in the cancer cells, in which the method includes the step of administering to the human an effective amount of a composition comprising one or more oligonucleotides which share at least 50% nucleotide sequence identity with the human telomere overhang repeat.

A further aspect of the invention is a method to inhibit the growth of cancer cells in a human, the method not requiring the presence or activity of p53 gene product in the cancer cells, the method comprising administering to the human an effective amount of a composition comprising one or more oligonucleotides which share at least 50% nucleotide sequence identity with the human telomere overhang repeat.

A further aspect of the invention is a method to inhibit the growth of cancer cells in a human, the method resulting in S-phase arrest in said cells, the method comprising administering to the human an effective amount of a composition comprising one or more oligonucleotides which share at least 50% nucleotide sequence identity with the human telomere overhang repeat. The oligonucleotide to be used can be various lengths, but in one embodiment the oligonucleotide can be less than 6 nucleotides long.

Herein is also described a method for preventing spongiosis, blistering or dyskeratosis in the skin of a mammal, following exposure to ultraviolet light, the method comprising applying to the skin an effective amount of a composition comprising one or more oligonucleotides which share at least 50% nucleotide sequence identity with the human telomere overhang repeat. The method can employ, for example, pGAGTATGAG (SEQ ID NO:1), or the oligonucleotide pTT, or a combination of oligonucleotides.

Also described herein is a method for reducing the occurrence of skin cancer in a human, the method comprising applying to the skin an effective amount of a composition comprising one or more oligonucleotides which share at least 50% nucleotide sequence identity with the human telomere overhang repeat. Such oligonucleotide can be, for example, pGAGTATGAG (SEQ ID NO:1). pTT can also be used in the method, or a combination of oligonucleotides can be used.

A special aspect of the above methods to reduce the occurrence of skin cancer in a human is a method for reducing the occurrence of skin cancer in a human with xeroderma pigmentosum, or other genetically determined cancer predisposition, the method comprising applying to the skin an effective amount of a composition comprising one or more oligonucleotides which share at least 50% nucleotide sequence identity with the human telomere overhang repeat. In one aspect, the oligonucleotide is pGAGTATGAG (SEQ ID NO:1).

Another particular aspect of the invention is a method for reducing the occurrence of skin cancer in a human with xeroderma pigmentosum or other genetically determined predisposition, the method comprises applying to the skin an effective amount of a composition comprising pTT.

Also included in the invention is a method for enhancing repair of ultraviolet irradiation-induced damage to skin in a human, in which the method includes applying to the skin an effective amount of a composition comprising one or more oligonucleotides which share at least 50% nucleotide sequence identity with the human telomere overhang repeat. A particular oligonucleotide that can be used is pGAGTATGAG (SEQ ID NO:1). Another that can be used in the method is pTT.

Also included as an aspect of the invention is a method for reducing oxidative damage in a mammal, the method comprising administering to the mammal an effective amount of a composition comprising one or more oligonucleotides which share at least 50% nucleotide sequence identity with the human telomere overhang repeat. One such oligonucleotide is pGTTAGGGTTAG (SEQ ID NO:5). pTT can also be used in the method. In a particular aspect of this method, the composition can be administered to the skin.

It is also an object of the invention to provide a method for treating melanoma in a mammal, comprising administering to the mammal an effective amount of a composition comprising one or more oligonucleotides that share at least 50% nucleotide sequence identity with the human telomere overhang repeat. The method is applicable to humans. Oligonucleotides to be used in the method include the telomere-homologous oligonucleotide pGTTAGGGTTAG (SEQ ID NO:5). pTT can also be used. Various combinations of oligonucleotides can also be used in the method.

It is also an object of the invention to provide a method for reducing proliferation of keratinocytes in the skin of a human, the method comprising applying to the skin an effective amount of a composition comprising one or more oligonucleotides that share at least 50% nucleotide sequence identity with the human telomere overhang repeat. In particular applications of the method, the human to be treated has seborrheic keratosis, actinic keratosis, Bowen's disease, squamous cell carcinoma, or basal cell carcinoma. In a particular aspect of the method, the composition comprises pGTTAGGGTTAG (SEQ ID NO:5). A related method is a method for reducing proliferation of keratinocytes in the skin of a human, said method comprising applying to the skin an effective amount of a composition comprising pTT.

Another embodiment comprises increasing DNA repair in epithelial cells, comprising contacting said cells with an effective amount of a composition comprising at least one oligonucleotide, wherein the oligonucleotide comprises a base sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 11, SEQ ID NO: 12, and a contiguous portion of any of the foregoing sequences. Another embodiment comprises inhibiting proliferation of epithelial cells, comprising contacting said cells with an effective amount of a composition comprising at least one oligonucleotide, wherein the oligonucleotide comprises a base sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 11, SEQ ID NO: 12, and a contiguous portion of any of the foregoing sequences.

Also a part of the invention are compositions comprising one or more oligonucleotides in a physiologically acceptable carrier, wherein the oligonucleotide comprises base sequence SEQ ID NO:1, 2, 3, 4, 5, 6, 7, 8, 11, or 12. Further, the invention can be a composition comprising one or more oligonucleotides in a physiologically acceptable carrier, wherein the oligonucleotide consists of base sequence SEQ ID NO:1, 2, 3, 4, 5, 6, 7, 8, 11 or 12.

Preferred for applications in which it is desired to inhibit cell proliferation are oligonucleotides comprising SEQ ID NO: 1 or SEQ ID NO: 6, or oligonucleotides consisting of SEQ ID NO: 1 or SEQ ID NO: 6. Preferred in applications in which apoptosis is desired are oligonucleotides comprising base sequence SEQ ID NO: 5, or the oligonucleotide consisting of base sequence SEQ ID NO: 5.

Also provided as part of the invention is a composition comprising an oligonucleotide and a physiologically acceptable carrier, wherein the oligonucleotide is pGAGTATGAG (SEQ ID NO:1), pCATAC (SEQ ID NO:6), pGTTAGGGTAG (SEQ ID NO:5), pGGGTTAGGTT (SEQ ID NO:13), or pTAGATGTGGTG (SEQ ID NO:14).

BRIEF DESCRIPTION OF THE DRAWINGS

FIGS. 19A–19H show FACS analysis of propidium iodide stained Jurkat cells (immortalized T lymphocytes), treated with diluent (FIGS. 19A and 19E); 40 µM 11mer-1 pGTTAGGGTTAG (SEQ ID NO:5) (FIGS. 19B and 19F); 40 µM 11mer-2 pCTAACCCTAAC (SEQ ID NO:9) (FIGS. 19C and 19G); 40 µM 11mer-3 pGATCGATCGAT (SEQ ID NO:10) (FIGS. 19D and 19H). Jurkat cells were treated with the stated reagents for 48 hours before analysis (FIGS. 19A–19D) or 72 hours (FIGS. 19E–19H).

FIGS. 20A–20F are profiles showing the results of fluorescence activated cell sorting, for the following additions to the cells: FIG. 20A, diluent; FIG. 20B, 0.4 µM 11mer-1; FIG. 20C, 0.4 µM 11mer-1-S; FIG. 20D, diluent; FIG. 20E, 40 µM 11mer-1; FIG. 20F, 40 µM 11mer-1-S.

FIGS. 21A–21G are profiles showing the results of fluorescence activated cell sorting, for the following additions to the cells: FIG. 21A, diluent; FIG. 21B, 10 µM 11mer-1; FIG. 21C, 10 µM 11mer-1 and 1 µM 11mer-1-S; FIG. 21D, 10 µM 11mer-1 and 5 µM 11mer-1-S; FIG. 21E, 10 µM 11mer-1 and 10 µM 11mer-1-S; FIG. 21F, 20 µM 11mer-1-S; FIG. 21G, 10 µM 11mer-1-S.

FIGS. 30A–30H are profiles of fluorescence intensity as determined by fluorescence activated cell sorting, for the following additions to Jurkat cells: FIGS. 30A and 30E, diluent; FIGS. 30B and 30F, 10 µM pGGGTTAGGGTT (SEQ ID NO:13); FIGS. 30C and 30G, 10 µM pTAGAT-GTGGTG (SEQ ID NO:14); FIGS. 30D and 30H, 10 µM pCGGGCTTATTG (SEQ ID NO:15). Cells were collected and processed for FACS 72 hours after addition of oligonucleotides (FIGS. 30A 30B, 30C and 30D) or 96 hours after addition of oligonucleotides (FIGS. 30E, 30F, 30G and 30H). See Example 31.

FIG. 31A, diluent; FIGS. 31B and 31D, pTT at 20 µM and 5 µM, respectively; FIGS.

31C and 31E, pGTTAGGGTTAG (SEQ ID NO:5) at 20 µM and 5 µM, respectively. See Example 31.

Figures 32A, 32B, 32C, 32D:
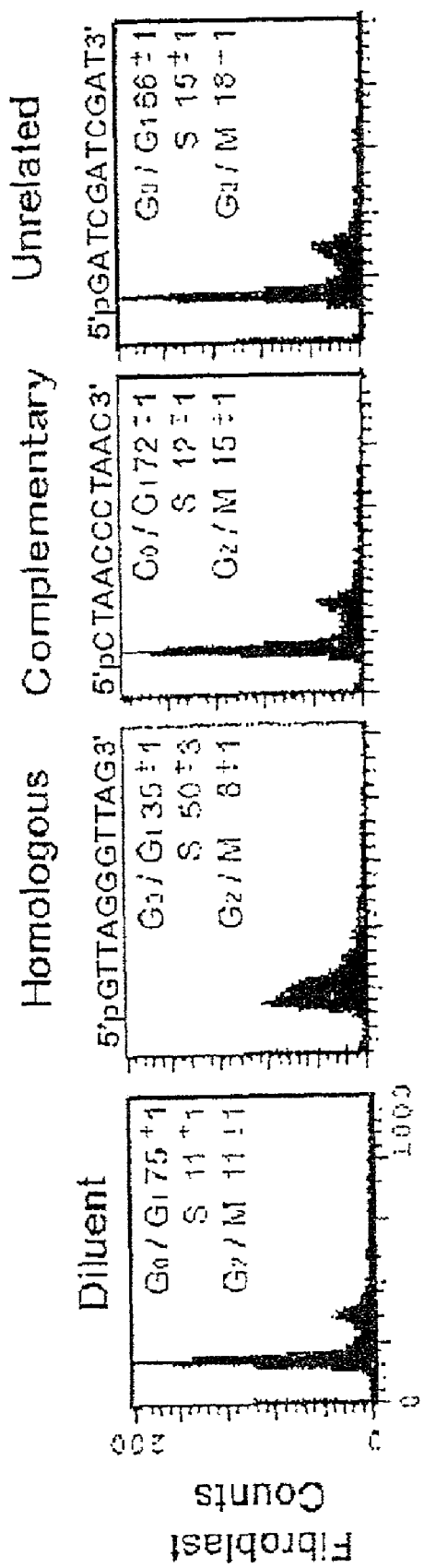

FIGS. 32A–32D are profiles of fluorescence intensity as determined by fluorescence activated cell sorting, for the following additions to preconfluent normal neonatal human fibroblasts: FIG. 32A, diluent; FIG. 32B, pGTTAGGGT-TAG (SEQ ID NO:5) at 40 µM; FIG. 32C, pCTAAC-CCTAAC (SEQ ID NO:9) at 40 µM; FIG. 32D, pGATC-GATCGAT (SEQ ID NO:10) at 40 µM. Cells were analyzed by FACS 24 hours after addition of oligonucleotides or diluent.

FIGS. 33A–33H are profiles of fluorescence intensity as determined by fluorescence activated cell sorting, for the following additions to (FIGS. 33A–33D) SCC12F cells or (FIGS. 33E–33H) Saos-2 cells: FIGS. 33A and 33E, diluent; FIGS. 33B and 33F, pGTTAGGGTTAG (SEQ ID NO:5); FIGS. 33C and 33G, pCTAACCCTAAC (SEQ ID NO:9); FIGS. 33D and 33H, pGATCGATCGAT (SEQ ID NO:10). Cells were analyzed by FACS 48 hours after addition of 40 µM oligonucleotides.

FIGS. 34A–34H are profiles of fluorescence intensity as determined by fluorescence activated cell sorting, for the following additions to (FIGS. 34A–34D) normal control fibroblasts or (FIGS. 34E–34H) NBS fibroblasts: FIGS. 34A and 34E, diluent; FIGS. 34B and 34F, pGTTAGGGTTAG (SEQ ID NO:5); FIGS. 34C and 34G, pCTAACCCTAAC (SEQ ID NO:9); FIGS. 34D and 34H, pGATCGATCGAT (SEQ ID NO:10). Cells were analyzed by FACS 48 hours after addition of 40 µM oligonucleotides or diluent.

Figure 35:
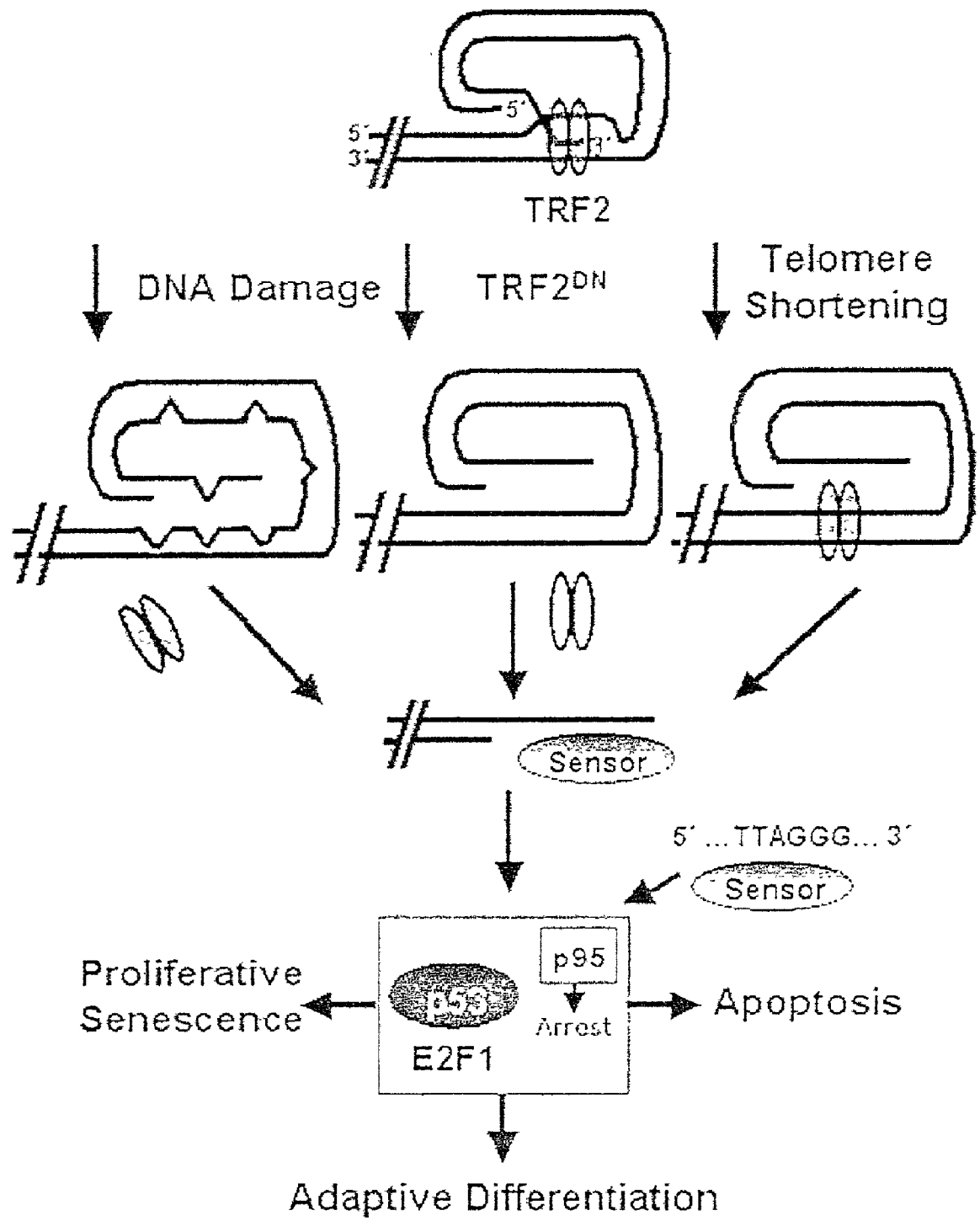

FIG. 35 is a diagram of a proposed mechanism for induction of senescence, cell cycle arrest, adaptive differentiation or apoptosis by exposures of the single-stranded telomere DNA sequence. The 3' telomere overhang is normally sequestered within a loop structure stabilized by TRF2, forming a "capped" or silent telomere. Destabilization of this loop structure by DNA damage due to UV irradiation or chemical adducts, expression of $TRF2^{DN}$, or gradual erosion during aging is hypothesized to expose this single-stranded DNA (repeats of TTAGGG; SEQ ID NO:11), "uncapping" the telomere. Displacement of the TRF2 protein might or might not accompany loop disruption under physiological conditions. This single-stranded DNA is then detected by an as yet unidentified sensor molecule. Interaction of this sensor with the 3' overhang initiates a cascade of events that includes ATM activation, followed by p53 activation and p95/Nbs1 modification leading to cell cycle arrest. Depending on cell type and/or intensity and duration of the signal, these events might lead to the eventual induction of senescence, adaptive differentiation or apoptosis. DNA oligonucleotides homologous to the overhang sequence could be recognized by the same sensor molecule, triggering the cascade in the absence of telomere disruption.

Figure 36:
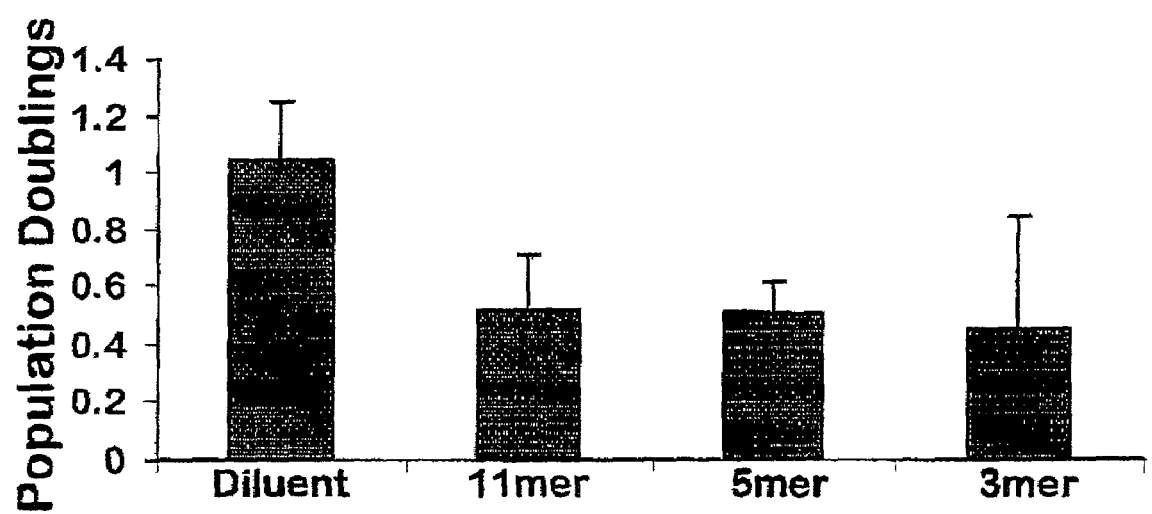

FIG. 36 is a bar graph representing averages of cell population doublings after additions, with standard error of mean, for duplicate cultures of Saos-2 cells treated with oligonucleotides for 36 hours, as described in Example 40.

DETAILED DESCRIPTION OF THE INVENTION

The present invention is based on the discovery that treatment of cells with DNA fragments, oligonucleotides or similar compounds can inhibit cell proliferation, or induce DNA repair or elicit a protective response to subsequent exposure to UV-irradiation or carcinogenic chemicals. pTpT evokes a melanogenic (tanning) response in skin (U.S. Pat. No. 5,643,556, the teachings of which are incorporated herein in their entirety), a protective response to UV irradiation.

More specifically, the invention pertains to the use of compounds such as DNA fragments, polynucleotides, oligonucleotides, deoxynucleotides, dinucleotides, or dinucleotide dimers, or similar compounds, for the inhibition of cell proliferation or induction of DNA repair. As used herein, inhibition of cell proliferation includes complete abrogation of cell division, partial inhibition of cell division and transient inhibition of cell division as measured by standard tests in the art and as described in the Examples. The invention also pertains to the prevention and/or treatment of hyperproliferative diseases, including, but not limited to, cancer and pre-cancerous conditions, wherein the hyperproliferative disease affects cells of any organ and any embryonic origin. Tumors of metastasis, and cells of regrowth and relapse after treatment, as well as primary tumors, can be treated by the methods of the invention. In particular embodiments, the diseases and conditions to be treated include skin diseases such as psoriasis and hyperproliferative, pre-cancerous or UV-induced dermatoses in mammals, particularly in humans.

The invention further pertains to use of the compounds of the present invention to reduce photoaging (a process due in part to cumulative DNA damage), and to reduce oxidative stress and oxidative damage. The invention also pertains to prophylaxis against, or reduction in the likelihood of, the development of skin cancer in a mammal. In addition, the compounds of the present invention can be used to induce apoptosis in cells such as cells that have sustained genetic mutation, such as malignant or cancer cells or cells from an actinic keratosis. The invention further provides compositions comprising said compounds.

All types of cells, and in particular embodiments, epithelial cells, are expected to respond to the methods of the present invention as demonstrated by the representative in vitro and in vivo examples provided herein. Epithelial cells suitable for the method of the present invention include epidermal cells, respiratory epithelial cells, nasal epithelial cells, oral cavity cells, aural epithelial cells, ocular epithelial cells, genitourinary tract cells and esophageal cells, for example. Gastrointestinal cells are also contemplated in methods of the invention as described herein.

Cells that contain damaged or mutated DNA include, for example, actinic keratosis cells, cancer cells, cells that have been irradiated, as with UV, and cells that have been exposed to DNA damaging chemicals or conditions. As described herein, allergically mediated inflammation includes conditions such as atopic dermatitis, contact dermatitis, allergic rhinitis and allergic conjunctivitis.

In one embodiment, the compositions of the present invention comprise DNA oligonucleotides approximately 2–200 bases in length, which can be administered to a mammal (e.g., human) in an appropriate vehicle. In another embodiment, the DNA oligonucleotides are about 2 to about 20 nucleotides in length. In still another embodiment, the oligonucleotides are about 5 to about 11 nucleotides in length. In yet another embodiment, the DNA oligonucleotides are about 2–5 nucleotides in length. As used herein, "DNA fragments" refers to single-stranded DNA fragments, double-stranded DNA fragments, or a mixture of both single- and double-stranded DNA fragments.

It is understood that other base-containing sequences can also be used in the present invention, where bases are, for example, adenine, thymine, cytosine, guanine or uracil. In one embodiment, the oligonucleotides of the present invention comprise a 5' phosphate. A combination of one or more of oligonucleotides of the present invention can also be used.

As shown in the Examples, certain DNA fragments, oligonucleotides and dinucleotides of the present invention caused inhibition of proliferation, melanogenesis, TNFα production and induction of apoptosis in cells, when the cells were contacted with the DNA fragments, oligonucleotides and nucleotides of the present invention. For example, thymidine dinucleotide (pTpT) inhibits proliferation of several human cell types including squamous cell carcinoma, cervical carcinoma, melanoma, neonatal keratinocytes and normal neonatal fibroblasts (Examples 1–5, respectively). pTpT also reduced epidermal proliferation in vivo in a guinea pig model (Example 6). Furthermore, pTpT treatment of cells resulted in the nuclear localization of p53 (Example 7) and the induction of p53-regulated genes (Example 8) such as genes involved in DNA repair. Pretreatment of cells with pTpT enhanced their ability to repair DNA damaged by UV irradiation and by the chemical carcinogen benzo[a]pyrene (Examples 8 and 9). pTpT up-regulated the levels of p53, PCNA and the XPA protein 2 to 3-fold within 2 days of treatment (Example 9). Of note XPA is known not to be p53 regulated, demonstrating that some enhancement of DNA repair capacity may also occur in cells lacking p53. Pretreatment of mouse skin with pTpT also resulted in a reduced level of UV-induced DNA damage (thymine dimers) in vivo (Example 14).

Thymidine dinucleotide, pTpT, mimics some effects of UV light, including inducing melanogenesis and stimulating keratinocyte production of TNFα (Example 4). pTpT also induces TNFα and reduces contact hypersensitivity in vivo (Example 10). UVB radiation is a potent inhibitor of the inductive phase of contact hypersensitivity (CH), and TNFα is a mediator of this suppressive effect. Thymidine dinucleotides (pTpT), a substrate for UV-induced thymine dimer formation, stimulate several effects, including increased tyrosinase expression and melanin content in cultured melanocytes and skin tanning in guinea pigs. As shown in Example 10, the compounds of the present invention also mimic the suppressive effect of UVB on contact hypersensitivity in a mouse model. As demonstrated by the present invention, intracutaneous injection or topical application of pTpT can inhibit the induction of contact hypersensitivity and can activate the TNFα gene in vivo.

Example 10 also demonstrates that pTpT induces production of IL-10 mRNA and protein which is active in inhibiting T cell proliferation in allogenic mixed lymphocyte assay. In human skin, IL-10 as well as TNFα induces specific tolerance for contact hypersensitivity and delayed-type hypersensitivity reactions. Therefore, the DNA fragments, oligonucleotides, deoxynucleotides, dinucleotides and dinucleotide dimers of the present invention are reasonably expected to have immunosuppressive effects in vivo, e.g., to inhibit contact hypersensitivity and delayed-type hypersensitivity.

In further examples, a nine-nucleotide oligomer, GAG-TATGAG (SEQ ID NO: 1) stimulated melanogenesis in human melanocytes and induced the expression of p21/Waf/Cip 1, a growth inhibitory gene product, in a squamous cell carcinoma cell line. Furthermore, a scrambled version of the 9-mer, TAGGAGGAT (SEQ ID NO: 2), and truncated versions of the original 9-mer, AGTATGA (SEQ ID NO: 3), and GTATG (SEQ ID NO: 4), also stimulated melanogenesis in human melanocytes (Example 11). In addition, the sequence pGTTAGGGTTAG (SEQ ID NO: 5) stimulated pigmentation in Cloudman S91 melanoma cells (Example 12) and induced apoptosis in a human T-cell line (Example 13). As demonstrated herein, pGTTAGGGTTAG (SEQ ID NO: 5) induced human T cells to undergo apoptosis, while SEQ ID NOs: 9 and 10 (pCTAACCCTAAC and pGATC-GATCGAT) did not significantly increase apoptosis in these cells (Example 13). Oligonucleotides with sequences SEQ ID NOs: 6–12 demonstrated at least some ability to induce melanogenesis (Examples 11–13).

As demonstrated herein, oligonucleotides as small as dinucleotides (e.g. pTpT) and oligonucleotides of about 20 nucleotides in length can also be used, as it has been demonstrated that oligonucleotides of these lengths are taken up into the cells. In another embodiment, oligonucleotides of about 11 nucleotides can be used. In still another embodiment, oligonucleotides of 5 nucleotides in length can be used to penetrate the skin barrier and effectively induce melanogenesis, inhibit cell growth and induce immunosuppression. These results demonstrate that the in vitro effects of these compounds also occur in vivo upon contacting the cells or tissue of interest with the compounds of the present invention. For example, as demonstrated herein, for the effect of inhibition of cell proliferation, TNF-α production and melanin production, in vitro induction of these activities by the compounds of the present invention is predictive of the ability of these compounds to produce the same effects in vivo. Any suitable method of administering the compounds of the present invention to the organism, such that the compound contacts the cells or tissues of interest, is reasonably expected to be effective. The effects can be optimized using routine optimization protocols.

The compounds of the present invention are therefore useful in methods of inhibiting cell proliferation, preventing cancer, photoaging and oxidative stress by enhancing DNA repair, and, in the skin, by enhancing pigmentation through increased melanin production. Melanin is known to absorb photons in the UV range and therefore its presence reduces the risk of cancer and photoaging.

The DNA fragments, oligonucleotides, deoxynucleotides, dinucleotides, and dinucleotide dimers can be obtained from any appropriate source, or can be synthetically produced. To make DNA fragments, for example, salmon sperm DNA can be dissolved in water, and then the mixture can be autoclaved to fragment the DNA. In one embodiment, the DNA fragments, oligonucleotides, deoxynucleotides, dinucleotides or dinucleotide dimers contain a 5' phosphate.

The compounds of the present invention also play a protective role in UVA-induced oxidative damage to the cell (Example 15). As described in Example 15, primary newborn fibroblasts treated with 10 μM pTpT for 3 days and then stimulated with $5\times10^{-5}$ or $5\times10^{-4}$ $H_2O_2$ had higher cell yields compared to diluent treated controls. Analysis of mRNA and protein revealed that in pTpT treated cells, Cu/Zn superoxide dismutase was elevated. This enzyme participates in the process of oxygen radical quenching. Thus, in one embodiment of the present invention, the compounds of the present invention are administered to cells to protect against oxidative damage. In one embodiment, these compounds are topically administered to the epidermis of an individual.

An "agent that increases activity of p53 protein," as used herein, is an agent (e.g., a drug, molecule, nucleic acid fragment, oligonucleotide, or nucleotide) that increases the activity of p53 protein and therefore results in increase in an DNA repair mechanisms, such as nucleotide excision repair, by the induction of proteins involved in DNA repair, such as PCNA, XPB and p21 proteins. The activity of p53 protein can be increased by directly stimulating transcription of p53-encoding DNA or translation of p53-specific mRNA, by increasing expression or production of p53 protein, by increasing the stability of p53 protein, by increasing the resistance of p53 mRNA or protein to degradation, by causing p53 to accumulate in the nucleus of a cell, by increasing the amount of p53 present, by phosphorylating the serine 15 residue in p53, or by otherwise enhancing the activity of p53. The p53 protein itself is also an agent that increases the activity of p53 protein. A combination of more than one agent that increases the activity of p53 can be used. Alternatively or in addition, the agent that increases the activity of p53 can be used in combination with DNA fragments, deoxynucleotides, or dinucleotides, as described above.

Ultraviolet irradiation produces DNA photoproducts that when not promptly removed, can cause mutations and skin cancer. Repair of UV-induced DNA damage requires efficient removal of the photoproducts to avoid errors during DNA replication. Age-associated decrease in DNA repair capacity is associated with decreased constitutive levels of p53 and other nuclear excision repair (NER) proteins required for removing UV-induced photoproducts. As demonstrated herein, compounds of the present invention induced NER proteins in human dermal cells when these cells were treated with these compounds before UV irradiation (Example 16). While there were age related decreases in NER proteins, NER proteins in cells from donors of all ages from newborn to 90 years were induced by 200–400%. A significant decrease in the rate of repair of thymine dimers and photoproducts occurs with increased age of the cell sample; however, cells that were pre-treated with compounds of the present invention, then UV irradiated, removed photoproducts 30 to 60 percent more efficiently. Thus, the treatment of cells with small DNA oligonucleotides partially compensates for age-associated decreases in DNA repair capacity. In light of the in vivo efficacy of the compounds of the present invention, it is reasonable to expect that treatment of human skin with the compounds of the present invention enhances endogenous DNA repair capacity and reduces the carcinogenic risk from solar UV irradiation. This method is especially useful in older individuals who likely have reduced cellular DNA repair capacity.

DNA fragments, oligonucleotides, deoxynucleotides, dinucleotides or dinucleotide dimers, to be applied to the skin in methods to prevent the sequelae of UV exposure or to reduce the occurrence of skin cancer, to reduce oxidative damage, or to enhance repair of UV-induced damage, can be administered alone, or in combination with physiologically acceptable carriers, including solvents, perfumes or colorants, stabilizers, sunscreens or other ingredients, for medical or cosmetic use. They can be administered in a vehicle, such as water, saline, or in another appropriate delivery vehicle. The delivery vehicle can be any appropriate vehicle which delivers the DNA fragments, oligonucleotides, deoxynucleotides, dinucleotides, or dinucleotide dimers.

To allow access of the active ingredients of the composition to deeper-lying skin cells, vehicles which improve penetration through outer layers of the skin, e.g., the stratum corneum, are useful. Vehicle constituents for this purpose include, but are not limited to, ethanol, isopropanol, diethylene glycol ethers such as diethylene glycol monoethyl ether, azone (1-dodecylazacycloheptan-2-one), oleic acid, linoleic acid, propylene glycol, hypertonic concentrations of glycerol, lactic acid, glycolic acid, citric acid, and malic acid. In one embodiment, propylene glycol is used as a delivery vehicle. In a preferred embodiment, a mixture of propylene glycol:ethanol:isopropyl myristate (1:2.7:1) containing 3% benzylsulfonic acid and 5% oleyl alcohol is used.

In another embodiment, a liposome preparation can be used. The liposome preparation can comprise liposomes which penetrate the cells of interest or the stratum corneum, and fuse with the cell membrane, resulting in delivery of the contents of the liposome into the cell. For example, liposomes such as those described in U.S. Pat. No. 5,077,211 of Yarosh, U.S. Pat. No. 4,621,023 of Redziniak et al. or U.S. Pat. No. 4,508,703 of Redziniak et al. can be used. The compositions of the invention intended to target skin conditions can be administered before, during, or after exposure of the skin of the mammal to UV or agents causing oxidative damage. Other suitable formulations can employ niosomes. Niosomes are lipid vesicles similar to liposomes, with membranes consisting largely of non-ionic lipids, some forms of which are effective for transporting compounds across the stratum corneum.

Other suitable delivery methods intended primarily for skin include use of a hydrogel formulation, comprising an aqueous or aqueous-alcoholic medium and a gelling agent in addition to the oligonucleotide(s). Suitable gelling agents include methylcellulose, carboxymethylcellulose, hydroxypropylmethylcellulose, carbomer (carbopol), hypan, polyacrylate, and glycerol polyacrylate.

In one embodiment, the DNA fragments, oligonucleotides, deoxynucleotides, dinucleotides, dinucleotide dimers, agent to inhibit apoptosis, or composition comprising one or more of the foregoing, is applied topically to the skin surface. In other embodiments, the DNA fragments, oligonucleotides, deoxynucleotides, dinucleotides, dinucleotide dimers, agent that inhibits apoptosis, or composition comprising one or more of the foregoing, is delivered to other cells or tissues of the body such as epithelial cells. Cells of tissue that is recognized to have a lesser barrier to entry of such substances than does the skin can be treated, e.g., orally to the oral cavity; by aerosol to the respiratory epithelium; by instillation to the bladder epithelium; by instillation or suppository to intestinal (epithelium) or by other topical or surface application means to other cells or tissues in the body, including eye drops, nose drops and application using angioplasty, for example. Furthermore, the oligonucleotides of the present invention can be administered intravenously or injected directly into the tissue of interest intracutaneously, subcutaneously, intramuscularly or intraperitoneally. In addition, for the treatment of blood cells, the compounds of the present invention can be administered intravenously or during extracorporeal circulation of the cells, such as through a photophoresis device, for example. As demonstrated herein, all that is needed is contacting the cells of interest with the oligonucleotide compositions of the present invention, wherein the oligonucleotides contacting the cells can be as small as dinucleotides.

The DNA fragments, oligonucleotides, deoxynucleotides, dinucleotides, dinucleotide dimers, agent that promotes differentiation, agent that increases p53 activity, or composition comprising one or more of the foregoing, is administered to (introduced into or contacted with) the cells of interest in an appropriate manner. The "cells of interest," as used herein, are those cells which may become affected or are affected by the hyperproliferative disease or precancerous condition, or cells which are affected by oxidative stress, DNA-damaging conditions such as UV irradiation or exposure to DNA damaging chemicals such as benzo[a]pyrene. Specifically encompassed by the present invention are epithelial cells, including melanocytes and keratinocytes, as well as other epithelial cells such as oral, respiratory, bladder and cervical epithelial cells. As demonstrated herein, methods and compositions of the present invention can inhibit growth, induce melanogenesis and induce TNFα production in epithelial cells from numerous sources.

The oligonucleotides, DNA fragments, deoxynucleotides, dinucleotides, dinucleotide dimers, agent that promotes differentiation, agent that increases p53 activity, agent that inhibits apoptosis, or composition comprising one or more of the foregoing, is applied at an appropriate time, in an effective amount. The "appropriate time" will vary, depending on the type and molecular weight of the oligonucleotides, DNA fragments, deoxynucleotides, dinucleotides, dinucleotide dimers, or other agent employed, the condition to be treated or prevented, the results sought, and the individual patient. An "effective amount," as used herein, is a quantity or concentration sufficient to achieve a measurable desired result. The effective amount will depend on the type and molecular weight of the oligonucleotides, DNA fragments, deoxynucleotides, dinucleotides, dinucleotide dimers, or agent employed, the condition to be treated or prevented, the results sought, and the individual patient. For example, for the treatment or prevention of psoriasis, or for hyperproliferative, cancerous, or pre-cancerous conditions, or UV-induced dermatoses, the effective amount is the amount necessary to reduce or relieve any one of the symptoms of the disease, to reduce the volume, area or number of cells affected by the disease, to prevent the formation of affected areas, or to reduce the rate of growth of the cells affected by a hyperproliferative disorder. The concentration can be approximately 2–300 μM. In a another embodiment, the concentration of agent (e.g., oligonucleotide) is about 50–200 μM; in another embodiment, the concentration is about 75–150 μM.

In one embodiment of the present invention, oligonucleotides, DNA fragments, such as single-stranded DNA fragments, deoxynucleotides, dinucleotides, or dinucleotide dimers, agent that increases p53 activity, agent that promotes differentiation, or a composition that can comprise one or more of the foregoing, is administered, in an appropriate delivery vehicle, to the cells of interest in the mammal in order to treat or prevent a hyperproliferative disease affecting epithelial cells. The DNA fragments, oligonucleotides, deoxynucleotides, dinucleotides, dinucleotide dimers, agent that promotes differentiation, agent that increases p53 activity, agent that inhibits apoptosis, or composition comprising one or more of the foregoing, can be administered systemically, can be administered directly to affected areas, or can be applied prophylactically to regions commonly affected by the hyperproliferative disease.

In another embodiment, the DNA fragments, oligonucleotides, deoxynucleotides, dinucleotides, dinucleotide dimers, agent that increases p53 activity, agent that promotes differentiation, or composition comprising one or more of the foregoing, is administered to the epidermis for the treatment or prevention of oxidative stress or for the treatment or prevention of hyperproliferative, cancerous, or pre-cancerous conditions, or UV-responsive dermatoses.

In still another embodiment, DNA fragments, oligonucleotides, deoxynucleotides, dinucleotides, dinucleotide dimers, agent that promotes differentiation, agent that increases p53 activity, or a composition comprising one or more of the foregoing, can be administered, either alone or in an appropriate delivery vehicle, to the epidermis for reduction of photoaging, or prophylaxis against or reduction in the likelihood of development of skin cancer. The DNA fragments, oligonucleotides, deoxynucleotides, dinucleotides, dinucleotide dimers, agent that promotes differentiation, agent that increases p53 activity, or composition comprising one or more of the foregoing, can be administered topically or by intracutaneous injection at an appropriate time (i.e., prior to exposure of the skin to UV irradiation). The DNA fragments, oligonucleotides, deoxynucleotides, dinucleotides, dinucleotide dimers, agent that promotes differentiation, agent that increases p53 activity, or composition comprising one or more of the foregoing, can be applied before, during or after exposure to a carcinogen such as UV irradiation. They can be applied daily or at regular or intermittent intervals. In one embodiment, the DNA fragments, oligonucleotides, deoxynucleotides, dinucleotides, dinucleotide dimers, agent that promotes differentiation, agent that increases p53 activity, or composition comprising one or more of the foregoing, can be administered on a daily basis to skin which may be exposed to sunlight during the course of the day.

In a further embodiment of the invention, the DNA fragments, oligonucleotides, deoxynucleotides, dinucleotides, dinucleotide dimers, agent that promotes differentiation, agent that increases p53 activity, or composition comprising one or more of the foregoing, is administered, in an appropriate delivery vehicle, to an individual (e.g., epithelial cells or other cells of an individual) for the treatment or prevention of hyperproliferative, cancerous or pre-cancerous conditions, or to repair or prevent DNA damage caused by DNA damaging chemicals, such as benzo[a]pyrene.

As demonstrated herein, the compounds of the present invention are active in vitro and in vivo in their unmodified form, e.g., sequences of unmodified oligonucleotides linked by phosphodiester bonds. As used herein, the terms "oligonucleotide," "dinucleotide," "DNA fragment," etc., refer to molecules having deoxyribose as the sugar, and having phosphodiester linkages ("phosphate backbone") as occur naturally, unless a different linkage or backbone is specified.

Furthermore, although not necessary for the ability to elicit the UV-mimetic effects of the present invention, the compounds of the present invention can be modified, derivative or otherwise combined with other reagents to increase the half life of the compound in the organism and/or increase the uptake of these compounds by the cells of interest. Modification reagents include, for example, lipids or cationic lipids. In one embodiment, the compounds of the present invention are covalently modified with a lipophilic group, an adamancy moiety. The compounds of the present invention can be modified to target specific tissues in the body. For example, brain tissue can be targeted by conjugating the compounds with biotin and using the conjugated compounds with an agent that facilitates delivery across the blood-brain barrier, such as anti-transferring receptor antibody coupled to streptavidin.

From the results of experiments described in Examples 17–20, it can be concluded that the activity of pTpT and the activity of the telomere overhang repeat homolog oligonucleotide 11mer-1 (SEQ ID NO: 5) require that they be hydrolyzable to induce apoptosis, cell cycle arrest, and melanogenesis. The non-hydrolyzable phosphorothioate form of these oligonucleotides has the ability to inhibit the activity of the hydrolyzable molecules and can be used to block the intracellular responses in vivo as well as in vitro.

The Examples, especially Example 31, demonstrate that telomere homolog oligonucleotides but not complementary or unrelated DNA sequences of the same length induce an S-phase arrest and apoptosis in an established human lymphocyte line and in a human melanoma cell line. The effects are not due to selective uptake of the telomere homolog, as the control sequences are taken up comparably in the present study. Oligonucleotides partially homologous to the 3' overhang sequence produce qualitatively the same responses but to a lesser degree or at a higher concentration. Thus, an 11 base oligonucleotide with 55% identity with the telomere overhang repeat sequence telomere is intermediate between the 11mer-1 (100% nucleotide sequence identity with telomere repeat) and 11mer-2 (complementary to telomere repeat) or 11mer-3 (unrelated to telomere repeat) in producing apoptosis. pTT, corresponding to one-third of the TTAGGG (SEQ ID NO:11) repeat sequence, duplicates the 11mer-1 effect on cell cycle arrest but at a 4-fold higher concentration. In work comparing pTT to a 9 base oligonucleotide with 56% sequence identity with (TTAGGG)$_n$, the oligonucleotide having 56% sequence identity was found to have an ability comparable to pTT to induce p53 and p53-regulated genes at 40% the concentration, at 40 μM versus 100 μM pTT.

The oligonucleotide pTT has been shown to induce and activate p53 and to transcriptionally upregulate a number of genes, many but not all of which are known to be p53 regulated. Experiments with the 11mer-1 complete homolog demonstrate that the S-phase arrest induces results from phosphorylation of the p95/Nbs1 protein, which also mediates S-phase arrest following ionizing radiation. Of note, this decreases proliferation of cells lacking functional p53. Furthermore, as anticipated from the fact that p95/Nbs1 is phosphorylated by the ATM kinase (Gatei, M., et al., (2000), *Nat Genet* 25, 115–119; Wu, X., et al., (2000), *Nature* 25, 477–482; Lim, D. S., et al., (2000), *Nature* 404, 613–617; Zhao, S., et al. (2000), *Nature* 405, 473–477), the oligonucleotide effects also require ATM and are not observed in cells from patients with ataxia telangiectasia in whom the ATM kinase is mutated.

Experimental telomere disruption [Karlseder, J., et al., 1999, *Science* 283: 1321–1325] and cellular manipulations that precipitate premature senescence, such as transfection with the ras oncogene or exposure to oxidative stress, are known to digest the 3' telomere overhang and/or to shorten overall telomere length. In contrast, exposure of cells to telomere homolog oligonucleotides in the present studies increases mean telomere length (MTL). While not wishing to be bound by a single mechanism, these data strongly suggest that the oligonucleotides can activate telomerase, presumably by inducing TERT, and imply that transient activation of telomerase may be a part of the physiologic telomere-based DNA damage response that also includes activation of the ATM kinase with subsequent signaling through p53 and p95/Nbs1. The apparent ability of oligonucleotides to induce this response in the absence of DNA damage and telomere disruption offers the possibility of "rejuvenating" cells through telomere elongation, as recently reported in human skin equivalent constructs containing fibroblasts transfected with TERT, without the enhanced risk of carcinogenesis observed even in even normal cells that ectopically express telomerase. Equally, the phenomenon suggests that the advantages of robust DNA damage responses of the type observed in p53 over-expressing mice could be separated from the premature senescence also observed in the transgenic animals (Tyner, S. D., et al., 2002, *Nature* 415: 45–523). Such "rejuvenation" or delay in acquiring the senescent phenotype associated with critical telomere shortening would be in addition to other benefits that might accrue from treatment with oligonucleotides partially or completely homologous to the TTAGGG (SEQ ID NO:11) repeated sequence. Based on extensive work in vivo as well as in vitro, these are understood to include sunless tanning and related photoprotection, enhanced DNA repair capacity, cancer prevention and treatment, and immunomodulation.

Under normal conditions, the 3' telomere overhang DNA sequence is believed to be folded back and concealed in a loop structure stabilized by TRF2 [Griffith, J. D., et al., (1999), *Cell* 97, 503–514]. However, this sequence might be exposed if the telomere were distorted, for example by ultraviolet (UV)-induced thymine dimers or carcinogen adducts involving guanine residues (as with cisplatin or benzo[a]pyrene) that could render the loop-back configuration unstable. Exposure of the TTAGGG (SEQ ID NO:11) repeat sequence could be the initial signal leading to a variety of DNA damage responses, dependent on cell type as well as intensity and/or duration of the signal. These responses include cell cycle arrest, apoptosis, and a more differentiated sometimes adaptive phenotype, for example, increased melanin production (tanning). See FIG. 35.

The proposed model predicts that inability to repair damage to telomeric DNA would lead to exaggerated damage responses, such as p53 induction and apoptosis, as has been reported for UV-irradiated xeroderma pigmentosum cells that cannot efficiently remove DNA photoproducts (Dumaz, N., et al., 1998, *Carcinogenesis* 19: 1701–1704). This model is further consistent with the recent finding that transgenic mice with supra-normal p53 activity are highly resistant to tumors, yet age prematurely (Tyner, S. D., et al., 2002, *Nature* 415: 45–523). A DNA damage recognition mechanism might have evolved to contain predominantly thymidine and guanine bases. The TTAGGG (SEQ ID NO:11) repeat sequence is an excellent target for DNA damage, as dithymidine sites most commonly participate in formation of UV photoproducts (Setlow, R. B. and W. L. Carrier. 1966, *J Mol Biol* 17: 237–254) and guanine is both the principal site of oxidative damage, forming 8-oxoguanine [Kasai, H. and S. Nishimura, 1991. "Oxidative Stress: Oxidants and Antioxidants," pp. 99–116 In H. Sies (ed.) (London, Academic Press, Ltd.)], as well as the base to which most carcinogens form adducts [Friedberg, E. C., et al., 1995, pp. 1–58 In E. C. Friedberg, G. C. Walker and W. Siede, eds. (Washington, D.C., ASM Press)].

The postulated telomere-initiated signal transduction pathway would provide a single evolutionary point of departure for several distinct defenses against carcinogenesis in higher organisms: permanent loss of proliferative capacity (senescence) in cells expected on a statistical basis alone to have accumulated multiple mutations throughout the genome during prolonged environmental exposure and serial rounds of DNA replication and cell division; transient cell cycle arrest to increase the time available for repair before resuming DNA replication; activation of a cell suicide program to remove cells from the tissue if damage exceeds the repair capacity, since acute telomeric damage would be expected to reflect the degree of DNA damage throughout the genome; and induction over several days of adaptive responses, such as tanning, to reduce DNA photoproduct formation and/or enhanced DNA repair capacity to prevent damage from similar insults in the future.

The invention includes methods for treating a hyperproliferative disorder in a mammal, in which the therapy includes administering to the mammal an effective amount of a composition comprising one or more oligonucleotides which share at least 50% nucleotide sequence identity with the vertebrate telomere overhang repeat. These methods can be applied especially to human subjects. Hyperproliferative disorders can be characterized by benign growth of cells beyond a normal range, and which sometimes may result in a benign tumor or widespread epidermal thickening, as in psoriasis. Also among the various hyperproliferative disorders to be treated by these methods are cancer as it is manifested in various forms and arising in various cell types and organs of the body, for example, cervical cancer, lymphoma, osteosarcoma, melanoma and other cancers arising in the skin, and leukemia. Also among the types of cancer cells to which the therapies are directed are breast, lung, liver, prostate, pancreatic, ovarian, bladder, uterine, colon, brain, esophagus, stomach, and thyroid.

The oligonucleotides can be administered in the methods of treatment described herein as a single type of oligonucleotide or in a combination comprising with one or more different oligonucleotides. Oligonucleotides without a 5' phosphate can be used in any of the methods of therapy for treatment, or for the reduction of incidence of a disease or disorder described herein. However, oligonucleotides having a 5' phosphate are preferred, as it has been shown that the 5' phosphate improves uptake of the oligonucleotide into cells. The oligonucleotides can be at least 2 nucleotides in length, preferably 2–200 nucleotides, and more preferably from 2 to 20 nucleotides in length. Oligonucleotides 5–11 nucleotides are more preferred.

The telomere overhang repeat sequence of vertebrates is $(TTAGGG)_n$. The invention encompasses methods in which the oligonucleotides administered for therapy have at least 50% nucleotide sequence identity to the telomere repeat sequence. Preferred are oligonucleotides having at least 60% nucleotide sequence identity. More preferred are oligonucleotides having at least 70% nucleotide sequence identity. Still more preferred are those oligonucleotides having at least 80% nucleotide sequence identity. More highly preferred are oligonucleotides having at least 90% nucleotide sequence identity. Most preferred are oligonucleotides having 100% nucleotide sequence identity to $(TTAGGG)_n$. The particular telomere repeat homologs pGAGTATGAG (SEQ ID NO:1), pGTTAGGGTTAG (SEQ ID NO:5; also called "11mer-1" and "T-oligo" herein), pGGGTTAGGGTT (SEQ ID NO:13) and pTAGATGTGGTG (SEQ ID NO:14) are especially preferred where it is desired to use an oligonucleotide sharing at least 50% nucleotide sequence identity with the telomere repeat sequence. Other oligonucleotides having at least 50% nucleotide sequence identity with the telomere overhang repeat sequence can be used as anti-proliferative agents, for example pTAGGAGGAT (SEQ ID NO:2), pAGTATGA (SEQ ID NO:3), and pGTATG (SEQ ID NO:4).

Oligonucleotides are relatively short polynucleotides. Polynucleotides are linear polymers of nucleotide monomers in which the nucleotides are linked by phosphodiester bonds between the 3' position of one nucleotide and the 5' position of the adjacent nucleotide. Unless otherwise indicated, the "oligonucleotides" of the invention as described herein have a phosphodiester backbone.

Sequence identity is determined by a best fit alignment of the oligonucleotide in question with $(TTAGGG)_n$. The sequences are compared at each position, and a determination of "match" or "no match" is made at each nucleotide position, and the percent of matches, without resorting to deletion or insertion in either sequence, is the percent identity of the sequences as counted along the oligonucleotides in question. Thus, by illustration, SEQ ID NO:5 shares 100% sequence identity with $(TTAGGG)_n$. SEQ ID NO:1 shares 5/9 sequence identity with $(TTAGGG)_n$. SEQ ID NO:4 shares 3/5 sequence identity with $(TTAGGG)_n$. pTT shares 100% sequence homology with $(TTAGGG)_n$.

Particular molecules found to have an anti-proliferative effect, and thus appropriate for use in methods to reduce proliferation of cells in a mammal, are the oligonucleotides thymidine dinucleotide ("pTpT" or "pTT" or "$T_2$") and pCATAC (SEQ ID NO:6).

Another part of the invention is a method for promoting differentiation of malignant cells in a mammal, the method comprising administering to the mammal an effective amount of a composition comprising one or more oligonucleotides which share at least 50% nucleotide sequence identity with $(TTAGGG)_n$. A differentiated state, can in many ways, be considered the opposite of a malignant state. Depending on the cell type, differentiation can involve the regulation of expression of a number of different genes to result in an increase or decrease in certain enzymatic activities, or cell surface proteins, for example. For example, melanocytes respond to oligonucleotides with an increase in tyrosinase expression.

Herein, an association has been found between the inhibition of growth of cancer cells, caused by the cells taking up oligonucleotides with sequence identity to the telomere repeat sequence, and an increase in the appearance on the cell surface of antigens typical of differentiated cells, rather than cancer cells. Thus, a further method of the invention is to enhance the expression of one or more surface antigens indicative of differentiation of cancer cells in a mammal, said method comprising administering to the mammal an effective amount of one or more oligonucleotides as described herein, for example, one or more oligonucleotides which share at least 50% nucleotide sequence identity with the vertebrate telomere overhang repeat.

This inducement of the cells to a more differentiated state, or to take on one or more characteristics of differentiation, can be exploited in immunotherapy methods. The surface antigens associated with a differentiated state, fragments thereof, or synthetic peptides derived from the studies of the externally exposed loops of the surface antigens, can be incorporated into a vaccine to induce a cancer patient to produce cytotoxic T lymphocytes against the cells displaying the cell surface antigen. For example, in melanoma cells, the cell surface antigens MART-1, tyrosinase, TRP-1 or gp-100, or combinations thereof, can be made to increase on the cell surface when the cells take up oligonucleotides sharing at least 50% nucleotide sequence identity with the telomere overhang repeat. See Example 29. These cell surface antigens can become targets for immunotherapy, for example by vaccinations with the isolated cell surface antigen or peptides having amino acid sequences derived from the surface loops of the antigens. See, for example, Jäger, E. et al., Int. J. Cancer 66:470–476, 1996; Kawakami, Y. et al., J. Immunol. 154:3961–3968, 1995; and de Vries, T. J. et al., J. Pathol. 193:13–20, 2001.

Telomerase has been a target for antiproliferative methods based on theories of using antisense oligonucleotides to bind to the RNA portion of the enzyme. However, the therapeutic methods described herein can be used independently of the presence or function of telomerase in the target cells. The telomere repeat overhang homolog pGTTAGGGTTAG (SEQ ID NO:5) was seen to bring about S-phase cell cycle arrest in normal fibroblasts and in cells of the osteosarcoma cell line Saos-2, neither of which have telomerase activity. See Examples 32 and 34. Thus, for cancer cells, most of which have telomerase activity, but some of which do not, the present method can be used regardless of telomerase activity. The inhibition of growth of the cancer cells is characterized by cell cycle arrest, apoptosis, and/or differentiation to a more differentiated state. A method for inhibiting the growth of cancer cells in a mammal (e.g., human), operational independent of the telomerase (+) or telomerase (−) state of the cancer cells, is to administer to the mammal an effective amount of a composition comprising one or more oligonucleotides which share at least 50% nucleotide sequence identity with the telomere overhang repeat.

The experiments described in Example 34 demonstrate that the function of a wild type p53 protein is also not necessary to bring about the S-phase cell cycle arrest in tumors or tumor cells treated with an oligonucleotide with at least 50% sequence identity to the telomere repeat sequence. A p53-null osteosarcoma cell line was shown to respond to the addition of pGTTAGGGTTAG (SEQ ID NO:5) by arresting in S-phase. Thus, the method for inhibiting the growth of cancer cells in a mammal, the method including administering to the human an effective amount of a composition comprising one or more oligonucleotides which share at least 50% nucleotide sequence identity with the human telomere overhang repeat, can be carried out whether or not the target cells have normal p53 function.

The invention further comprises a method for preventing the sequelae of exposure of the skin of a mammal to ultraviolet light—spongiosis, blistering or dyskeratosis, or any combination of these—by administering to the skin an effective amount of a composition comprising one or more oligonucleotides which share at least 50% nucleotide sequence identity with the telomere overhang repeat. The steps or steps of this method can also be used in the reduction in the incidence of skin cancer in a human, and is particularly applicable to reduce the occurrence of skin cancer in patients with xeroderma pigmentosum or other genetic predisposition to skin cancer. The method of applying to the skin an effective amount of a composition comprising one or more oligonucleotides which share at least 50% nucleotide sequence identity with the telomere overhang repeat is also a method for enhancing repair of ultraviolet irradiation-induced damage to skin. Any of the oligonucleotides described herein and characterized by having at least 50% sequence identity to the telomere repeat sequence found in humans—the oligonucleotides pGAGTATGAG (SEQ ID NO:1), pCATAC (SEQ ID NO:6), pGTTAGGGTTAG (SEQ ID NO:5), pGGGTTAGGGTT (SEQ ID NO:13), or pTAGATGTGGTG (SEQ ID NO:14), for example, can be used in the methods. Further, the oligonucleotides pTT and pGAGTATGAG (SEQ ID NO:1) can also be used in the methods.

Oxidative damage is characterized by the reaction products of reactions of molecules found in the cells with reactive oxygen species (ROS), such as hydrogen peroxide, hydroxyl radicals, and superoxide. Oxidative damage can result, for instance, from normal cellular metabolism, UVA irradiation, ionizing radiation, or exposure to a variety of chemicals. Reactive oxygen species can be measured in a number of ways. One assay employs a probe dichlorofluorescin diacetate (Molecular Probes, Inc.), a colorless reagent that is taken up by the cells and becomes fluorescent upon oxidation by ROS. The level of fluorescence correlates with the intracellular ROS level.

Applicants have also described a method for reducing oxidative damage in a mammal, the method having a step of administering to the mammal an effective amount of a composition comprising administering to the mammal, especially to the skin of the mammal, an effective amount of a composition comprising one or more oligonucleotides which share at least 50% nucleotide sequence identity with the human telomere overhang repeat. Preferred are embodiments in which the oligonucleotide is pGAGTATGAG (SEQ ID NO:1). Also effective in the method is pTT. See results in Examples 15, 21, 22 and 23 suggesting that oligonucleotide treatment should enhance the ability of cells to repair oxidative DNA damage.

Applicants have further described a method for treating melanoma in a mammal, comprising administering to the human an effective amount of a composition comprising one or more oligonucleotides that share at least 50% nucleotide sequence identity with the human telomere overhang repeat. In particular cases, the oligonucleotide can be pGTTAGGGTTAG (SEQ ID NO:5); pTT can also be used in the method. Applicants have shown the effectiveness of oligonucleotide therapy using human melanoma cells in a mouse model. See Example 30.

Another aspect of the invention concerns a method for reducing proliferation of keratinocytes in the skin of a human, in which the method comprises applying to the skin an effective amount of a composition comprising one or more oligonucleotides that share at least 50% nucleotide sequence identity with the human telomere overhang repeat. The method is applicable to disorders of the skin characterized by proliferation of keratinocytes in the skin, such as seborrheic keratosis, actinic keratosis, Bowen's disease, squamous cell carcinoma or basal cell carcinoma. Also effective in the method is pTT.

The present invention includes the method of treating a disease or disorder in a mammal, wherein the disease or disorder is characterized by abnormal proliferation of cells, including, but not limited to, cancers, solid tumors, blood-born tumors (e.g., leukemias), tumor metastases, benign tumors (e.g., hemangiomas, acoustic neuromas, neurofibromas, trachomas, and pyogenic granulomas), and psoriasis. Hyperproliferative disorders can also be those characterized by excessive or abnormal stimulation of fibroblasts, such as scleroderma, and hypertrophic scars (i.e., keloids).

The oligonucleotide or oligonucleotides to be used in therapies to alleviate hyperproliferative disorders such as cancer can be used in a composition in combination with a pharmaceutically or physiologically acceptable carrier. Such a composition may also contain in addition, diluents, fillers, salts, buffers, stabilizers, solubilizers, and other materials well known in the art. Cationic lipids such as DOTAP [N-(2,3-dioleoyloxy)propyl]-N,N,N-trimethylammonium salts may be used with oligonucleotides to enhance stability. Oligonucleotides may be complexed with PLGA/PLA copolymers, chitosan or fumaric acid/sebacic acid copolymers for improved bioavailability {where PLGA is [poly (lactide-co-glycolide)]; PLA is poly(L-lactide)}. The terms "pharmaceutically acceptable" and "physiologically acceptable" mean a non-toxic material that does not interfere with the effectiveness of the biological activity of the active ingredient(s). The characteristics of the carrier will depend on the route of administration.

A composition to be used as an antiproliferative agent may further contain other agents which either enhance the activity of the oligonucleotide(s) or compliment its activity or use in treatment, such as chemotherapeutic or radioactive agents. Such additional factors and/or agents may be included in the composition to produce a synergistic effect with the oligonucleotide(s), or to minimize side effects. Additionally, administration of the composition of the present invention may be administered concurrently with other therapies, e.g., administered in conjunction with a chemotherapy or radiation therapy regimen.

The oligonucleotides as described herein can be used in combination with other compositions and procedures for the treatment of diseases. For example, a tumor may be treated conventionally with surgery, radiation, chemotherapy, or immunotherapy, combined with oligonucleotide therapy, and then oligonucleotides may be subsequently administered to the patient to extend the dormancy of micrometastases and to stabilize and inhibit the growth of any residual primary tumor.

The compositions of the present invention can be in the form of a liposome in which oligonucleotide(s) of the present invention are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like.

Pharmaceutical compositions can be made containing oligonucleotides to be used in antiproliferative therapy. Administration of such pharmaceutical compositions can be carried out in a variety of conventional ways known to those of ordinary skill in the art, such as oral ingestion, inhalation, for example, of an aerosol, topical or transdermal application, or intracranial, intracerebroventricular, intracerebral, intravaginal, intrauterine, oral, rectal or parenteral (e.g., intravenous, intraspinal, subcutaneous or intramuscular) route, or cutaneous, subcutaneous, intraperitoneal, parenteral or intravenous injection. The route of administration can be determined according to the site of the tumor, growth or lesion to be targeted.

To deliver a composition comprising an effective amount of one or more oligonucleotides to the site of a growth or tumor, direct injection into the site can be used. Alternatively, for accessible mucosal sites, ballistic delivery, by coating the oligonucleotides onto beads of micometer diameter, or by intraoral jet injection device, can be used.

Viral vectors for the delivery of DNA in gene therapy have been the subject of investigation for a number of years. Retrovirus, adenovirus, adeno-associated virus, vaccinia virus and plant-specific viruses can be used as systems to package and deliver oligonucleotides for the treatment of cancer or other growths. Adeno-associated virus vectors have been developed that cannot replicate, but retain the ability to infect cells. An advantage is low immunogenicity, allowing repeated administration. Delivery systems have been reviewed, for example, in Page, D. T. and S. Cudmore, *Drug Discovery Today* 6:92–1010, 2001.

Studies carried out using oligonucleotides on the theory of their inhibiting the function of a target nucleic acid (antisense oligonucleotides), most of these studies carried out with phosphorothioate oligonucleotides, have found delivery to target cells to not be a major problem. Antisense oligonucleotides in clinical trials have been administered in saline solutions without special delivery vehicles (reviewed in Hogrefe, R. I., Antisense and Nucleic Acid Drug Development 9:351–357, 1999).

Formulations suitable for parenteral administration include aqueous and non-aqueous sterile injection solutions which may contain anti-oxidants, buffers, bacteriostats and solutes which render the formulation isotonic with the fluids of the intended recipient; and aqueous and non-aqueous sterile suspensions which may include suspending agents and thickening agents. The formulations may be presented in unit-dose dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described. A preferred pharmaceutical composition for intravenous, cutaneous, or subcutaneous injection should contain, in addition to oligonucleotide(s) of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

Use of timed release or sustained release delivery systems are also included in the invention. Such systems are highly desirable in situations where surgery is difficult or impossible, e.g., patients debilitated by age or the disease course itself, or where the risk-benefit analysis dictates control over cure. One method is to use an implantable pump to deliver measured doses of the formulation over a period of time, for example, at the site of a tumor.

A sustained-release matrix can be used as a method of delivery of a pharmaceutical composition comprising oligonucleotides, especially for local treatment of a growth or tumor. It is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The amount of oligonucleotide of the present invention in the pharmaceutical composition of the present invention will depend upon the nature and severity of the condition being treated, and on the nature of prior treatments which the patient has undergone. For a human patient, the attending physician will decide the dose of oligonucleotide of the present invention with which to treat each individual patient. Initially, the attending physician can administer low doses and observe the patient's response. Larger doses may be administered until the optimal therapeutic effect is obtained for the patient, and at that point the dosage is not increased further. The duration of therapy using the pharmaceutical composition of the present invention will vary, depending on the severity of the disease being treated and the condition and potential idiosyncratic response of each individual patient.

The invention is further illustrated by the following non-limiting Examples.

EXAMPLES

Example 1

Application to Human Squamous Carcinoma Cells

Figure 1:
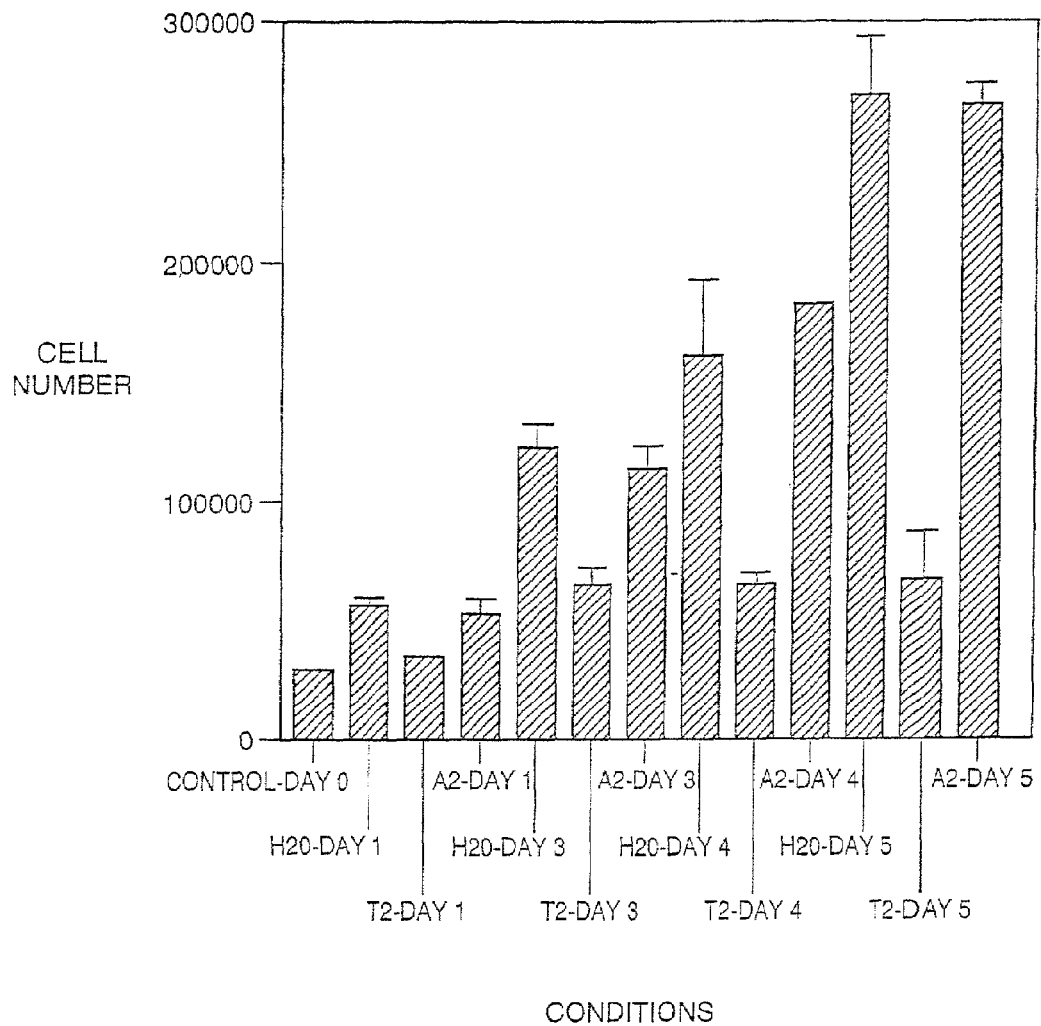
FIG. 1 is a graphic representation of the cell growth rate of human squamous carcinoma cells dosed with water (diluent), 100 µM pTpT ($T_2$) or 100 µM pdApdA ($A_2$), where day 0 is before dosage and days 1, 3, 4 and 5 are days after dosage.

Human squamous carcinoma cell line SCC12F cells were maintained in primary keratinocyte medium (300 ml DME, 100 ml F-12 nutrient supplement, 50 ml 10× adenine, 50 ml fetal bovine serum, 5 ml penicillin/streptomycin stock, and 0.5 ml of 10 µg/ml epidermal growth factor and hydrocortisone to final concentration of 1.4 µg/ml) and dosed with either water (diluent), 100 µM pTpT ($T_2$, Midland Certified Reagent Company, Midland, Tex.) or 100 µM pdApdA ($A_2$). Cells were harvested before dosing (day 0), and 1, 3, 4, and 5 days after dosage, and were counted by Coulter™ counter. After harvesting, the cells were processed for total RNA isolation and were analyzed by Northern blot. Addition of pTpT to human squamous carcinoma cells resulted in marked decreases in cell growth rate, as shown in FIG. 1. Addition of a control deoxyadenine dinucleotide (pdApdA), a compound very similar to pTpT but not readily dimerized by UV irradiation, and therefore rarely excised during the course of UV-induced DNA repair, has no effect.

Figure 2:
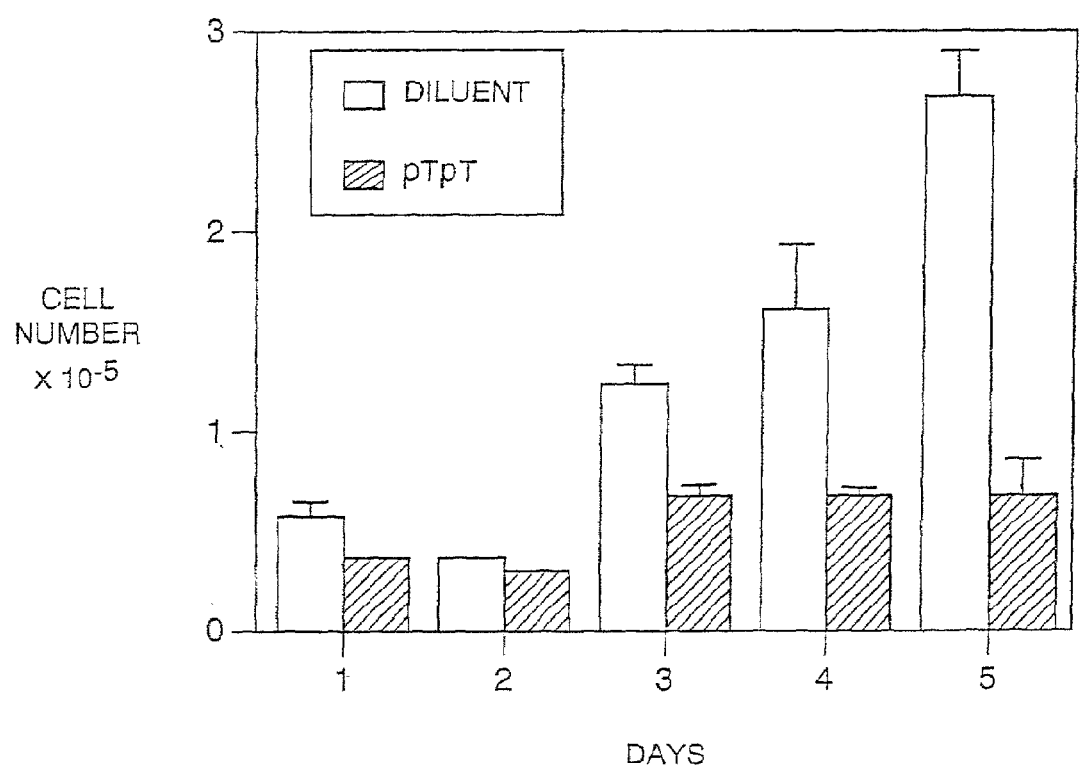
FIG. 2 is a graphic representation of the cell growth rate of normal human fibroblasts dosed with water (diluent) or 100 µM pTpT ($T_2$), where day 0 is before dosage and days 1, 3, 4 and 5 are days after dosage, and where values represent averages ± standard deviations of duplicate cultures.

In a second experiment, SCC12F cells were cultured as described above. Two or three days after seeding, the preconfluent cultures were given fresh medium supplemented with either 100 µM $T_2$ or diluent as a control. Cells were collected daily by trypsinization and counted by Coulter™ counter. The cell yield in cultures treated with $T_2$ was reduced by 75% compared to that of paired control cultures after five days (FIG. 2). This corresponds to 2.3 population doublings in this time for control cells, compared with 1 doubling for $T_2$-treated cells. These results further demonstrate that application of $T_2$ DNA fragments inhibits cell proliferation, including proliferation of cancerous cells.

In a third experiment, it was demonstrated that addition of $T_2$ to human squamous carcinoma cells for 24–72 hours resulted in upregulation of at least three genes: growth arrest and DNA damage (GADD 45), senescence-derived inhibitor (Sdi I), and excision repair cross-complementing (ERCC-3). Paired cultures of SCC12F cells were maintained in a Dulbecco's modified Eagle's Medium-based keratinocyte growth medium (DMEM; GIBCO/BRL, Gaithersburg, Md.) supplemented with 10% fetal calf serum (Hyclone Labs, Logan, Utah) and epidermal growth factor as described (Hollander, M. C. et al., *J. Biol. Chem.* 268:328–336 (1992)). Pre-confluent cultures were given fresh medium supplemented with either 100 µM $T_2$, or an equal volume of diluent. Cells were collected daily after additions, and processed for total RNA isolation using the Tri-Reagent extraction method (Molecular Research Center, Cincinnati, Ohio) following the protocol of the manufacturer. Ten micrograms of RNA from each sample was gel electrophoresed, transferred to a nylon filter and probed as described previously (Nada, A. et al., *Exp. Cell Res.* 211:90–98 (1994)). The cDNA for GADD 45 was generated by PCR using primers based on the human GADD 45 gene sequence (Mitsudomi, T. et al., *Oncogene* 7:171–180 (1992)). The cDNA for ERCC 3 was purchased from the American Type Culture Collection (ATCC, Rockville, Md.). The SDI 1 cDNA was a gift of Dr. J. Smith and has been described previously (Walworth, N.C. and Bernards, R., *Science* 271: 353–356 (1996)).

Compared to the diluent control, the mRNAs for GADD 45, ERCC 3 and SDI 1 were up-regulated in $T_2$-treated cells as early as 24 hours, and remained elevated for several days. Addition of the control $A_2$ was less effective or ineffective in inducing these genes. Comparable data have been obtained in experiments with S91 melanoma cells, and normal human fibroblasts.

The time course of induction is similar to that observed after UV irradiation for the two genes for which this has been studied [GADD 45 and p21 (also called Sdi I)] and also similar to the time course of induction of the tyrosinase gene by $T_2$ in melanocytes and melanoma cells. Sdi I is known to be involved in cell cycle regulation and specifically in blocking cell division. GADD 45 and ERCC-3, a human DNA repair enzyme, are known to be involved in repair of UV-induced DNA damage. The response to $T_2$ is identical to that observed after UV irradiation of these cell lines, and is also similar to the response to various antimetabolites, such as methotrexate, that are clinically effective in the treatment of hyperproliferative skin disorders.

Example 2

Application to Human Cervical Carcinoma Cells

Human cervical carcinoma cells (HeLa cells) were maintained in DME+10% calf serum and dosed with either water (diluent) or 100 µM $T_2$. Cells were collected 1, 4 and 6 days after dosage and counted by Coulter™ counter.

Figure 3:
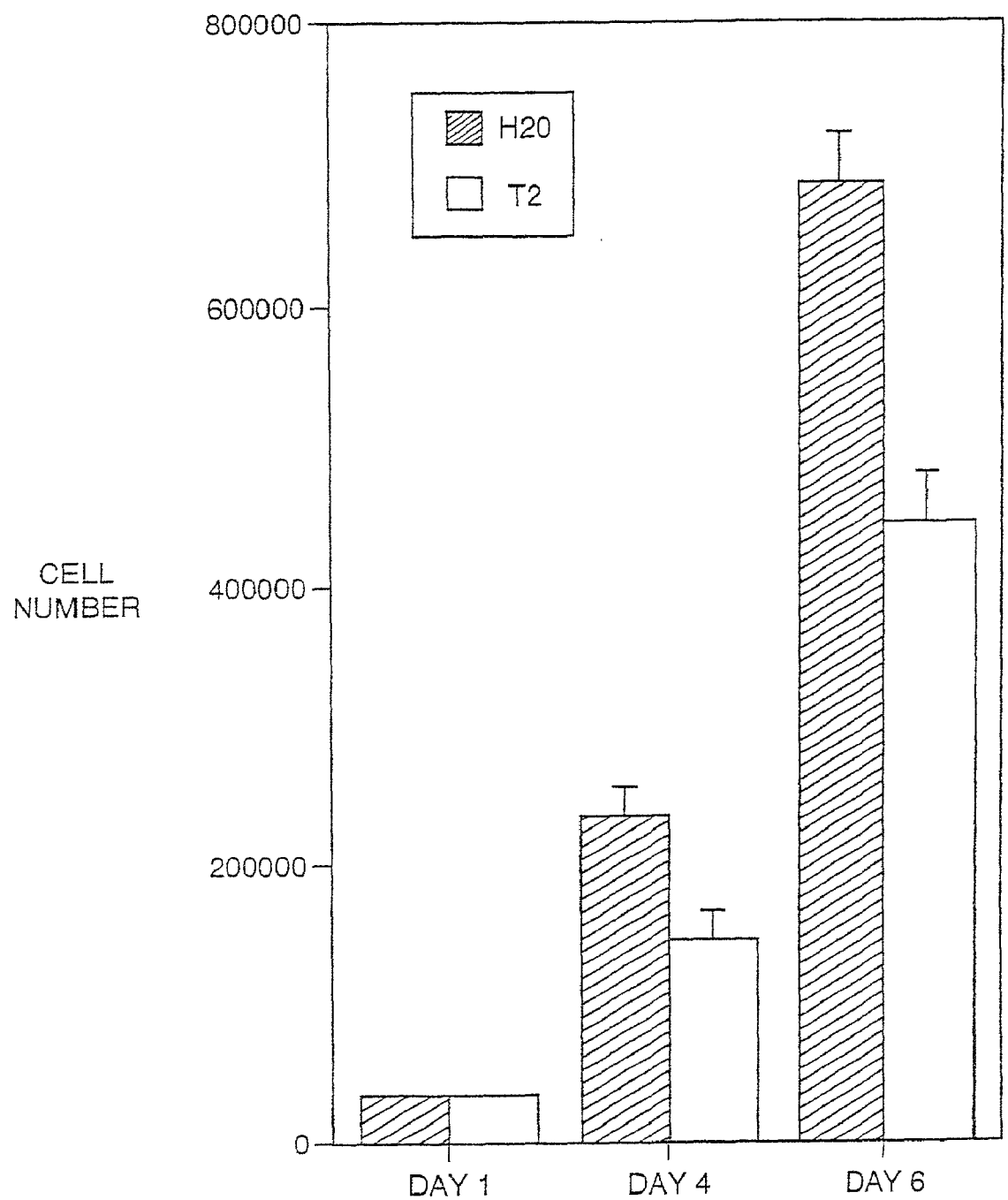
FIG. 3 is a graphic representation of the cell growth rate of human cervical carcinoma cells dosed with either water (diluent) or 100 µM pTpT ($T_2$), where day 0 is before dosage and days 1, 4 and 6 are days after dosage.

Addition of $T_2$ to the human cervical carcinoma cells resulted in marked decreases in cell growth rate, as shown in FIG. 3.

Example 3

Application to Human Melanoma Cells

Human melanoma cell lines CRL 1424, Malma, Sk Mel 2, and Sk Mel 28 were obtained from the American Type Culture Collection (ATCC). The cell lines were maintained in DME+2% calf serum, and dosed with either water (diluent) with DME, or 100 µM $T_2$ in DME. One week after dosage, cells were collected and counted by Coulter™ counter.

Figure 4:
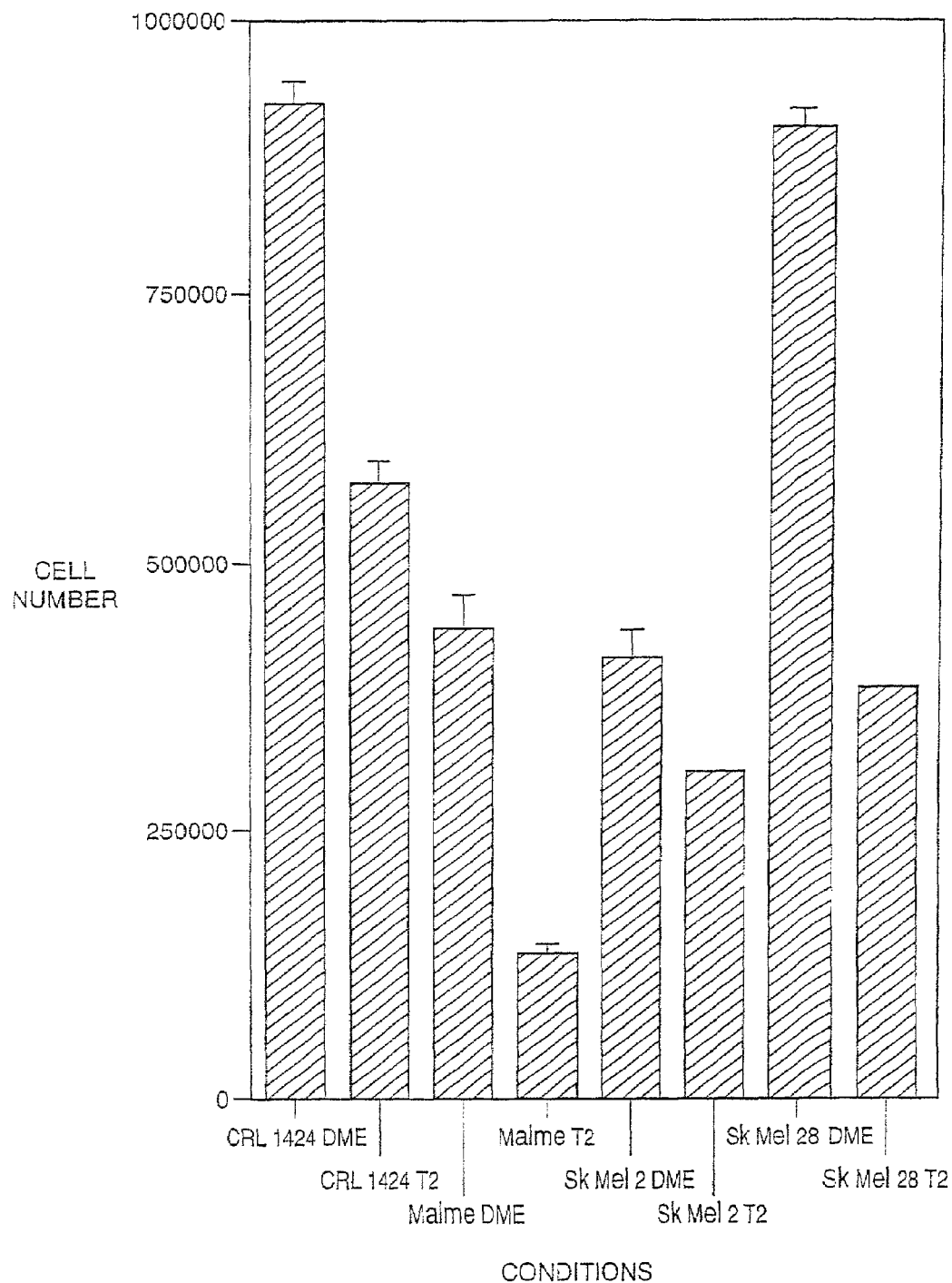
FIG. 4 is a graphic representation of the cell yield of human melanoma cell lines dosed with either diluent or 100 µM pTpT ($T_2$).

Addition of $T_2$ to any of the four different human melanoma cell lines results in marked decreases in cell yields, as shown in FIG. 4.

Example 4

Application to Human Keratinocytes

Figure 5:
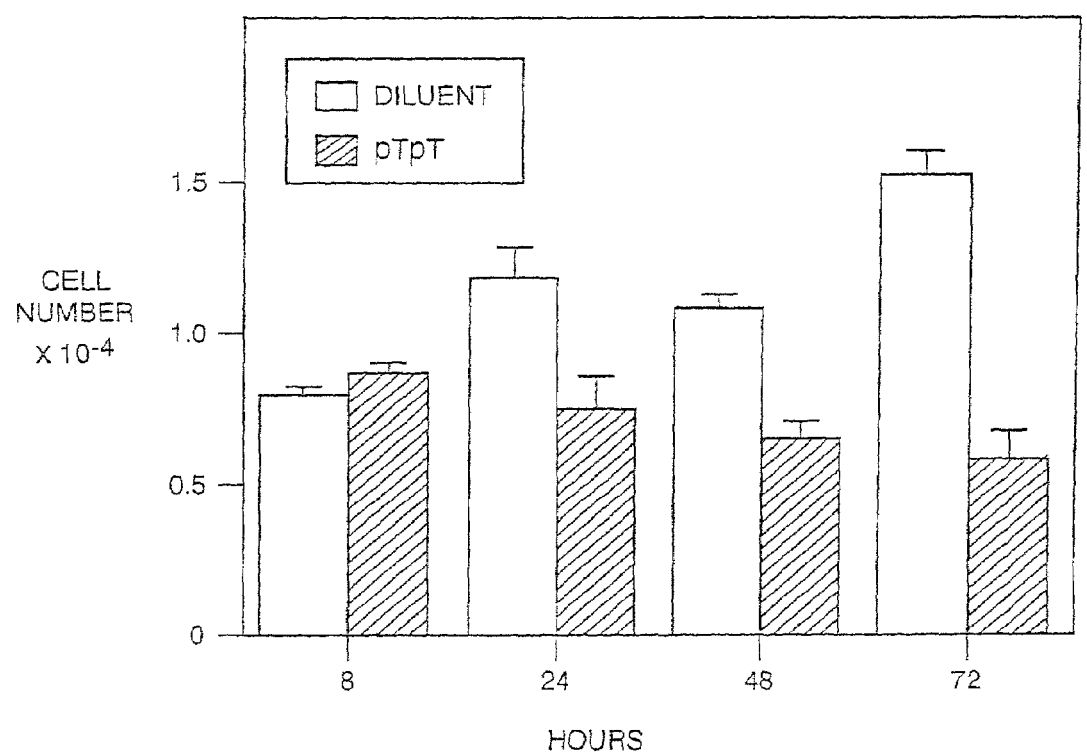
FIG. 5 is a graphic representation of the cell growth rate of normal human keratinocytes dosed with water (diluent) or 100 µM pTpT ($T_2$), where day 0 is before dosage and 8, 24, 48 and 72 are hours after dosage and where values represent averages ± standard deviations of duplicate cultures.

Normal human neonatal keratinocyte cells were cultured as described above in Example 1 for SCC12F cells, and treated with either 100 µM $T_2$ or diluent as a control. Cells were harvested for cell counts. The cell yield in cultures treated with $T_2$ was reduced by 63% compared to that of paired control cultures after three days (FIG. 5). This corresponds to one population doubling in this time for control cells, while the number of $T_2$-treated cells remained the same. These results demonstrate that application of the DNA fragments inhibits cell proliferation.

Northern blot analysis of the normal human keratinocytes treated with $T_2$ for 24–72 hours that showed induction of the tumor necrosis factor alpha gene (TNFα). This immunomodulatory cytokine, known to be induced by UV irradiation, may thus be induced by $T_2$. Use of locally applied DNA fragments, deoxynucleotides, dinucleotides, or dinucleotide dimers is useful in immunomodulation of cutaneous reactions and in treatment or prevention of diseases or conditions involving immune mediators.

Example 5

Inhibition of Cell Growth of Normal Neonatal Fibroblasts by DNA Fragments

Figure 6:
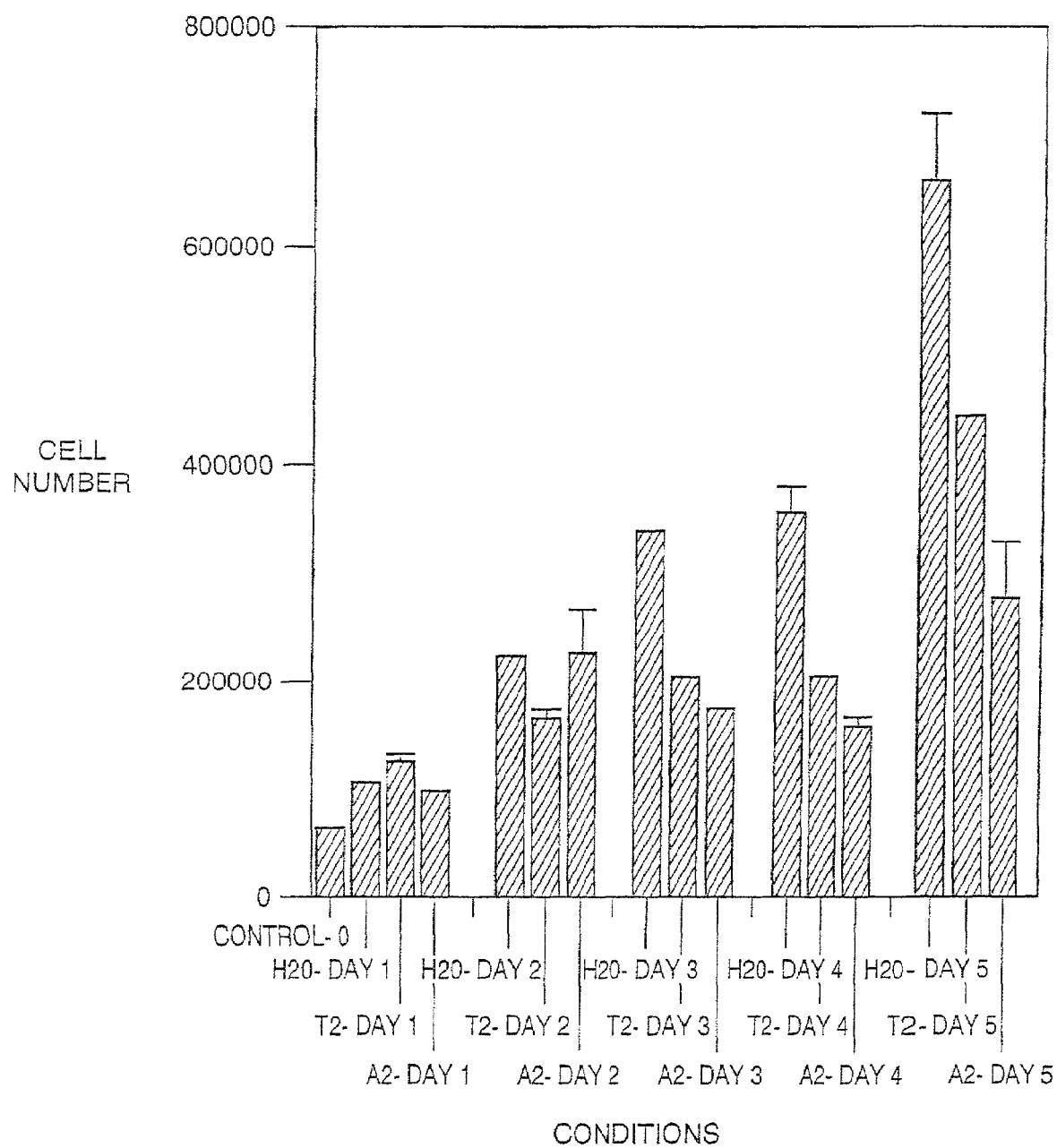
FIG. 6 is a graphic representation of the average cell number of human neonatal fibroblasts dosed with either water, $T_2$ or $A_2$.
Figure 7:
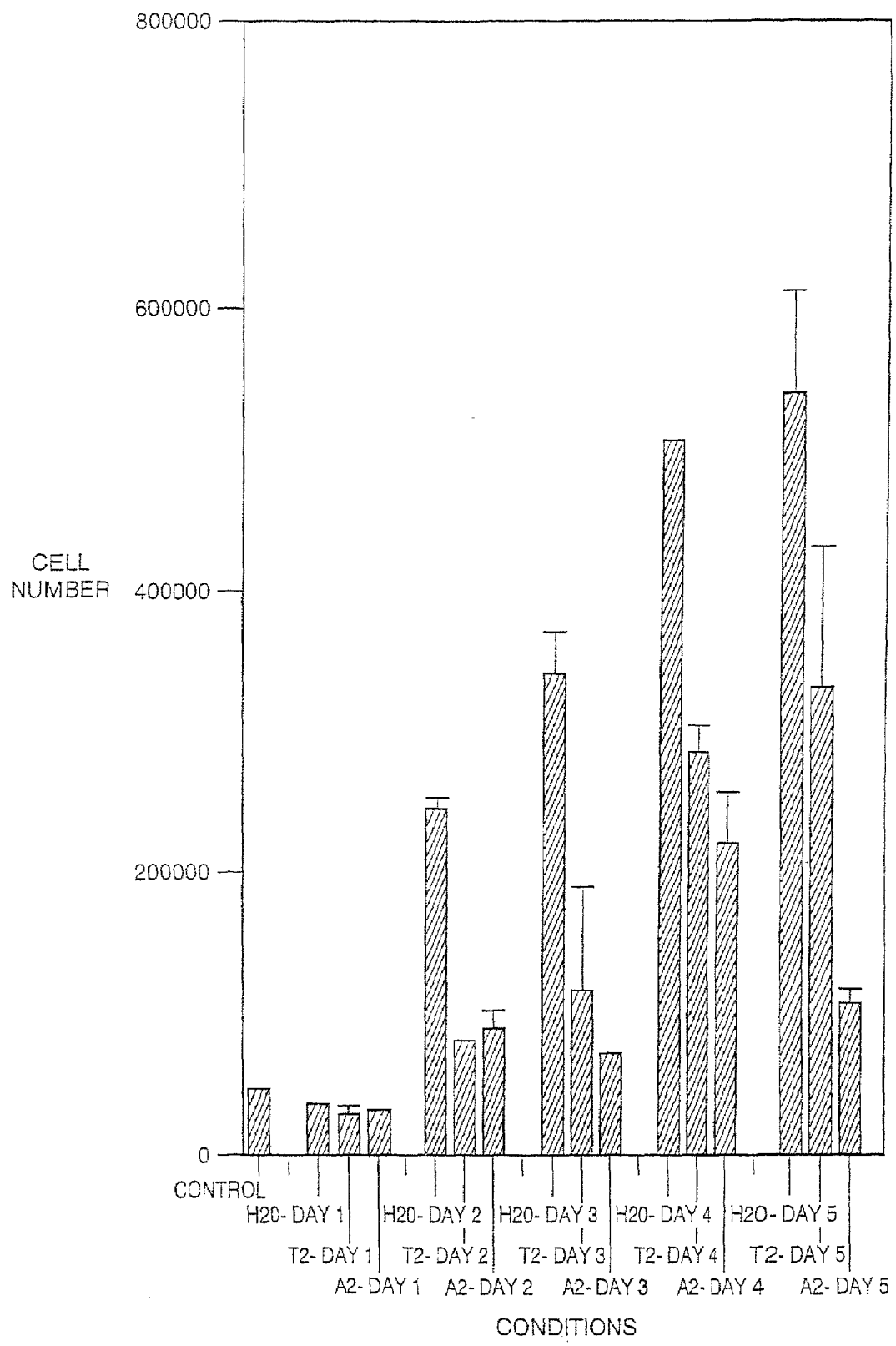
FIG. 7 is a graphic representation of the average cell number of human neonatal fibroblasts dosed with either water, $T_2$ or $A_2$.

Normal human neonatal fibroblasts were plated in Falcon P35 culture dishes at a density of $9 \times 10^4$ cells/dish. The culture medium was DME+10% calf serum, 2 ml per plate. One day after plating, cultures were supplemented with either 100 μM T$_2$ in DME or 100 μM A$_2$ in DME, or water (control). Two plates were collected and counted before the additions to give a starting, or "day 0," reading. Duplicate plates of each condition were harvested through five days after addition of the supplements and cell number determined. All cell counts were done by Coulter™ Counter. Results of two experiments, are shown in FIGS. 6 and 7. The results indicate that application of the DNA fragments inhibits cell proliferation.

Figure 8:
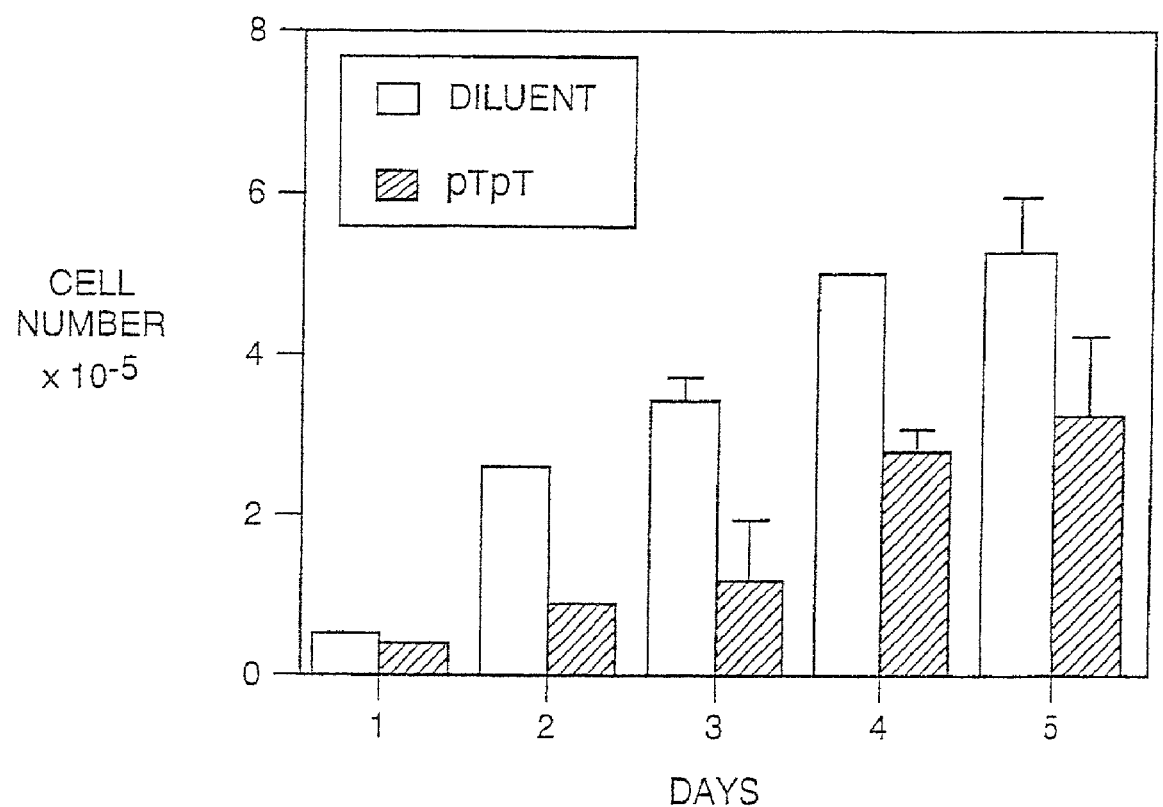
FIG. 8 is a graphic representation of the cell growth rate of normal human fibroblasts dosed with water (diluent) or 100 µM pTpT ($T_2$), where day 0 is before dosage and where values represent averages ± standard deviations of duplicate cultures.

In a second experiment, normal human neonatal fibroblasts were plated and cultured, as described above in Example 1 for SCC12F cells. Cultures were supplemented with either 100 μM T$_2$ or water (control), and cells were harvested for cell counts. The cell yield in fibroblast cultures treated with T$_2$ was reduced by 40% compared to that of paired control cultures after three days (FIG. 8). This corresponds to 4 population doublings in this time for control cells, compared with 3.6 doublings for T$_2$-treated cells. These results further demonstrate that contacting cells of interest with the DNA fragments of the present invention inhibits cell proliferation.

Example 6

Effect of pTpT Applications on Epidermal Cell Proliferation

Guinea pigs received one or two daily topical applications of 100 μM pTpT, or vehicle alone as control, for three days. On the fourth day, punch biopsies were obtained and maintained for 7 or 8 hours in primary keratinocyte medium supplemented with 10 μCi/ml $^3$H-thymidine (specific activity 9.0 Ci/m mole, NEN). Proliferating cells are expected to incorporate the $^3$H-thymidine into newly synthesized DNA. Tissues were then rinsed with cold medium and fixed in 10% phosphate buffered formalin. After a series of dehydration steps, tissues were embedded in paraffin. 6 μm sections were cut and mounted onto glass slides, dipped in NTB-2 Nuclear Track emulsion and kept in the dark at 4° C. for 7 days. Sections were developed in Kodak D-19 developer and stained with hematoxylin and eosin. Labeling index, a measure of DNA replication and therefore cell proliferation, was measured by calculating the percentage of labeled nuclei among 100 basal keratinocytes. Results are shown in Table 1.

TABLE 1

| Labeling Index | |
|---|---|
| Vehicle control | pTpT |
| 2 daily applications | |
| 4 ± 1.4 | 1.5 ± 0.7 |
| 1 daily application | |
| 4.5 ± 2.1 | 2 ± 0 |

Mean values ± SD are shown.
Labeling index (a measure of epidermal cell proliferation) is less in pTpT-treated skin than in vehicle-treated skin, (p < 0.03 paired T test) in both experiments. These results demonstrate that contacting cells of interest with the DNA fragments of the present invention inhibits cell proliferation.

Example 7

Role of p53 in DNA Repair

Figure 9:
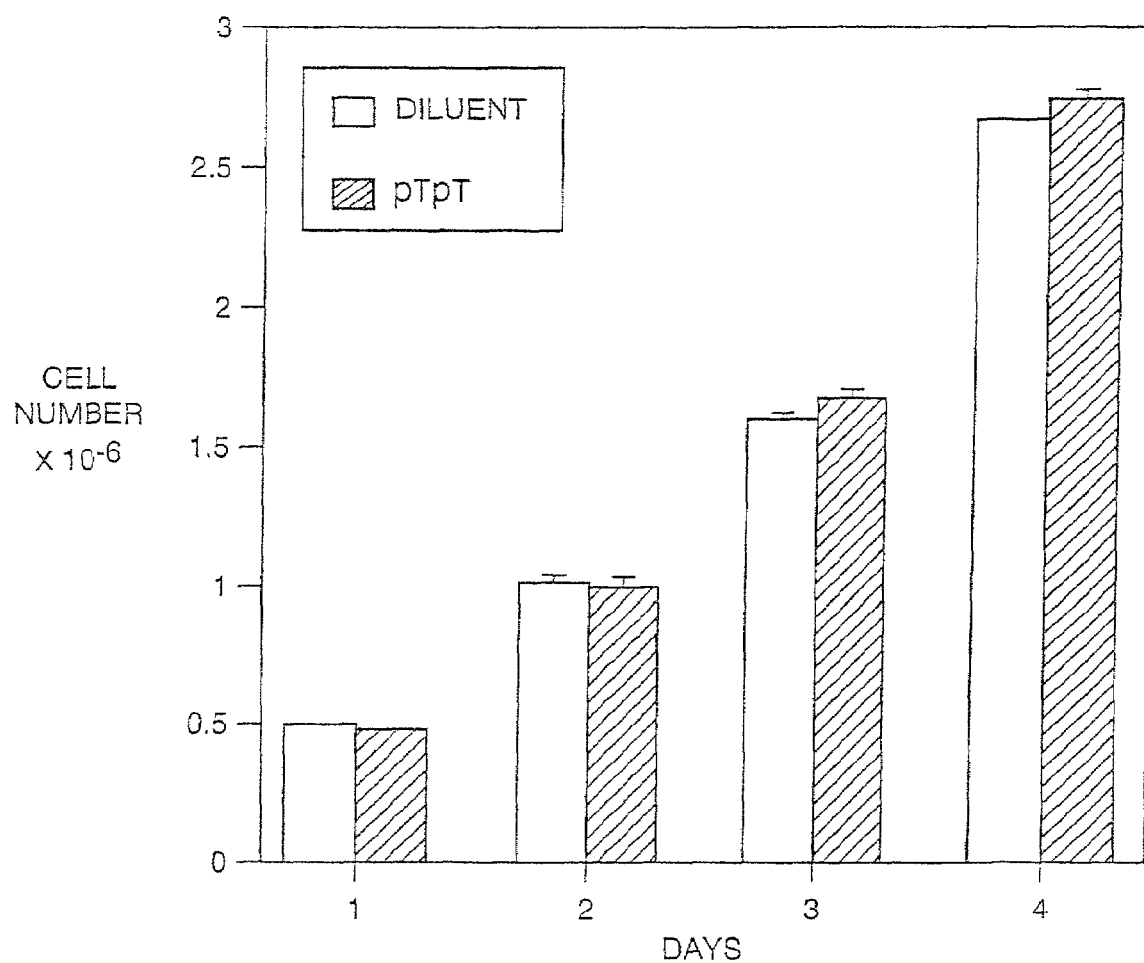
FIG. 9 is a graphic representation of the cell growth rate of p53-null H1299 lung carcinoma cells dosed with water (diluent) or 100 µM pTpT ($T_2$), where day 0 is before dosage and 1, 2, 3 and 4 are days after dosage, and where values represent averages ± standard deviations of duplicate cultures.

Both the GADD 45 and SDI 1 genes are known to be transcriptionally regulated by the tumor suppressor protein p53. After UV- and γ-irradiation, as well as treatment of cells with DNA-damaging chemical agents, there is a rapid stabilization, phosphorylation and nuclear accumulation of p53 after which this protein binds to specific promoter consensus sequences and modulates the transcription of regulated genes. Recent data suggest that p53 can also be activated by the binding of small single-stranded DNAs, as well as certain peptides and antibodies, to a carboxyl terminal domain of this protein. In order to determine whether the inhibitory effect of the dinucleotide pTpT on cell proliferation is mediated in part through p53, the growth response of a p53 null cell line, H1299 lung carcinoma cells, was examined. The p53-null H1299 cells (Sanchez, Y. et al., *Science* 271:357–360 (1996)) were maintained in DMEM with 10% calf serum. Preconfluent cultures were given fresh medium supplemented with either 100 μM pTpT or diluent. Cells were collected on consecutive days by trypsinization, and counted by Coulter™ counter. As shown in FIG. 9, there was no inhibition of proliferation of pTpT-treated H1299 cells compared to diluent-treated controls.

In another experiment, pTpT was found to induce the expression of SDI 1 mRNA in a p53-dependent manner. Preconfluent cultures of H1299 cells were transfected with an expression vector containing the wild type human p53 cDNA under the control of the human cytomegalovirus promoter/enhancer (Dr. Bert Vogelstein, Johns Hopkins Oncology Center). Control transfections were performed using the vector from which the p53 cDNA was removed. Transfections were carried out using the Lipofectin Reagent Kit (GIBCO/BRL). One day after transfection, cells were collected for Western blot analysis using 20 μg total protein as described (Yaar, M. et al., *J. Clin. Invest.* 94:1550–1562 (1994)). p53 was detected using mAb 421, anti-mouse Ig linked to horseradish peroxidase (Amersham, Arlington Heights, Ill.) and an ECL-kit (Amersham), following the directions of the manufacturer. At the time of protein collection, duplicate cultures of H1299 cells transfected with the p53 expression vector (designated "p53") or control vector ("Ctrl") were given either diluent (DMEM) or 100 μM pTpT. After 24 hours, the cells were collected, processed for RNA isolation and Northern blot analysis with an SDI 1 cDNA probe. The autoradiograph was scanned using a Macintosh IIsi computer and Macintosh One Scanner, and the brightness and contrast were adjusted to display differences in autoradiographic signals maximally. The results indicated that p53-null H1299 cells express a very low level of the SDI 1 transcript and this level is not affected by addition of pTpT. Transfection of these cells with a wild-type p53 expression vector increased the level of SDI 1 and rendered this transcript inducible by addition of pTpT. Western analysis confirmed that H1299 cells normally express no p53 and that transfected H1299 cells expressed high levels of p53. These data indicate that pTpT increases the transcriptional activity of p53.

The effect of pTpT on the level and intracellular distribution of p53 in normal neonatal fibroblasts was examined by immunoperoxidase staining using a p53-specific monoclonal antibody (mAb 421, Oncogene, Cambridge, Mass.). Preconfluent cultures were treated with either 100 μM pTpT or diluent for 24 hours before cell staining. Cells were first fixed for one minute in Histochoice fixative (Amresco, Solon, Ohio) followed by a five-minute rinse in PBS. p53 was detected using the Vectastain Elite ABC kit (Vector Laboratories, Burlingame, Calif.) and the p53-specific monoclonal antibody mAb 421. Within 24 hours, an increase in intranuclear p53 was detected in pTpT-treated cells compared to diluent-treated cells, as has been reported after UV-irradiation. These results are consistent with the induction of the p53-regulated genes GADD 45 and SDI1 (p21) in fibroblasts as well as in SCC12F cells, by pTpT.

Example 8

Enhancement of DNA Repair

Expression of a UV-damaged reporter plasmid containing the bacterial chloramphenicol acetyltransferase (CAT) gene under the control of SV40 promoter and enhancer sequences was previously shown to detect decreased DNA repair capacity in human lymphocytes associated with aging and early-onset skin cancers. This reporter plasmid was used to measure the DNA repair capacity of normal neonatal human skin-derived fibroblasts and keratinocytes.

Keratinocytes from newborns were established as described (Stanulis-Praeger, B. M. and Gilchrest, B. A., *J. Cell. Physiol.* 139:116–124 (1989)) using a modification of the method of Rheinwald and Green (Gilchrest, B. A. et al., *J. Invest. Dermatol.* 101:666–672 (1993)). First-passage keratinocytes were maintained in a non-differentiating low $Ca^{2+}$ medium (K-Stim, Collaborative Biomedical Products, Bedford, Mass.). Fibroblasts were established from dermal explants as described (Rheinwald, J. G. and Green, J., *Cell* 6:331–343 (1975)) and maintained in DMEM supplemented with 10% bovine serum. Cells were treated with either 100 µM pTpT or an equal volume of diluent (DMEM) for five days prior to transfection. Duplicate cultures kept under each condition were transfected using the Lipofectin Reagent Kit (GIBCO/BRL) and 5 µg reporter DNA, pCAT-control vector (Promega, Madison, Wis.). Before transfection, the vector DNA was either sham irradiated or exposed to 100 mJ/cm² UVB radiation from a 1 KW Xenon arc solar simulator (XMN 1000-21, Optical Radiation, Azuza, Calif.) metered at 285±5 nm using a research radiometer (model IL 1700A, International Light, Newburyport, Mass.), as described (Yaar, M. et al., *J. Invest. Dermatol.* 85:70–74 (1985)). Cells were collected 24 hours after transfection in a lysis buffer provided in the CAT Enzyme Assay System (Promega, Madison, Wis.) using a protocol provided by the manufacturer. CAT enzyme activity was determined using the liquid scintillation counting protocol and components of the assay system kit. Labeled chloramphenicol [50–60 mCl (1.85–2.22 GBq) mmol] was purchased from New England Nuclear (Boston, Mass.). Protein concentration in the cell extracts was determined by the method of Bradford (Anal. Biochem. 72:248 (1986)). CAT activity was expressed as c.p.m./100 µg protein and is represented as percent activity of cells transfected with sham-irradiated, non-damaged, plasmid.

Figure 10:
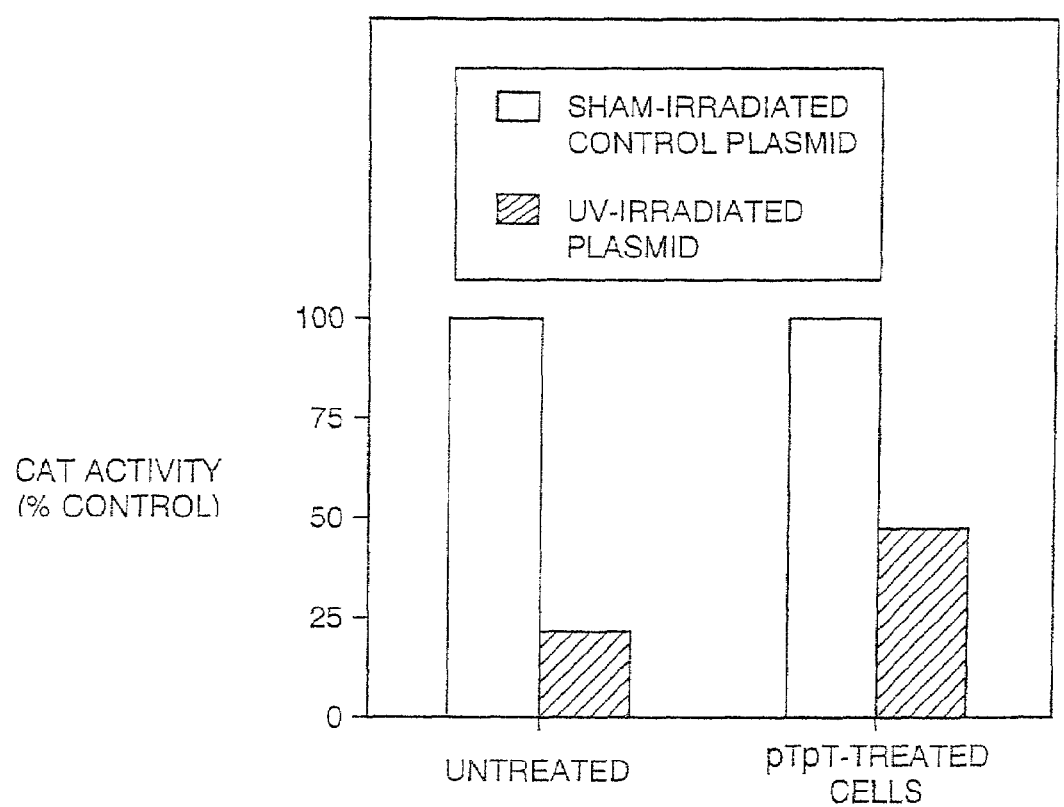
FIG. 10 is a graphic representation of enhancement of DNA repair of a reporter plasmid in human keratinocytes treated with pTpT, where open boxes represent sham-irradiated control plasmid and filled boxes represent UV-irradiated plasmid.
Figure 11:
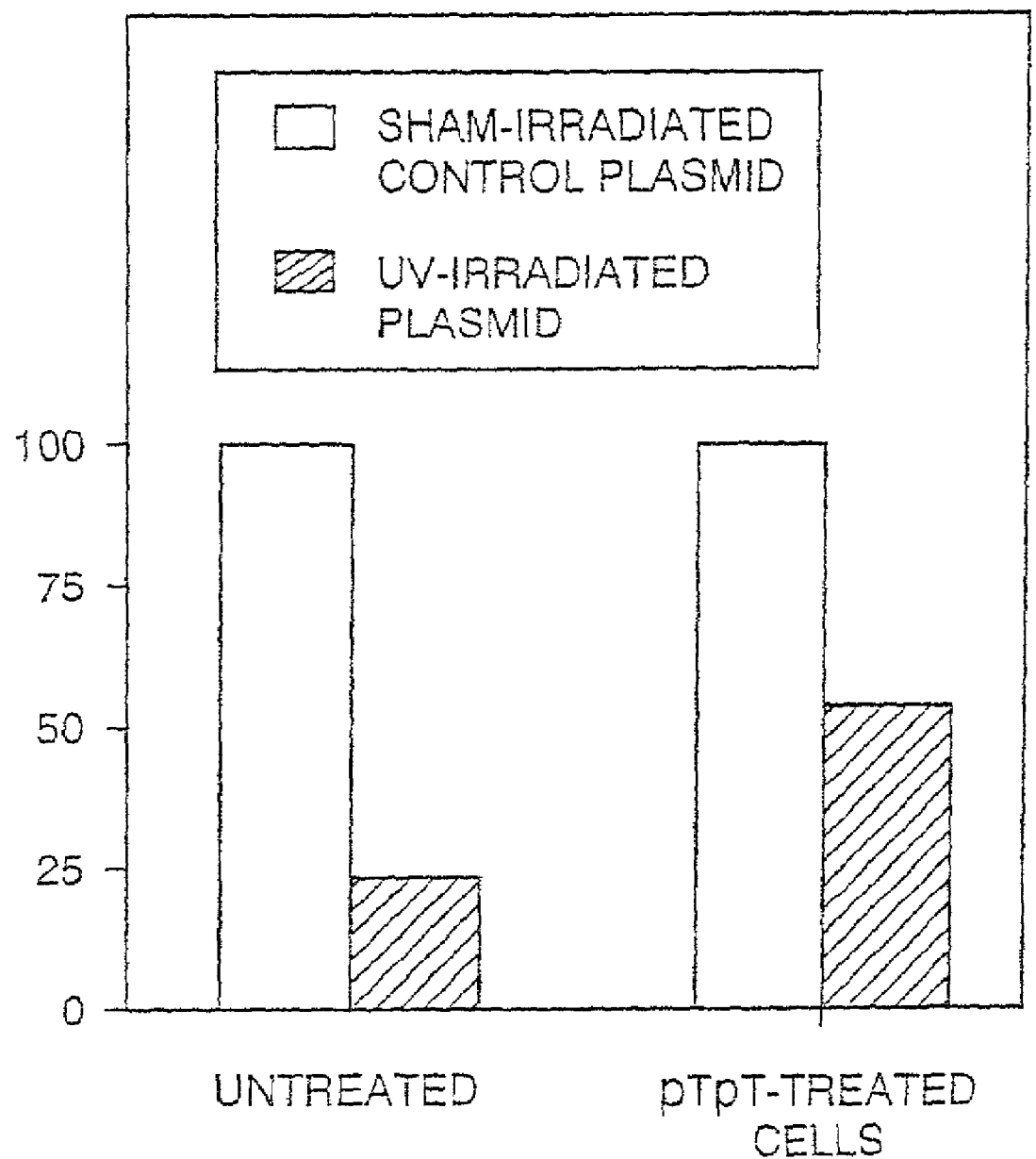
FIG. 11 is a graphic representation of enhancement of DNA repair of a reporter plasmid in human fibroblasts treated with pTpT where open boxes represent sham-irradiated control plasmid and filled boxes represent UV-irradiated plasmid.

In preliminary experiments, exposure of the plasmid to a dose of solar-simulated irradiation (100 mJ/cm², metered at 285 nm) prior to transfection was identified as resulting in approximately 75% reduction in CAT activity assayed in cell lysates 16–24 hours after transfection, compared to that of sham-irradiated plasmid transfected into paired cultures. However, keratinocytes (FIG. 10) and fibroblasts (FIG. 11) pretreated with 100 µM pTpT for five days before transfection displayed CAT activity more than 50% that of sham-irradiated transfected controls. Because the reporter plasmid was nonreplicating, the level of CAT activity directly reflects the degree of DNA repair of the UV-damaged CAT gene restoring its biological activity. These data indicate that pTpT treatment of normal human fibroblasts and keratinocytes more than doubles the capacity of cells to repair UV-induced DNA damage over a 24 hour period. The enhanced expression of UV-irradiated plasmid in pTpT-treated cells did not result from a general increase in plasmid transcription in these cells, because the expression of the sham-irradiated plasmid was not higher in non-pTpT-treated cells.

Example 9

Activation of p53 and Repair of Benzo[a]pyrene DNA Adducts

Cell Culture.

Newborn human keratinocytes were established using a modification (Stanislus et al. *J. Invest. Dermatol.* 90:749–754 (1998)) of the method of Rheinwald and Green (*Cell* 6:331–343 (1975)). First-passage keratinocytes were maintained in a non-differentiating medium containing a low concentration of calcium ion (K-Stim, Collaborative Biomedical Products, Bedford, Mass.).

The p53-null H1299 lung carcinoma cell line (American Type Culture Collection, ATCC, Rockville, Md.) was maintained in Dulbecco's modified Eagle's medium (DMEM; GIBCO/BRL, Gaithersburg, Md.) supplemented with 10% bovine serum (Hyclone Labs, Logan, Utah).

Transfection of H1299 Cells with a p53 Expression Vector.

Preconfluent cultures of H1299 cells were transfected with an expression vector containing the wild type human p53 cDNA under the control of the human cytomegalovirus promoter/enhancer (Dr. Bert Vogelstein, Johns Hopkins Oncology Center). Control transfections were performed using the same vector lacking the p53 cDNA. Transfections were carried out as described previously. One day after transfection, cells were collected for western blot using 20 µg total protein as described. p53 was detected using the monoclonal antibody DO-1 (Ab-6) known to detect both active and inactive forms of the protein (Oncogene, Cambridge, Mass.), anti-mouse Ig linked to horseradish peroxidase (Amersham, Arlington Heights, Ill.) and an ECL-kit (Amersham) following the direction of the manufacturer.

p53 Assay Using hGH Reporter Plasmid.

Normal human keratinocytes were transfected with the human growth hormone (hGH) reporter plasmid (pPG-GH) using the Lipofectamine Reagent Kit (GIBCO/BRL) as suggested by the manufacturer and 0.5 µg pPG-GH added to each p35 culture dish. pPG-GH contains the hGH coding region under the control of the thymidine kinase (TK) promoter and p53 consensus sequence, and hGH protein production is known to be proportional to p53 activity (Kern et al., 1992). Transfection was performed in the presence of 100 µM pTpT (Midland Certified Reagent Company, Midland, Tex.) or an equal volume of diluent. At the same time, the PSV-β-galactosidase control vector (Promega, Madison, Wis.) was co-transfected to determine the transfection efficiency (Norton and Coffin, 1985). Four hours after transfection, the medium was removed and replaced with K-Stim medium with or without 100 µM pTpT. Twenty-four hours after transfection and pTpT treatment, 400 µl of the medium was harvested from each 35 mm culture dish, and 100 µl of $^{125}$I-hGH antibody solution (Nichols Institute Diagnostics, San Juan Capistrano, Calif.) was added to detect secreted hGH as described below. The cells were harvested in a Reporter Lysis Buffer (Promega) using a protocol provided by the manufacturer, and 150 µl of this lysate was used for the β-galactosidase assay using a β-galactosidase assay kit (Promega). Samples from each of triplicate culture dishes were evaluated for hGH and β-galactosidase synthesis.

H1299 cells were similarly transfected with p53 expression vector or control vector. Two days after the transfection these cells were cotransfected with pPG-GH and PSV-β-galactosidase control vector, and treated with 100 µM pTpT. Twenty-four hours later, 250 µl of the medium and the cell lysate were harvested and processed as described above.

CAT Assay.

The pCAT vector (Promega) was treated with benzo[a]pyrene-7,8-diol-9,10-epoxide (BP) as described (Athas et al. *Cancer Res* 1991) to produce less damaged and more damaged plasmids, previously shown to be instructive in studies examining different repair capacities in human cells. Based on the incorporation of $^3$H-BPDE into the DNA, the less damaged plasmid contained 25 adducts per 5 kb plasmid and the more damaged plasmid contained 50 adducts. This non-replicating vector contains the chloramphenicol acetyltransferase gene under control of SV40 promoter and enhancer sequences. Human keratinocytes and p53-transfected H1299 cells were pre-treated with either 100 µM pTpT or an equal volume of diluent (DMEM) alone for 48 hours, then transfected with either BP-modified pCAT-control vector (0.5 µg/ml) or unmodified vector (0.5 µg/ml) together with PSV-β-galactosidase control vector (0.5 µg/ml). Cells were collected in a reporter lysis buffer (Promega) 24 hours after transfection. CAT enzyme activity was determined using the liquid scintillation counting protocol and components of the assay system kit (Promega). $^{14}$C-labeled chloramphenicol[50–60 mCi(1.85–2.22 GBq)/mmol] was purchased from New England Nuclear (Boston, Mass.). CAT activity was normalized with β-galactosidase activity.

Western Blot Analysis.

Cells were treated with 100 µM pTpT or an equal volume of diluent alone for 48 hours. Total cellular proteins were collected in a buffer consisting of 0.25 M Tris HCl (pH 7.5), 0.375 M NaCl, 2.5% sodium deoxycholate, 1% Triton X-100, 25 mM MgCl$_2$, 1 mM phenylmethyl sulfonyl fluoride, and 0.1 mg ml aprotinin. Proteins (100 µg per sample) were separated by 7.5–15% SDS-PAGE and transferred to a nitrocellulose membrane (Schleicher & Schuell, Keene, N. H.). After transfer, the gel was stained with Coomassie Blue to verify even loading as visualized by the residual high molecular weight proteins. Membranes were blocked in 0.05% Tween-20/PBS with 5% milk, (Bio-Rad Laboratories, Hercules, Calif.). Antibody reactions were performed with the following antibodies: anti p53 (AB-6), anti PCNA (Ab-2) (Oncogene Science), and anti XPA (FL-273) (Santa Cruz Biotechnology). Sheep anti-mouse Ig linked to horseradish peroxidase (Amersham, Arlington Heights, Ill.) (for p53 and PCNA) and goat anti-rabbit IgG (Bio-Rad)(for XPA) were used as the secondary antibodies. Binding was detected by the ECL detection kit (Amersham).

To measure the repair of BP DNA adducts, non-replicating BP-damaged reporter plasmid system containing the bacterial chloramphenicol acetyltransferase (CAT) gene was used as described in Example 8. With first passage human keratinocytes, the transfection efficiency, as measured by the cotransfected β-galactosidase expression vector, was 40–70%. Compared to diluent-treated cells, pTpT-treated human keratinocytes showed an approximate doubling of CAT expression relative to paired cultures transfected with undamaged control CAT vector, when transfected with either the less BP-damaged (~25 adducts/plasmid) or the more BP-damaged (~50 adducts/plasmid) vector.

To confirm the activation of p53 by pTpT in a second assay, a reporter plasmid expressing the human growth hormone (hGH) gene under the influence of a p53 inducible promoter was employed. Activation of p53 increases its binding to the consensus sequence in the plasmid, leading to transcription of the hGH coding sequence and ultimately to secretion of hGH into the medium.

pTpT-treated human keratinocytes showed a 45%±25% increase in hGH secretion compared to diluent-treated cells. These data indicate that pTpT activates p53 in normal human keratinocytes as well as in p53-transfected H1299 cells.

To confirm that pTpT enhances repair of BP-DNA adducts, at least in part, through p53 activation, p53-null H1299 cells were transfected with the p53 expression vector, and p53 protein expression was then confirmed by western blot analysis 48 hours after transfection. In p53+H1299 cells, repair was comparable to that observed in normal keratinocytes; and the plasmid containing a low level of BP damage was repaired 80%±50% more efficiently in pTpT-pre-treated cells than in diluent pre-treated cells; and the plasmid containing a high level of BP damage was repaired more than three times as efficiently. In p53-H1299 cells, however, the repair capacity was the same as in both treatment groups. These data demonstrate that enhanced repair of BP-DNA adducts by pTpT involves p53.

pTpT activation of p53 in H1299 cells transiently transfected with the p53-responsive-hGH resulted in a 40% increase in hGH secretion compared to diluent-treated cells. These data further demonstrate that pTpT enhances p53 transcriptional activity through enhanced binding to its DNA consensus sequence.

Western blot analysis was used to examine the effect of pTpT treatment on the expression of selected genes known to be involved in DNA repair. Normal human keratinocytes were treated with pTpT for 2 days before harvesting cellular protein. pTpT up-regulated the levels of p53, PCNA and the XPA protein 2 to 3-fold within 2 days of treatment.

Example 10

Immunosuppression and Inhibition of Contact Hypersensitivity in a Murine Model

C57B16 mice were subjected to the following treatment prior to sensitization with the allergen DNFB, by topical administration to abdominal skin; no pretreatment, UVB irradiation (200 J/m$^2$/dx4d), pTpT, pApA, or vehicle alone (30 µl of 100 µM BID×5d). Mice pretreated with UVB or pTpT showed markedly suppressed ear swelling responses to DNFB challenge (0.6±0.2 and 0.9±0.3) compared to untreated or vehicle treated animals (4.3±0.6 and 3.3±0.2), whereas pApA-treated mice exhibited intermediate responses (2.5±0.6).

The immunomodulatory effect of pTpT was tested in vitro using human keratinocytes. Duplicate cultures of primary human keratinocytes were treated with pTpT, diluent or UVB irradiation (200 J/m$^2$) or sham irradiation. Cells were collected at various times after treatment and analyzed for IL-10 protein by ELISA and for IL-10 mRNA by RT-PCR. An increase in IL-10 mRNA was detected after 6 hours in irradiated cells and after 48 hours in pTpT treated cells. An increase in IL-10 protein of 18 pg/ml was detected 24 hours after irradiation and 15±2 pg/ml 72 hours after treatment with pTpT. Previous work has demonstrated functional inhibition of the allogenic mixed lymphocyte reaction (MLR) assay by IL-10. In the allogenic MLR, T cell activation is measured as lymphocyte proliferation, measured by $^3$H-thymidine incorporation. IL-10 activity of culture medium from the 72 hour pTpT sample was measured by addition of the >10 kD components (containing the 18 kD IL-10 protein). Reduction in T cell proliferation by 80±5% was demonstrated, compared to 8%±3 inhibition from diluent-treated control cultures. Thus, like UVB irradiation, pTpT induces IL-10 in human keratinocytes which is likely to cooperate with TNFα to inhibit contact hypersensitivity in pTpT treated skin.

In another experiment, TNF-α gene activation was measured by utilizing mice carrying a CAT reporter transgene bearing the entire TNFα promoter and 3'-untranslated region. Transgenic mice were subjected to the following treatment prior to skin assay for CAT expression: UVB irradiation (200–700 J/m$^2$), intracutaneous injection of pTpT (100 µM); lipopolysaccharide (LPS 1 µg/ml) as positive control, or vehicle alone. CAT activity was detected in skin treated with UVB, LPS, or pTpT (but not with vehicle alone).

Example 11

Oligonucleotide Dependent UV-Mimetic Activity: Melanogenesis and p21/Waf1/Cip1 Expression The induction of melanogenesis in Cloudman S91 mouse melanoma cells by a five-nucleotide oligomer CATAC (SEQ ID NO: 6) and a nine-nucleotide oligomer, GAGTATGAG (SEQ ID NO: 1) was examined. Duplicates of Cloudman S91 murine melanoma cells were incubated with either 100 µM oligo or an equal volume of diluent (H$_2$O) for 5 days. The cells were then collected, counted, and an equal number of cells were pelleted for melanin analysis. In three experiments, the pigment content after incubation with the 9-mer, 5-mer and pTpT increased 418%±267%, 61%±60% and 155%±60% of control levels, respectively. The 9-mer, but not the 5-mer, also stimulated melanogenesis in human melanocytes, producing a 51–62% increase after one week in culture. Variations of this oligonucleotide were evaluated: a scrambled 9-mer (TAGGAGGAT; SEQ ID NO: 2) and two truncated versions, a 7-mer (AGTATGA; SEQ ID NO: 3) and second 5-mer (GTATG; SEQ ID NO: 4). Both 9-mers were equally active, inducing a 800% increase in melanin content. The truncated versions (SEQ ID NOs: 3 and 4) were also active, inducing 640% and 670% increases, respectively. As with pTpT, SEQ ID NO: 1 (9-mer) oligonucleotide, but not SEQ ID NO: 6 (5-mer) induced the expression of the p21/Waf 1/Cip 1 gene within 48 hours in a squamous cell carcinoma line, increasing the level of this mRNA 200–300%, compared to a 100–150% increase from pTpT.

Together, these data show that the UV-mimetic activity of pTpT can be duplicated quite dramatically by other oligonucleotides.

Example 12

Melanogenesis

Figure 12:
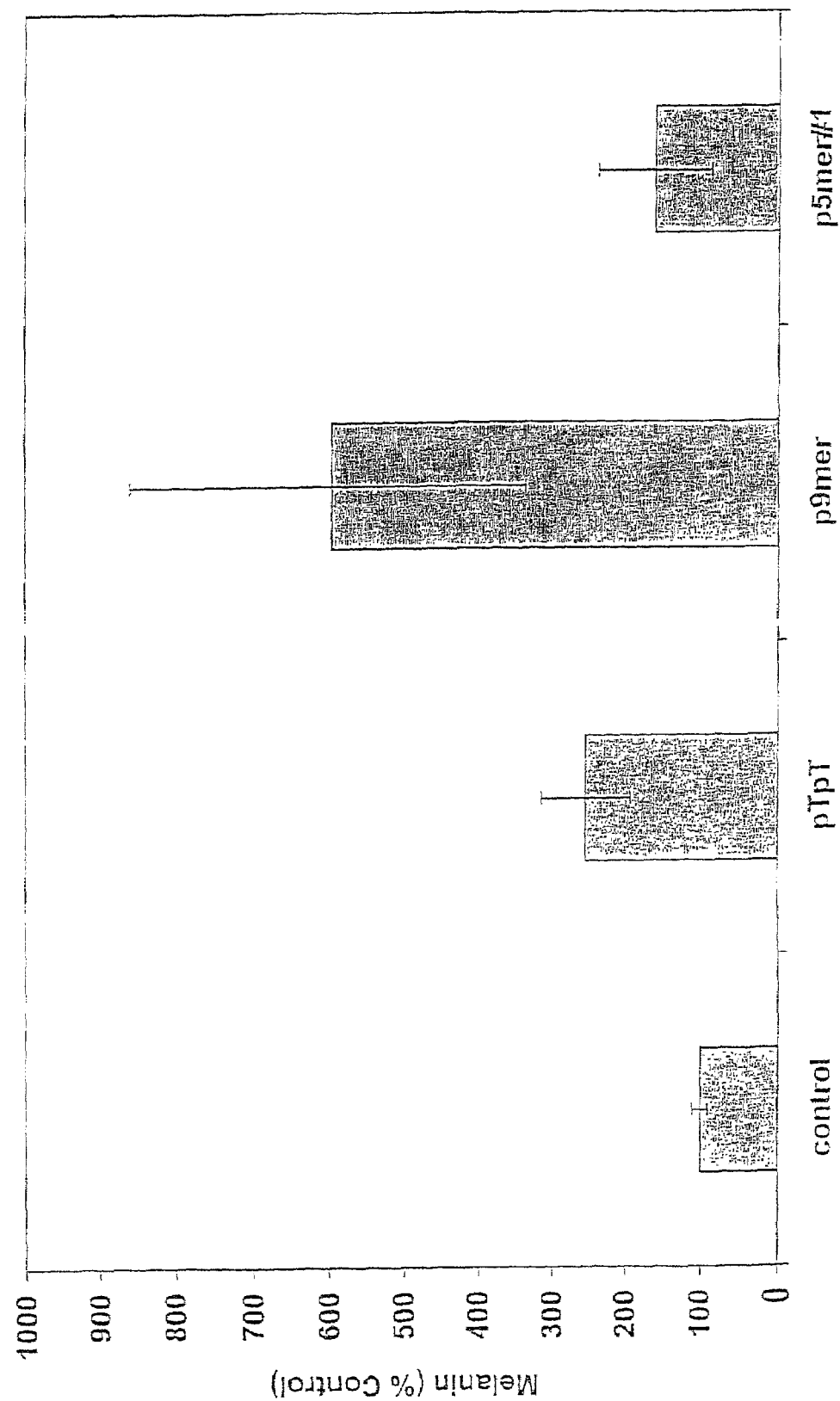
FIG. 12 is melanin content of Cloudman S91 cells treated with 100 µM of the indicated oligonucleotide or an equal volume of diluent for 5 days, where data are shown as averages of duplicate cultures calculated as a percentage of diluent-treated controls.

Cultures of Cloudman S91 murine melanoma cells were treated for 5 days with SEQ ID NO: 1, SEQ ID NO: 6, pTpT as a positive control, or an equal volume of diluent as a negative control. Spectrophotometric analysis of S91 cell pellets after oligonucleotide treatment showed the melanin content of pTpT-treated cells to be 255+/−60% that of control cells (FIG. 12). SEQ ID NO: 6 produced a slight increase in melanin, to 165+/−77% of control levels. SEQ ID NO: 1 stimulated melanin content to an average of 600+/−260% of control levels.

Figure 17:
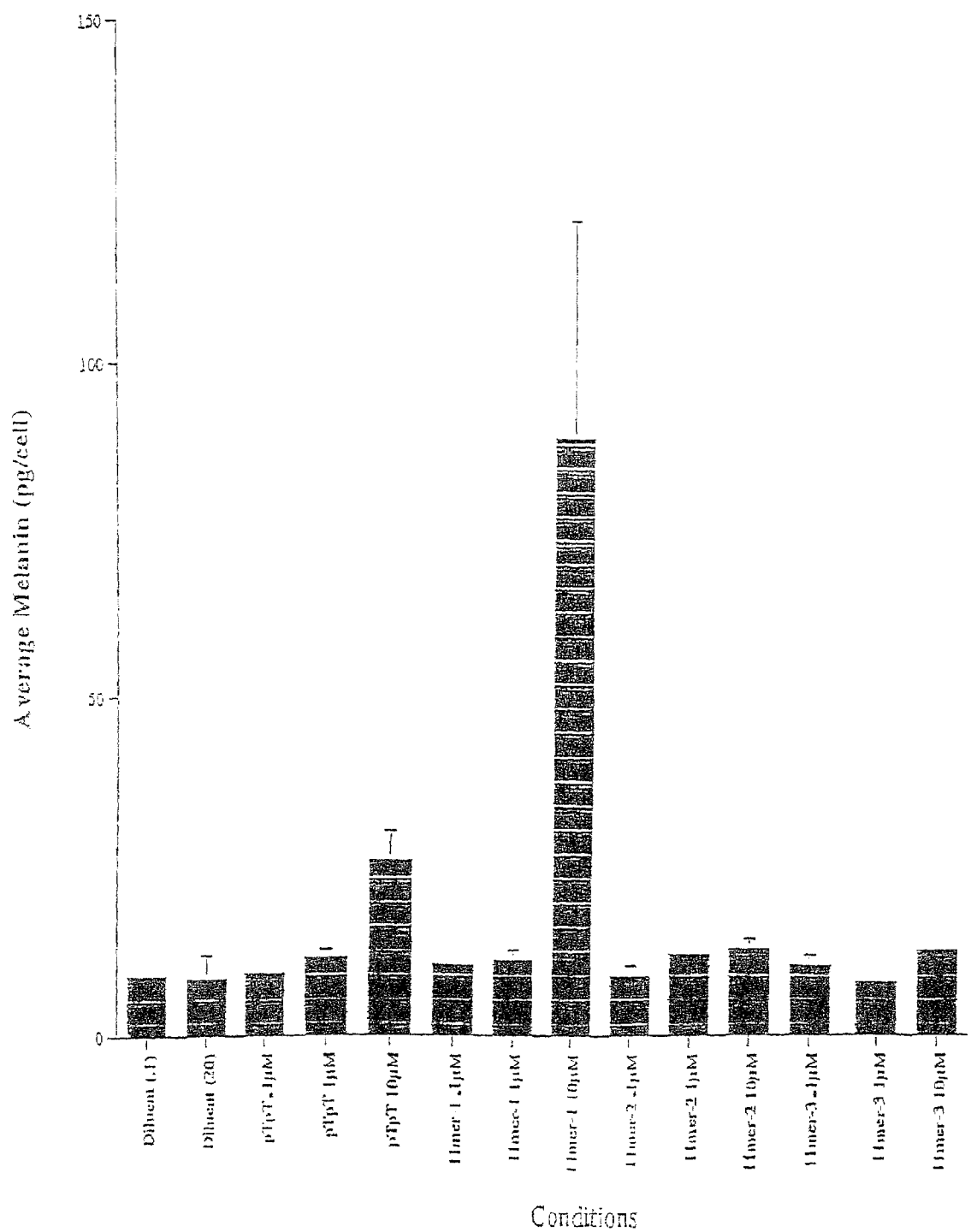
FIG. 17 shows melanin content of Cloudman S91 cells treated with the indicated oligonucleotide.
Figure 18:
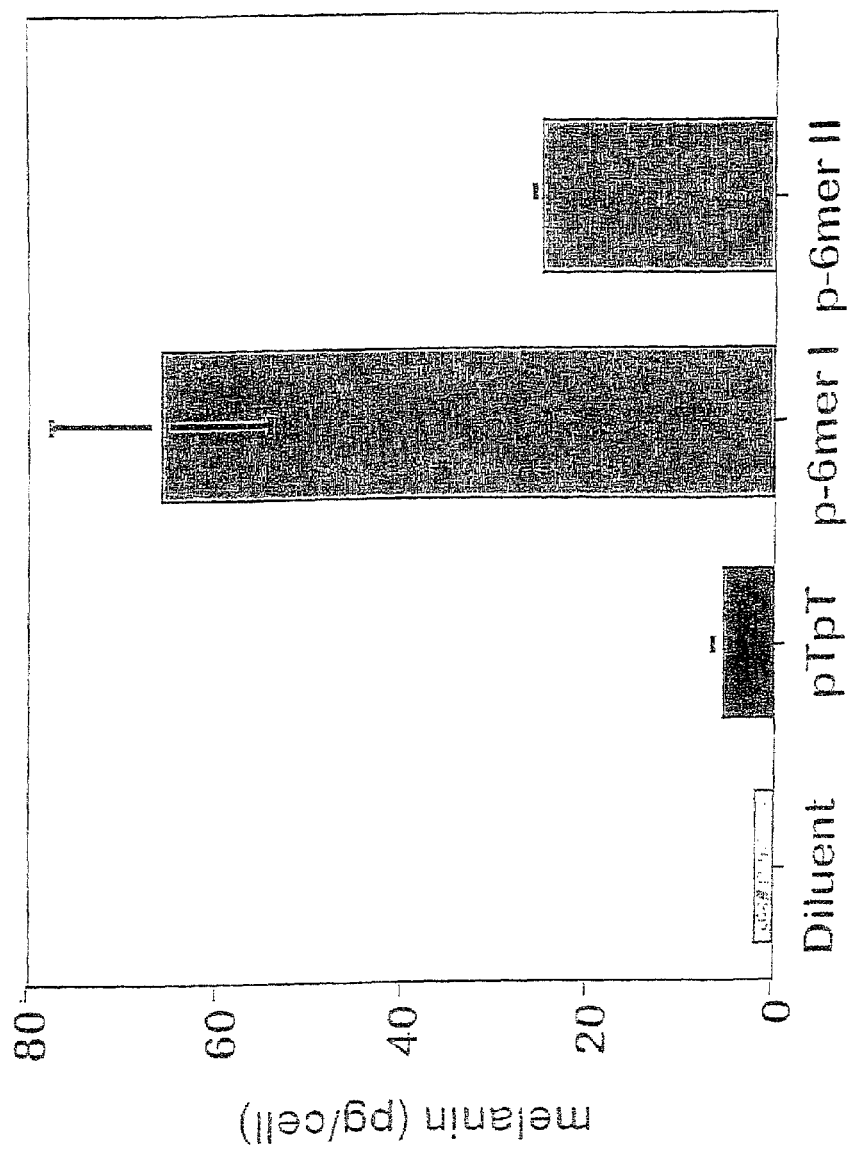
FIG. 18 shows melanin content of Cloudman S91 cells treated with the indicated oligonucleotide.

Oligonucleotides 5'pGTTAGGGTTAG3' (SEQ ID NO: 5), 5'pCTAACCCTAAC3' (SEQ ID NO: 9), or 5'pGATCGATCGAT3' (SEQ ID NO 10), each comprising a 5' phosphate were added to cultures of Cloudman S91 melanoma cells as described in Example 11.

pTpT, shown previously to stimulate pigmentation in these cells, was used as a reference treatment, and diluent alone was used as a negative control. After five days of treatment with the oligonucleotides, the cells were collected, counted, and an equal number of cells were pelleted for melanin analysis. The data shown in FIG. 17 demonstrate that 10 µM pTpT increased melanin content to 3 times that of control diluent-treated cells. SEQ ID NO: 5, representing the telomere over-hang sequence, also at 10 µM, increased the melanin level to 10 times that of control cells. SEQ ID NO: 9 (telomere over-hang complement) and SEQ ID NO: 10 (unrelated sequence) did not produce significant change in pigment content at concentration up to 10 µM. A truncated version of SEQ ID NO: 5, comprising TTAGGG (SEQ ID NO: 11) was also highly melanogenic, while the reverse complimentary sequence CCCTAA (SEQ ID NO: 12) was less active (FIG. 18), where both oligonucleotides contained a 5' phosphate.

The compounds of the present invention were tested for skin penetration and in vivo melanogenic activity. Mice were treated (on their ears) with fluorescently-labeled pTpT or SEQ ID NO: 1 (comprising a 5' phosphate) in propylene glycol for 4 hours, then ear skin was sectioned and examined by confocal microscopy. Treatment with either oligonucleotide resulted in brightly stained epidermis and hair follicles. Thus pTpT and SEQ ID NO: 1 comparably penetrate the skin barrier.

Figure 13:
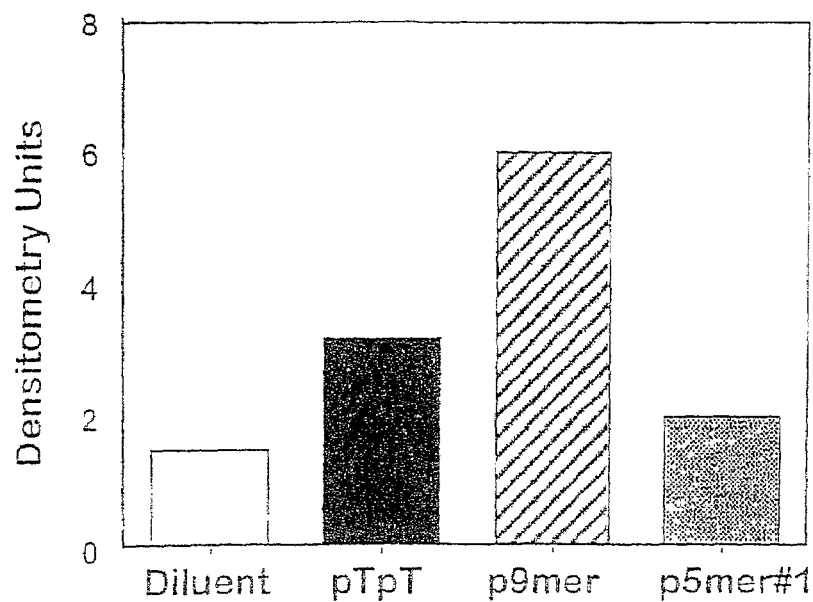
FIG. 13 shows a densitometric analysis of p21 expression detected by Northern blot analysis of SCC12F cells treated with 100 µM of the indicated oligonucleotide or an equal volume of diluent for 48 hours.
Figure 14:
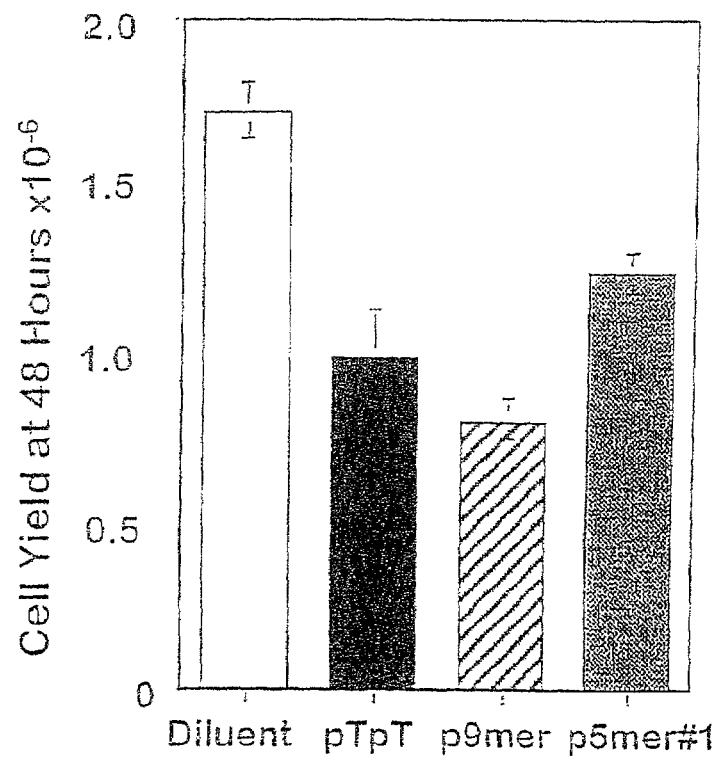
FIG. 14 shows cell yields of the samples in FIG. 13, as mean±standard deviation.

In another experiment, mice were treated once daily with either 100 µM pTpT or SEQ ID NO: 1 containing a 5' phosphate in propylene glycol on one ear, or vehicle alone on the other ear. After 15 days, when the ears were sectioned and stained with Fontana Masson to detect melanin compared to vehicle controls, there was a 70% increase in pigmentation in pTpT-treated ears and a 250% increase with SEQ ID NO: 1. Thus, both compounds comprising as few as 2 and as many as 9 nucleotides are effective at producing the in vitro UV-mimetic effects in vivo.

p53 Activation and Cell Proliferation pTpT was previously found to inhibit cell cycle progression, at least in part through activation of p53 and subsequent upregulation of the cyclin dependent kinase inhibitor p21. Cultures of the human keratinocyte line SCC12F were treated with pTpT, SEQ ID NO: 1, SEQ ID NO: 6 or diluent alone as a negative control, collected and counted 48 hours later and processed for northern blot analysis of p21 mRNA expression. SEQ ID NO: 1 was found to increase the level of p21 mRNA to almost 3-fold that of diluent control levels while pTpT-treated cells showed p21 mRNA levels twice that of control cells (FIG. 13). Cells treated with SEQ ID NO: 6 showed a 10–20% increase in p21 mRNA level. In these paired dishes, SEQ ID NO: 1 also reduced cell number by approximately 50% after 2 days, while pTpT and SEQ ID NO: 6 caused 40% and 25% reductions, respectively (FIG. 14). Thus, the sequences of the present invention activate p53 and inhibit cell proliferation similar to the effect of pTpT.

Effect of Size and Sequence

Figure 15:
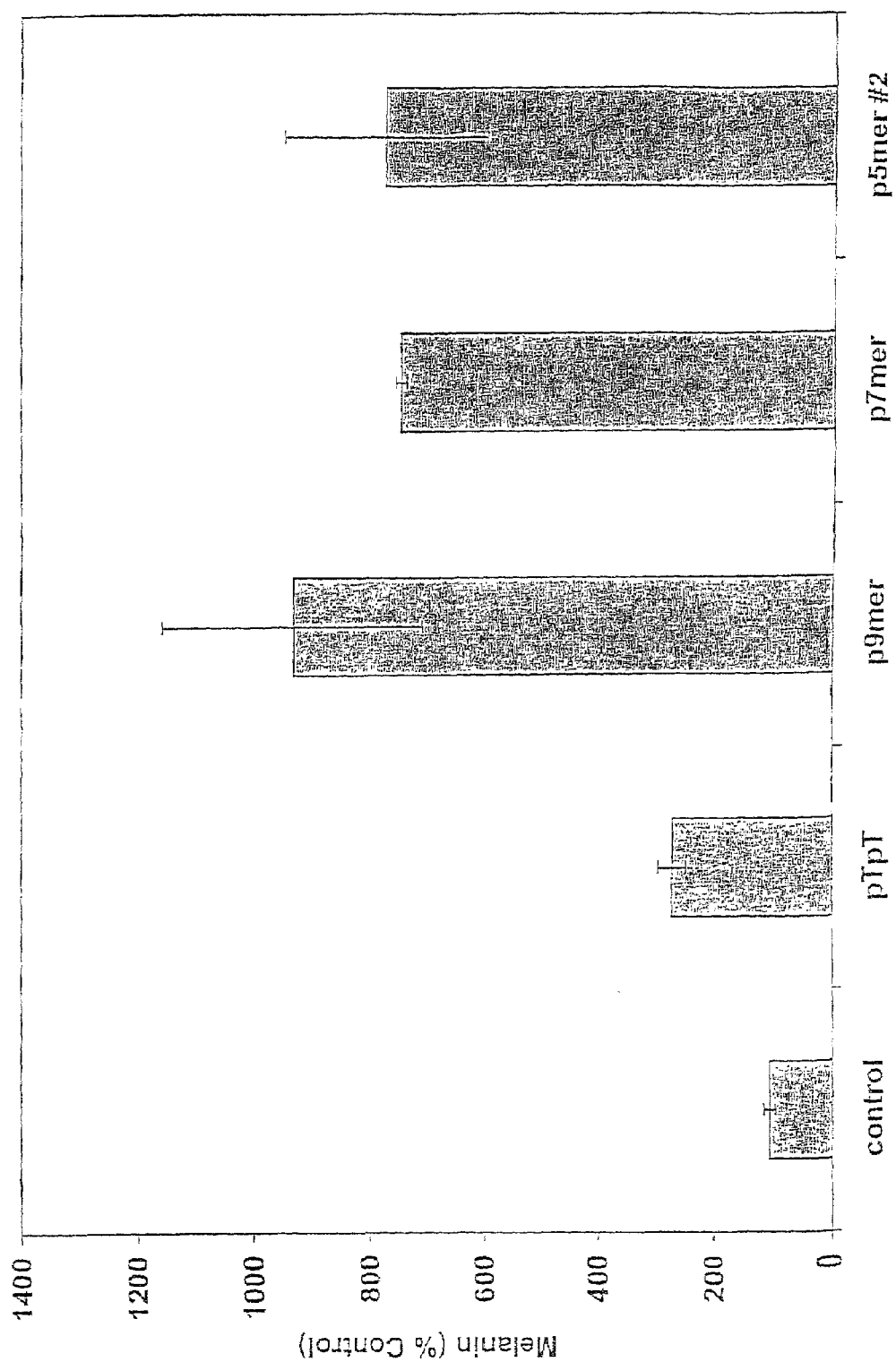
FIG. 15 shows melanin content of Cloudman S91 cells treated with 100 µM of the indicated oligonucleotide or an equal volume of diluent for 5 days as a percent of diluent-treated controls (mean±standard deviation) for 3 independent experiments.

S91 cells were cultured in the presence of diluent alone, pTpT p9mer (SEQ ID NO: 1), p7mer (AGTATGA; SEQ ID NO: 7) or p5mer #2 (SEQ ID NO: 4). After 5 days, the cells were collected, counted and an equal number of cells were pelleted for melanin analysis (FIG. 15). pTpT produced a moderate increase in melanin content and SEQ ID NO: 1, a larger increase. In addition, SEQ ID NOS: 4 and 7 also strongly stimulated melanogenesis. Both SEQ ID NOS: 4 and 7 stimulated a 7–8 fold increase in melanin. Because one p5mer was much more effective at inducing melanin production (compare results for SEQ ID NO: 4 and 6), these data suggest that oligonucleotide sequence plays a role in determining its melanogenic activity.

Figure 16:
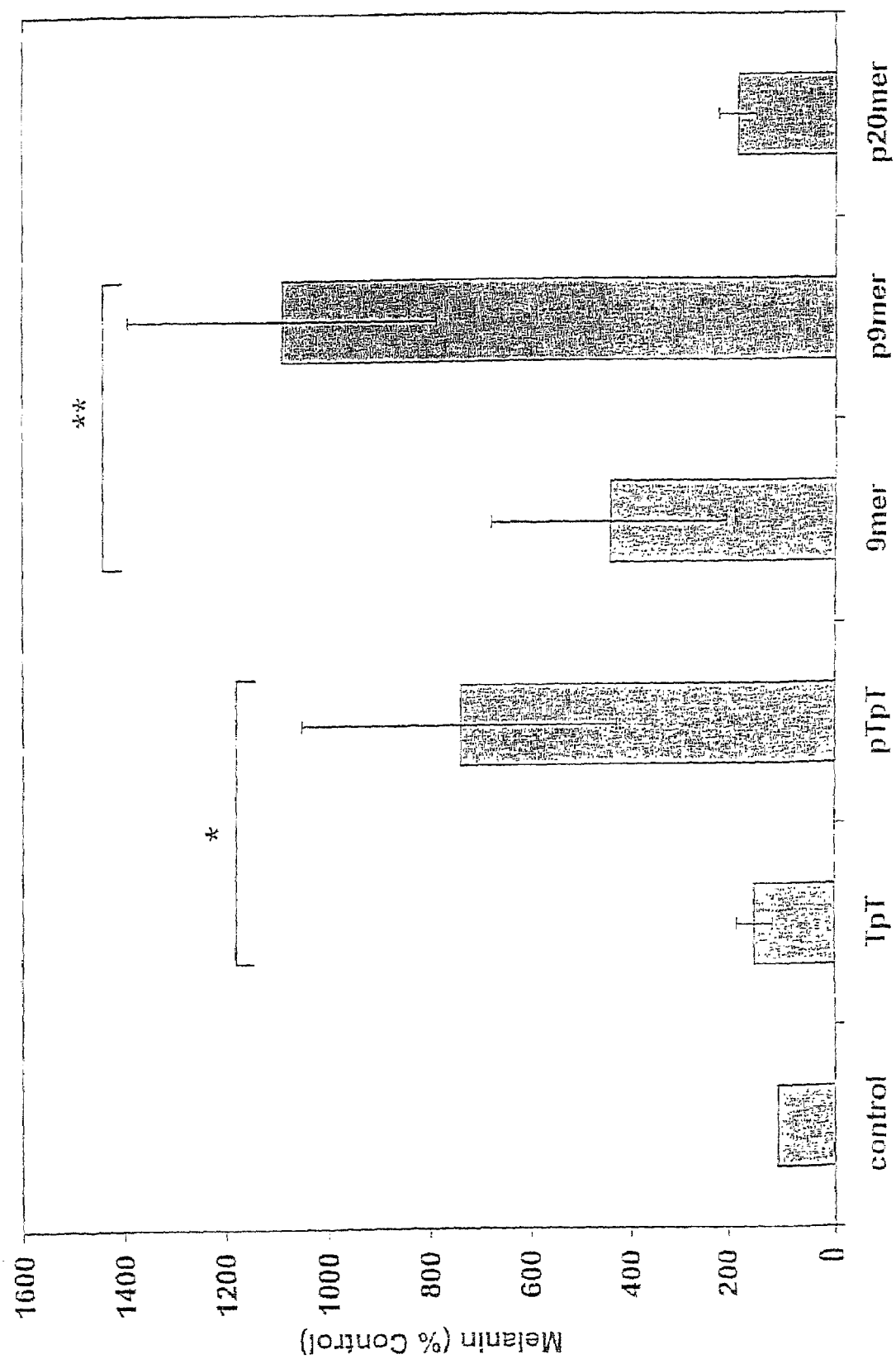
FIG. 16 shows melanin content of Cloudman S91 cells treated with 100 µM of the indicated oligonucleotide or an equal volume of diluent as described for FIG. 12, where the values represent three independent experiments and where *=p<0.004, **=p<0.03, two-tailed Student's t-test.

A p20mer was synthesized (pGCATGCATGCATTACG-TACG; SEQ ID NO: 8), with 3 repeats of the 4-base sequence GCAT, followed by two repeats TACG, an oligonucleotide with an internal pTpT that resembles the 27–29 base fragment excised during excision repair of thymine dimers in eukaryotic cells. This oligonucleotide stimulated pigmentation to twice the level of control cells (FIG. 16).

Effect of 5' Phosphorylation

S91 cells were cultured for 5 days in the presence of the thymidine dinucleotides or SEQ ID NO: 1 with or without a 5' phosphate or diluent alone as a negative control. Removal of the 5' phosphate significantly reduced the melanogenic activity of pTpT by 80% and of the 9mer by 60% ($p<0.04$ and $p<0.03$, respectively, two-tailed Student's T-test, FIG. 16. These data are consistent with an intracellular site of action of these oligonucleotides and with the reported requirement of a 5' phosphate for efficient cellular uptake.

5' Phosphorylation Increases Oligonucleotide Uptake.

Fluorescein phosphoramidite (FAM) labeled oligonucleotides were added to cultures of S91 cells for 4 hours and the cells were then prepared for confocal microscopy. Nuclei, identified by staining with propidium iodide, appeared red and FAM-labeled oligonucleotides appeared green. Co-localization of red and green signals was assigned a yellow color by the computer. Oligonucleotides with a 5' phosphate showed greater cellular uptake than those lacking this moiety. Confocal microscopy failed to detect uptake of TpT and fluorescence-activated cell sorting (FACS) analysis of these cells and gave a profile similar to that seen with untreated cells. pTpT-treated cells showed strong green fluorescence in the cytoplasm, but only a small amount of nuclear localization. FACS analysis showed a shift in the peak fluorescence intensity, compared to TpT-treated cells, indicating more intensely stained cells. Similarly, the presence of the phosphate at the 5' end of SEQ ID NO: 1 greatly enhanced its uptake into the S91 cells. SEQ ID NO: 1 without 5' phosphorylation showed only moderate uptake and was localized predominantly in the cytoplasm, with faint nuclear staining in only some cells, whereas SEQ ID NO: 1 with 5' phosphorylation showed intense staining that strongly localized to the nucleus. FACS analysis of SEQ ID NO: 1 without 5' phosphorylation showed a broad range of staining intensities with essentially two populations of cells, consistent with the confocal images. The phosphorylated SEQ ID NO: 1 containing cells also showed a range of staining intensities, but with more cells showing higher fluorescent intensity. Cells treated with phosphorylated SEQ ID NO: 8 showed a pattern of fluorescence very similar to that seen with phosphorylated SEQ ID NO: 1, both by confocal microscopy and FACS analysis, indicating that its lower activity in the melanogenesis assay cannot be ascribed to poor uptake. These data show that uptake of these oligonucleotides by S91 cells is greatly facilitated by the presence of 5' phosphate and that melanogenic activity, while consistent with a nuclear site of action, is not solely dependent on nuclear localization. Also, although the total intracellular fluorescence did not increase appreciably with increasing oligonucleotide length among the DNAs tested, the larger oligonucleotides more readily accumulated in the cell nucleus. There was no change in the profile of oligonucleotide uptake after 6 and 24 hours.

Example 13

Oligonucleotides Can Induce Apoptosis

Oligonucleotides homologous to the telomere overhang repeat sequence (TTAGGG; SEQ ID NO:11), sequence (11mer-1: pGTTAGGGTTAG; SEQ ID NO: 5), complementary to this sequence (11mer-2: pCTAACCCTAAC; SEQ ID NO: 9) and unrelated to the telomere sequence (11mer-3: pGATCGATCGAT; SEQ ID NO: 10) were added to cultures of Jurkat cells, a line of human T cells, one of the cell types reported to undergo apoptosis in response to telomere disruption. Within 48 hours, 50% of the cells treated with 40 µM of SEQ ID NO: 5 had accumulated in the S phase, compared to 25–30% for control cells ($p<0.0003$, non-paired t-test; see FIGS. 19A–19D), and by 72 hours, 13% of these cells were apoptotic as determined by a sub-$G_0/G_1$ DNA content, compared to 2–3% of controls ($p<0.007$, non-paired t-test; see FIGS. 19E–19H). At 96 hours, 20±3% of the 11mer-1 treated cells were apoptotic compared with 3–5% of controls ($p<0.0001$, non-paired t-test). To exclude preferential uptake of the 11mer-1 as an explanation of its singular effects, Jurkat cells were treated with oligonucleotides labeled on the 3' end with fluorescein phosphoramidite, then subjected to confocal microscopy and FACS analysis. The fluorescence intensity of the cells was the same after all treatments at 4 hours and 24 hours. Western analysis showed an increase in p53 by 24 hours after addition of 11mer-1, but not 11mer-2 or -3, with a concomitant increase in the level of the E2F1 transcription factor, known to cooperate with p53 in induction of apoptosis and to induce a senescent phenotype in human fibroblasts in a p53-dependent manner as well as to regulate an S phase checkpoint.

Example 14

The Effect of DNA Fragments on DNA Mutation Frequency In vivo

Transgenic mice carrying multiple genomic copies of a LacZ reporter plasmid were used. One hundred µM pTpT in polypropyleneglycol was applied to one ear and vehicle alone to the other ear, daily for four days. On the fifth day, both ears were exposed to 100 mJ/cm$^2$ UVB light. This procedure was repeated weekly for 3, 5 or 7 weeks (3 mice/group). One week after the final irradiation, LacZ plasmids were harvested from the ear epidermis. Using methods well known in the art, the plasmids were recovered from genomic DNA by restriction enzyme digestion and specific binding to the LacI protein. Mutant LacZ plasmids were positively selected by transfection into bacteria and growth on selective medium and the mutation frequency was determined. After 3, 5, and 7 weeks, pTpT-treated skin exhibited a 20–30% lower mutation frequency than diluent treated skin (200 vs 293, 155 vs 216, and 261 vs 322, respectively). These data showed that pTpT-enhanced DNA repair reduces UV-induced mutations in vivo and suggest

Example 15

DNA Fragment Protect Against Oxidative Damage

Primary newborn fibroblasts were treated for 3 days with 10 μM pTpT or diluent as control and then treated with $5\times10^{-5}$ or $5\times10^{-4}$ M $H_2O_2$. Within 72 hours of $H_2O_2$ exposure, cell yields of pTpT pre-treated cultures were 45±1% and 139±5% higher, respectively, compared to diluent pre-treated control samples. 72 hours after exposure of the low $H_2O_2$ dose, only 9.6±2.4% of the diluent pre-treated cells survived. In contrast, pTpT pre-treatment increased cell survival by 2–9 fold at $5\times10^{-4}$ M $H_2O_2$ and conferred complete protection at the low dose. mRNA levels of Cu/Zn superoxide dismutase, an enzyme that participates in the process of oxygen radical quenching, were increased by greater than 3 fold 48 and 72 hours after pTpT treatment and remained elevated at least 24 hours after pTpT withdrawal (when the experiment was terminated).

Example 16

Age Related Decline in DNA Repair Capacity Is Reversed by Oligonucleotides

Human dermal fibroblasts (fb), derived from newborn, young adult (25–35y), and older adult (65–90y) donors were pre-treated with 10 μM pTpT or SEQ ID NO: 1 containing a 5' phosphate or diluent as a control for 24 hours. The samples were then UV irradiated with 5, 10 and 30 m/cm². DNA and proteins were collected at time 0 and up to 24 hours post-UV. There were age-associated decreases in the constitutive and UV-induced protein levels of p53, p21, XPA, RPA ERCC/PF and PCNA. However, in all age groups, pre-treatment with oligonucleotides resulted in up-regulated constitutive and UV-induced levels of these proteins by 200–400%. Furthermore, slot blot analysis specific for thymine dimers and (6–4) photoproducts showed a significant decrease with aging in the DNA repair states in the first 16 hours post-UV. Pre-treatment with oligonucleotides increased the removal of photoproducts by 30–60 percent.

Example 17

Phosphorothioate Version of the Telomere Overhang Homolog 11mer-1 Does Not Induce Apoptosis Cultures of Jurkat human T cells were treated with either diluent, 11mer-1 (SEQ ID NO:5) or the phosphorothioate 11mer-1 (11mer-1-S) for 96 hours, then collected and processed for FACS analysis. Two concentrations of the oligonucleotides were tested, 0.4 μM (FIGS. 20A–20C) and 40 μM (FIGS. 20D–20F). At the 0.4 μM concentration, neither of the oligonucleotides affected the expected exponentially growing cell cycle profile of the Jurkat cells. At 40 μM, the 11-mer-1 induced extensive apoptosis in these cells, indicated by a sub-$G_0/G_1$ peak, while the 11mer-1-S had no effect.

Example 18

Phosphorothioate Version of 11mer-1 Blocks Induction of S-Phase Arrest by the Phosphate Backbone 11mer-1

Cultures of a keratinocyte cell line (SSC12F, 100,000 cells/38 cm²) were treated for 48 hours with only the 11mer-1 (SEQ ID NO:5) or with the 11mer-1 in the presence of increasing concentrations of the 11mer-1-S. As shown previously in Example 13, the 11mer-1 induced an S-phase arrest as demonstrated by FACS (Becton-Dickinson FacScan). Forty-three precent of the cells were in the S phase, compared to 26% of the control, diluent-treated cells. However, when increasing concentrations of the phosphorothioate 11mer-1 were also added to these cultures, fewer cells became arrested (FIGS. 21A–21G). Complete inhibition of this arrest was seen with a ratio of 11mer-1: 11mer-1-S of 2:1. The 11mer-1-S by itself did not induce the S-phase arrest.

Example 19

Figure 22:
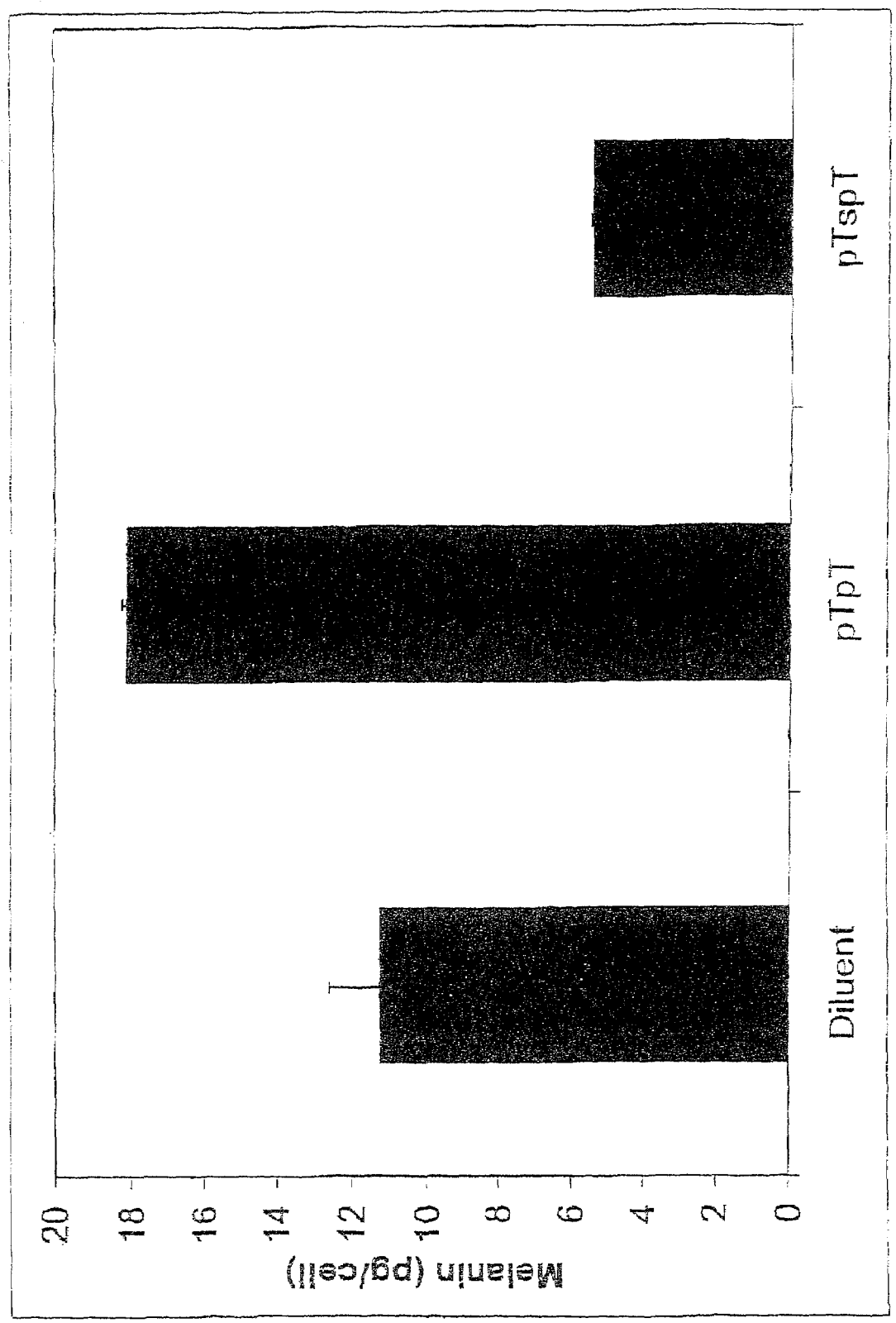
FIG. 22 is a bar graph showing the melanin content (in pg/cell) of cells treated with diluent, pTpT or pTspT.
Figure 23:
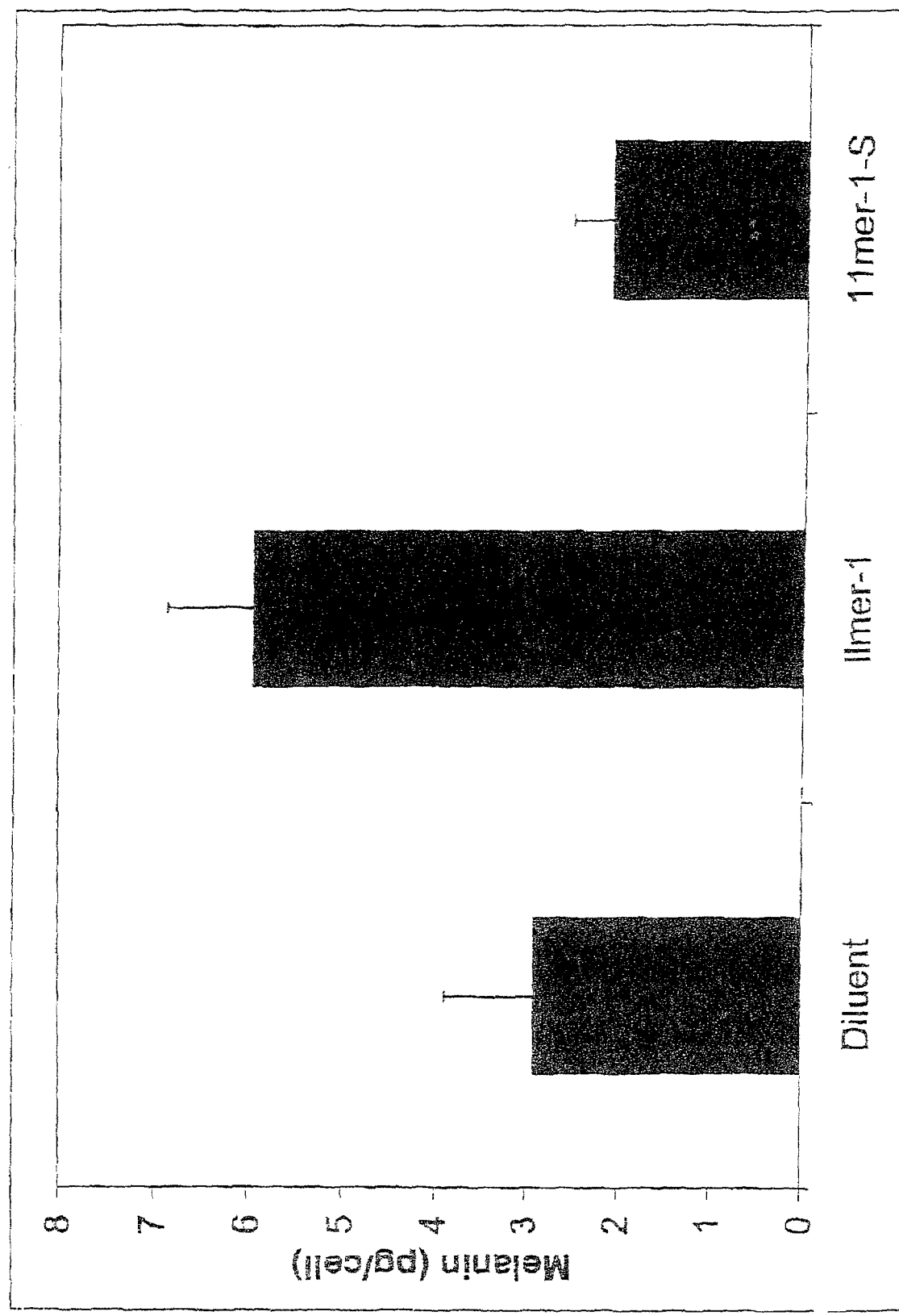
FIG. 23 is a bar graph showing the melanin content (in pg/cell) of cells treated with diluent, 11mer-1 or 11mer-1-S.

Phosphorothioate Forms of the Telomere Oligonucleotides Reduce Constitutive and UV-Induced Pigmentation and Do Not Stimulate Melanogenesis Cultures of S91 mouse melanoma cells (100,000 cells/38 cm²) were treated with 100 μM pTpT or phosphorothioate pTpT (pTspT) (FIG. 22) or 40 μM 11mer-1 or the phosphorothioate 11mer-1 (11mer-1-S) (FIG. 23) for 6 days and were then collected, counted and assayed for melanin content. While the pTpT and 11mer-1 (FIG. 22 and FIG. 23, respectively) stimulated melanogenesis in these cells, pTspT and 11mer-1-S did not (FIG. 22 and FIG. 23, respectively). Furthermore, both pTspT (FIG. 22) and 11mer-1-S (FIG. 23) reduced the constitutive pigmentation in these cells, suggesting that chronic exposure of this sequence during telomere repair/replication may provide a constant, low level signal for melanogenesis and this signal is blocked by pTspT and 11mer-1-S.

Example 20

Phosphorothioate pTspT Inhibits UV-Induced Melanogenesis

Figure 24:
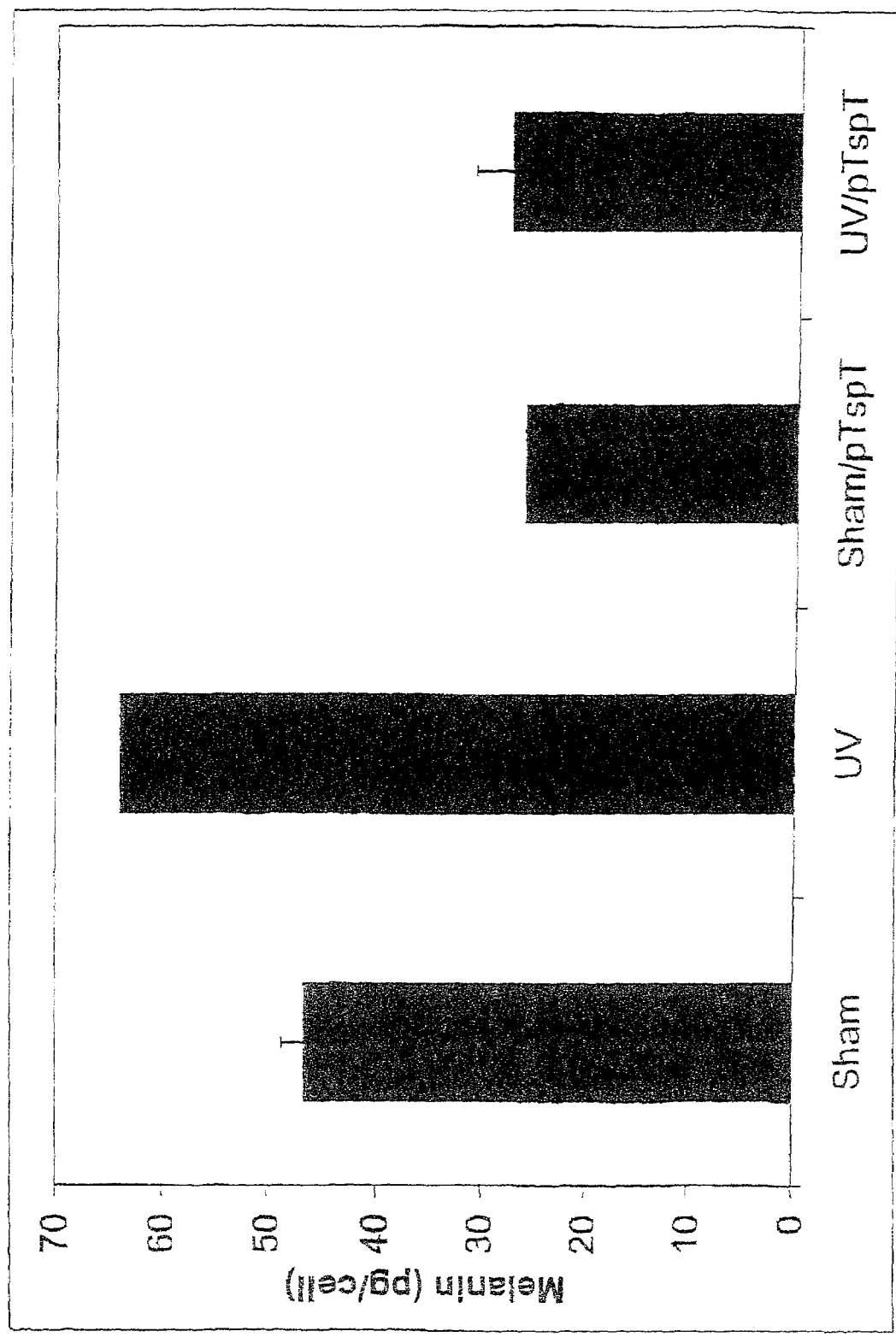
FIG. 24 is a bar graph showing the melanin content (in pg/cell) of cells that have been sham-treated (no irradiation, no oligonucleotides), or treated with ultraviolet light (UV), or unirradiated but given pTspT, or irradiated with UV and given pTspT.

Duplicate cultures of S91 cells (100,000 cells/39 cm²) were either sham-irradiated or irradiated with 5 mJ/cm² solar-simulated light from a 1 kW xenon arc solar-simulator (XMN 1000-21, Optical Radiation, Azuza, Calif.) metered at 285±5 mn using a research radiometer (model IL1700A, International Light, Newburyport, Mass.). Two sham-irradiated plates were then supplemented with 100 μM pTspT and two irradiated cultures were similarly treated with pTspT. After one week, cells were collected, counted and analyzed for melanin content by dissolving the cell pellets in 1 N NaOH and measuring the optical density at 475 μm. UV irradiation resulted in a doubling of melanin content in these cells. However, this response was blocked by the addition of pTspT (FIG. 24). In addition, the constitutive pigmentation of these cells was reduced by the pTspT in the sham-irradiated cultures, similar to the data presented in FIGS. 22 and 23.

Example 21 pTpT Induces SOD2 Protein Level in Fibroblasts

Fibroblasts (newborn human) were maintained in Dulbecco's Modified Eagle Medium (DMEM) supplemented with 10% calf serum (CS) and 100 µM pTpT or diluent as control. Total cellular proteins were harvested at different intervals after stimulation and processed for western blot analysis. The blot was reacted with anti SOD2 antibodies (The Binding Site, Inc. San Diego, Calif.). While fresh medium supplementation transiently induced the 37 kDa SOD2 in diluent treated control cultures, in pTpT treated cultures SOD2 induction was sustained at least through 32 hours when the experiment was terminated. Coomassie blue-stained residual bands on the gel confirmed uniform loading of the different lanes.

Example 22

Pretreatment With pTpT Protects Against Oxidative Damage

Figure 25:
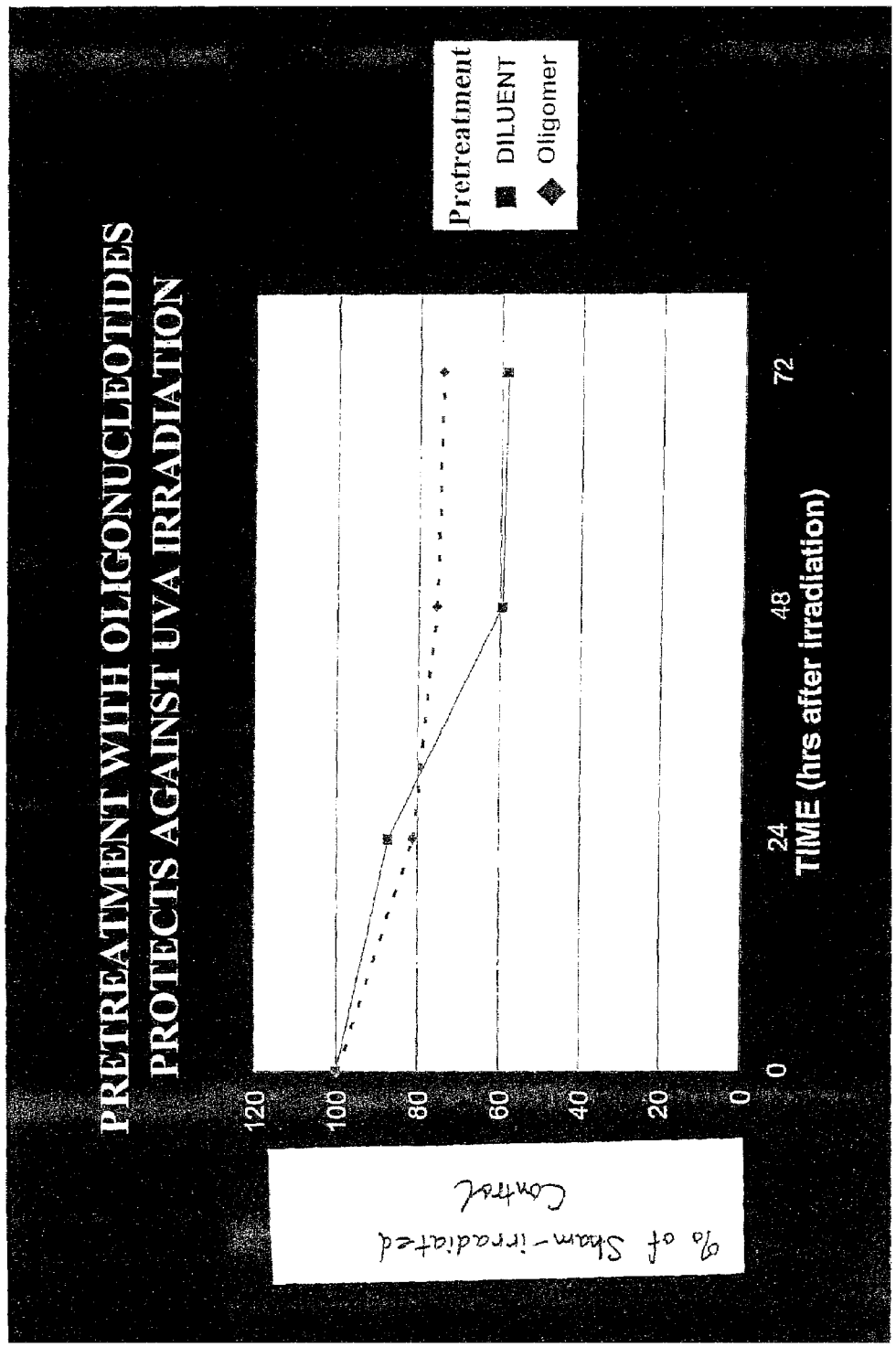
FIG. 25 is a graph in which viable cell count, as a percent of the cell count for the respective sham-irradiated control, is shown as a function of time after ultraviolet irradiation for diluent-treated (squares) or pTpT-treated (diamonds) cells of squamous carcinoma cell line SCC12F.

Cells from the well differentiated squamous carcinoma line SCC12F (gift of Dr. James Rheinwald, Harvard University) were treated with 100 µM pTpT or diluent as control for 3 days. Then cells were re-plated in medium lacking pTpT and were sham- or UV-irradiated with 10 J/cm$^2$ UVA (Sellas Sunlight UVA lamp). Cell yields were determined at different intervals after UV irradiation. FIG. 25 represents yields of UVA treated cells that were either pretreated with pTpT or pretreated with diluent, each as a percent of its own sham irradiated control. pTpT pretreatment increased the yields of UVA irradiated cells.

Example 23 pTpT Induces Apurinic Endonuclease-1 (APE-1) Protein in Fibroblasts

Fibroblasts (human newborn) were maintained in 10% CS-supplemented DMEM containing 100 µM pTpT, 10 µM or 60 µM oligonucleotide pGTTAGGGTTAG (SEQ ID NO:5), or diluent as control. Total cellular proteins were harvested at different intervals after supplementation and processed for western blot analysis. Expression of APE-1, the rate-limiting enzyme in repair of 8-oxoguanine (the principal form of oxidative DNA damage) was studied. The blot was incubated with anti APE-1 antibodies (APE/Ref-1 monoclonal IgG2b, Novus Biologicals, Inc. Littleton, Colo.). Within 24 hours of supplementation with pTpT or the 11mer oligonucleotide having nucleotide sequence SEQ ID NO:5, the 37 kDa APE-1 protein was induced in samples stimulated with the oligonucleotides as compared to diluent control. The induction was sustained for at least 48 hours, when the experiment was terminated. Coomassie blue-stained residual bands on the gel confirmed uniform loading of the different lanes.

Example 24 pTpT Induces Repair of UVA Damage to pCMV-Luc Plasmid

Figure 26:
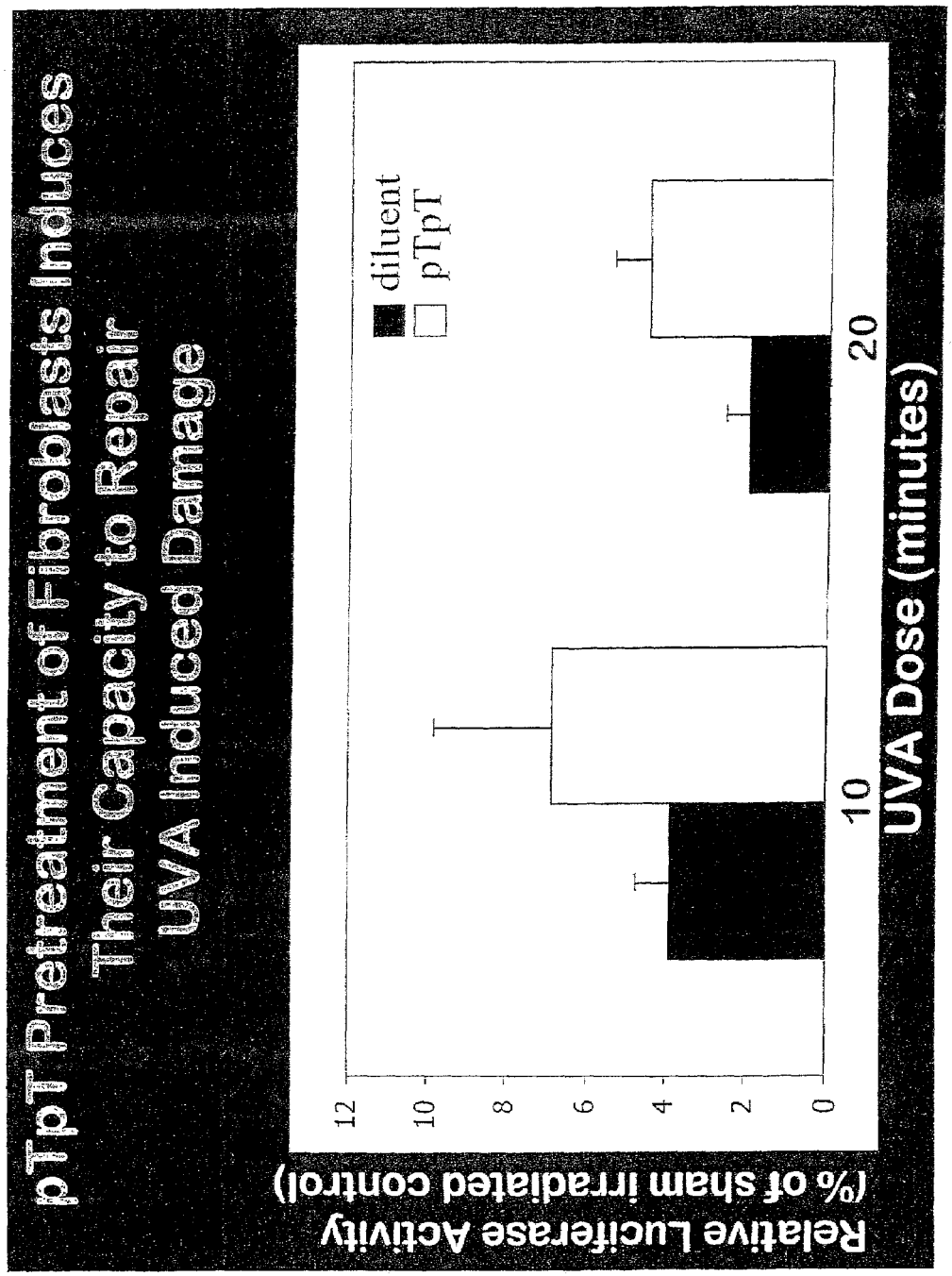
FIG. 26 is a bar graph in which the repair capacity of normal human fibroblasts, after UVA-induced damage and treatment with pTpT, is shown as the luciferase activity generated from expression of a gene in the non-replicating vector pCMV-Luc. Luciferase activity, as a percent of a sham-irradiated control, is plotted for diluent-treated (black bars) and pTpT-treated (white bars) for fibroblasts irradiated for 10 or 20 minutes. See Example 24.

The plasmid pCMV-Luc is a non-replicating vector containing a reporter gene, luciferase, under the control of a strong constitutive cytomegalovirus promoter (gift of Dr. Hedayati, Johns Hopkins University). Singlet oxygen-induced DNA damage of the plasmid was generated by irradiating the plasmid with visible light for different time intervals (0 min, 10 min and 20 min), in the presence of the photosensitizer methylene blue. Fibroblasts (human newborn), pretreated for 48 hours with 100 µM pTpT or with diluent alone, were transfected with 0.5 µg of pCMV-Luc using Lipofect Aminem (Promega, Madison, Wis.). After two days, plasmid-encoded luciferase activity was determined in cell extracts (Promega luciferase assay). Pretreatment with pTpT enhanced the repair of singlet oxygen-induced DNA damage after 10 mJ/cm$^2$ and 20 mJ/cm$^2$ UVA irradiation by 179% and 228% respectively. FIG. 26 represents luciferase activity as a percent of luciferase activity assayed in fibroblasts transfected with sham irradiated plasmid.

Example 25

DNA Oligonucleotides Protect Murine Skin From Photodamage

Patients with a mutated xeroderma pigrnentosum group A (XPA) gene have a greater than 1000 fold increased risk of UV-induced skin cancer. XPA$^{-/-}$ mice mimic the human syndrome [Kraemer, K. et al., pp. 256–261 In: *Molecular Biology of Aging* (Bohr, V. A., et al., eds.) Munksgaard, Copenhagen, 1999]. We have previously shown that oligonucleotides, particularly thymidine dinucleotide (pTT) and pGAGTATGAG (SEQ ID NO:1) that are partial homologs of the telomere overhang tandem repeat TTAGGG (SEQ ID NO:11), increase levels of proteins involved in nucleotide excision repair and enhance the DNA repair rate. To determine the effect of oligonucleotides in vivo, XPA$^{+/+}$ and XPA$^{-/-}$ mice were treated with 100 µM pTT, 40 µM pGAGTATGAG (SEQ ID NO:1), or diluent alone, daily for 4 days. A 30 µl volume of oligonucleotides or diluent in 90% propylene glycol/10% DMSO was applied to a 3 cm$^2$ area of skin along the spinal ridge of the mice. The mice were UV irradiated on day 5 with a previously determined erythemogenic UVB dose. The course of treatment—4 days of oligonucleotide (or diluent) applications, starting with oligonucleotide on day 1 of each week, with LV irradiation on day 5—was repeated for a total of 4 weeks. Seventy-two hours after the last dose of LV irradiation, the mouse skin was processed histologically to assess general morphology, proliferation (Ki-67) [Ohike N. and T Morohoshi, *Pathol Int* (2001), 51:770–777; Billgren, A. M. et al., *Breast Cancer Res Treat* (2002), 71:161–170], cyclobutane pyrimidine dimers (CPDs) determined by specific antibody binding, and on-going DNA repair [proliferating cell nuclear antigen (PCNA); see Savio, M. et al., *Carcinogenesis* (1998) 19:591–596; Rudolph, P. et al., *Hum Pathol* (1998) 29:1480–1487].

Diluent treated XPA$^{+/+}$ and XPA$^{-/-}$ skin showed spongiosis, blistering, and dyskeratosis, whereas oligonucleotide-treated samples lacked these features. After 72 hours, only XPA$^{-/-}$ diluent-treated samples contained CPDs: 15±5 (+) cells per 400× microscopic field vs. none in samples from mice treated with pTT or SEQ ID NO:1 (p<0.0001). No XPA$^{+/+}$ samples contained CPDs. Ki67 (+) cells were more numerous in diluent-treated than in oligonucleotide-treated XPA$^{-/-}$ skin, consistent with a hyperproliferative "rebound" after UVB damage: 14±4 vs. 5±2 (p<0.005). However, PCNA (+) cells were more numerous in both XPA$^{+/+}$ and XPA$^{-/-}$ oligonucleotide-treated skin: 38±2 vs. 52±6 (p<0.01) and 125±8 vs. 89±11 (p<0.001), consistent with the role of PCNA in on-going DNA repair, and with previously reported up-regulation of PCNA by oligonucleotides in vitro.

These data demonstrate that topical application of telomere homolog oligonucleotides enhances the skin's ability to repair repeated UVB damage, in large part through increased DNA repair capacity. The photoprotective effects were observed in both repair-proficient and severely repair-deficient animals, suggesting a therapeutic role in cancer prevention.

Example 27

Single-Stranded DNA Homologous to the 3' Overhang Telomere Sequence Mimics UV Effects on Mitochondrial Gene Expression Exposure of keratinocytes to UVB irradiation affects the expression of genes involved in cell cycle arrest, DNA repair and cytokine production. Single-stranded oligonucleotides sharing sequence homology with the telomere 3' overhang, when introduced into cells, mimic these UV effects. To identify other genes that may be similarly modulated, cells of keratinocyte origin (SCC12F; a human epidermal squamous cell carcinoma line provided by Dr. James Rheinwald of Harvard University) were exposed to solar simulated irradiation (SSR) (20 mJ/cm$^2$, measured at 285±5 nm), to an 11-base oligonucleotide (pGTTAGGGTTAG; SEQ ID NO:5) homologous to the telomere overhang (T-oligo), or to a complementary sequence as control [pCTAACCCTAAC; (SEQ ID NO:9) control oligonucleotide]. Similar to SSR, T-oligo substantially inhibited cellular proliferation and arrested >43% of cells in the S-phase of the cell cycle, compared to <23% of control cells. Using DNA microarray chips containing >700 genes known to be modulated by aging and stress conditions, we identified 8 genes that were downregulated by >50% with SSR and T-oligo treatment, but not with sham irradiation or control oligo treatment. Specifically, the modulated genes encode subunits of the mitochondrial enzymes ATPase and cytochrome c oxidase, known to be transcriptionally downregulated by UV, and NADH dehydrogenase. These are mitochondrial-transcribed genes whose encoded proteins participate in cellular respiration. Semi-quantitative RT-PCR and northern blot analysis confirmed the above data and showed that the genes were comparably downregulated by SSR and T-oligo treatment as early as 24 hours and 48 hours, respectively. Using microarray chips that provide a rapid means for analyzing expression of many genes simultaneously, it was demonstrated that mitochondrial-encoded gene products involved in respiration are similarly modulated by UV irradiation and DNA homologous to the telomere 3' overhang. The data suggest that DNA damage responses mimicked by telomere homolog DNA include temporary reduction of energy consumption by cells.

Example 28

Induction of S-phase Arrest and Apoptosis by Telomere Overhang Oligonucleotide

Materials and Methods Applying to Examples 28–37 Oligonucleotides

Three DNA oligonucleotides were designed initially: one homologous to the telomere overhang (11mer-1: pGT-TAGGGTTAG; SEQ ID NO:5), one complementary to this sequence (11mer-2: pCTAACCCTAAC; SEQ ID NO:9) and one unrelated (11mer-3: pGATCGATCGAT; SEQ ID NO:10). For later experiments, additional 11 base oligonucleotides were designed: one a simple permutation of 11mer-1 (pGGGTTAGGGTT; SEQ ID NO:13), one with the same number of G residues but roughly 50% rather than 100% homology to the overhang (pTAGATGTGGTG; SEQ ID NO:14), and one with roughly 50% overhang homology but also containing cytosine bases (pCGGGCTTATTG; SEQ ID NO:15) (Midland Certified Reagent Company, Midland, Tex.).

Cell Sources and Culture

Human neonatal fibroblasts were established and cultured as previously described (Eller, M. S., et al., 1997, *Proc Natl Acad Sci USA* 94: 12627–12632). Fibroblasts from a Nijmegen breakage syndrome (NBS) patient (#GM07166) and an age-matched control (GM03399) were purchased from the NIGMS Human Cell Repository, Coriell Institute for Medical Research, Camden, N.J.) and cultured in DMEM/15% FBS. Saos-2 cells were purchased from the American Type Culture Collection (ATCC; Manassas, Va.). SCC12F cells were the kind gift of Dr. James Rheinwald, Harvard University.

Cell Cycle Analysis

The established line of human T lymphocytes, termed Jurkat cells (180,000 cells/ml) were plated in RPMI medium 1640 supplemented with 3% FBS (both from GIBCO/BRL, Gaithersburg, Md.). Duplicate cultures were treated with a final concentration of 40 μM oligonucleotide or an equal volume of diluent (water) as a control. Cells were collected up to 96 hours after treatment, stained with propidium iodide and analyzed by FACS using a Becton-Dickinson FacsScan and CellQuest software.

Caspase Activity

Duplicate cultures of Jurkat cells were cultured and treated with oligonucleotides as described above. At 48, 72 and 96 hours of treatment, cells were collected by centrifugation, washed and then the pellet lysed by repeated cycles of freeze-thawing. The lysate was then clarified by centrifugation and the supernatant used for protein analysis and Caspase-3 activity assay using the components and instructions of the Colorimetric CaspACE Assay System from Promega (Madison, Wis.). The assay uses the substrate Ac-DEVD-pNA and calorimetrically measures release of free pNA. Caspase activity is expressed as pmol of pNA produced/hour/μg protein.

TUNEL Analysis

Cells were plated at a density of 180,000 cells/ml in RPMI 1640 medium supplemented with 3% FBS. Cells were treated with 40 μM of either of the oligonucleotides for 72 hours. Cells were then collected, washed and fixed for 30 minutes in 4% paraformaldehyde and then permeabilized with 0.1% Triton X-100 for 2 minutes. The TUNEL assay was carried out with components and instructions of the In Situ Cell Death Detection Kit using fluorescein-labeled dUTP from Boehringer Mannheim. TUNEL-positive cells were detected by FACS analysis and confocal microscopy.

Cellular Uptake of Oligonucleotides

For confocal analysis, Jurkat cells were plated on Permanox chamber slides (Lab-Tek, Naperville, Ill.) and treated for 4 hours with fluorescein phosphoramidite (FAM)-labeled oligonucleotides (Research Genetics, Inc., Huntsville, Ala.). Adherent cells were fixed in 4% paraformaldehyde in PBS, stained with propidium iodide (PI) to identify nuclei, mounted with Slowfade reagent (Molecular Probes, Eugene, Oreg.), covered with a coverslip and stored at 4° C. in the dark. Uptake of the oligonucleotides was assessed in 5–10 µm sections with a Carl Zeiss LSM 510 confocal laser microscope. Computer images assign green to the FAM-oligonucleotides, red to PI, and yellow to co-localization of the signals. FACS analysis was performed on Jurkat cells identically treated with the FAM-oligonucleotides for 4 hours, then fixed in 0.5 ml of 4% paraformaldehyde overnight at 4° C. Fluorescence was measured on the FL-1 channel.

Western Blot Analysis and Antibodies

Western blot analysis was performed as previously described [Eller, M. S., et al., (1996), *Proc Natl Acad Sci USA* 93, 1087–1092]. Antibody Ab-6 (DO-1 clone, Oncogene Research Products, Cambridge, Mass.) detected p53; antibody KH95 (Santa Cruz Biotechnology, Inc., Santa Cruz, Calif.) detected E2F1; antibody Ab-4 (Oncogene Research products) detected p73. Phospho-p53 (serine 15) was detected using the #9284 polyclonal antibody and phospho-p95/Nbs1 (serine 343) was detected by a phospho-p95/Nbs1-specific polyclonal antibody, both antibodies from Cell Signaling Technology (Beverly, Mass.). p95/Nbs1 antibody (#NB-100-143, Novus Biologicals, Littleton, Colo.) and an actin antibody (I-19, Santa Cruz Biotechnology, Santa Cruz, Calif.) were also used.

Modification of p95/Nbs1

Jurkat and SCC12F cells were cultured and treated with the oligonucleotides as described above. After the indicated times, total protein was collected and analyzed by 8% PAGE and western blot using a polyclonal antibody to p95/Nbs1 (#NB-100-143, Novus Biologicals, Littleton, Colo.). Immunoprecipitation and treatment with a serine/threonine phosphatase was performed as described by Lim et al. [Lim, D. S. et al., *Nature* 404:613–617, 2000].

Transient Transfection and Expression of TRF2$^{DN}$

The Ad TRF2$^{DN}$ expression vector was the kind gift of Dr. Titia deLange (Rockefeller University). The control vector, pCMV LUC was the gift of Dr. M. Hedayati, Johns Hopkins University. Cells were plated at a density of 3.5×10$^3$ cells/cm$^2$. One day later, the cultures were transfected with 1 µg plasmid DNA/35 mm culture dish, using the Fugene 6 Transfection Reagent (Roche Molecular Biochemicals, Indianapolis, Ind.), following the protocol supplied by the manufacturer. Cells were collected at the indicated times after transfection and p95/Nbs1 was examined by western blot as described.

Telomere Length

Normal human fibroblasts were cultured for 5 days in the presence of either diluent or 40 µM 11mer-1, -2 or -3. The cells were then collected and the genomic DNA isolated using the DNeasy Tissue Kit (Qiagen, Valencia, Calif.). Telomere length was determined essentially as described by van Steensel and de Lange (van Steensel, B. and T. de Lange. 1997, *Nature* 385: 740–743) using the Telo TAGGG Telomere Length Assay from Roche Molecular Biochemicals (Indianapolis, Ind.) and the protocol supplied by the manufacturer. The mean telomere length (MTL) was calculated by densitometry and using the method of Harley et al. (Harley, C. B., et al., 1990, *Nature* 345: 458–460).

3' Overhang Assay

Normal human fibroblasts were cultured in the presence of 40 µM 11mer-1 for up to 7 days. Cells were collected before treatment (time 0) and at 3, 5 and 7 days of treatment. The genomic DNA was isolated using the DNeasy kit. Detection of the 3' overhang was carried out as described by van Steensel, Smogorzewska and de Lange (van Steensel, B., et al, 1998, *Cell* 92: 401–413). A probe ([TTAGGG]$_4$) was hybridized to the genomic DNA to control for hybridization to telomeric double-stranded DNA. The test primer ([CCCTAA]$_4$) was used to detect the overhang.

Oligonucleotides homologous to the 3' overhang sequence (11mer-1: pGTTAGGGTTAG; SEQ ID NO:5), complementary to this sequence (11mer-2: pCTAAC-CCTAAC; SEQ ID NO:9) and unrelated to the telomere sequence (11mer-3: pGATCGATCGAT; SEQ ID NO:10) were synthesized. The three 11mer oligonucleotides were added to cultures of Jurkat cells, an established line of human T lymphocytes, a cell type reported to undergo apoptosis in response to telomere disruption [Karlseder, J., et al, (1999) *Science* 283, 1321–1325] and DNA damaging ionizing radiation (IR) [Vigorito, E., et al, (1999), *Hematol Cell Ther* 41, 153–161]. Duplicate cultures of Jurkat cells were treated with a final concentration of 40 µM 11mer-1, -2 or -3, oligonucleotides, or an equal volume of diluent (water) as a control. Cells were collected up to 96 hours after treatment, stained with propidium iodideandanalyzed by FACS. See also Example 13 and FIGS. 19A–19H.

Figure 27:
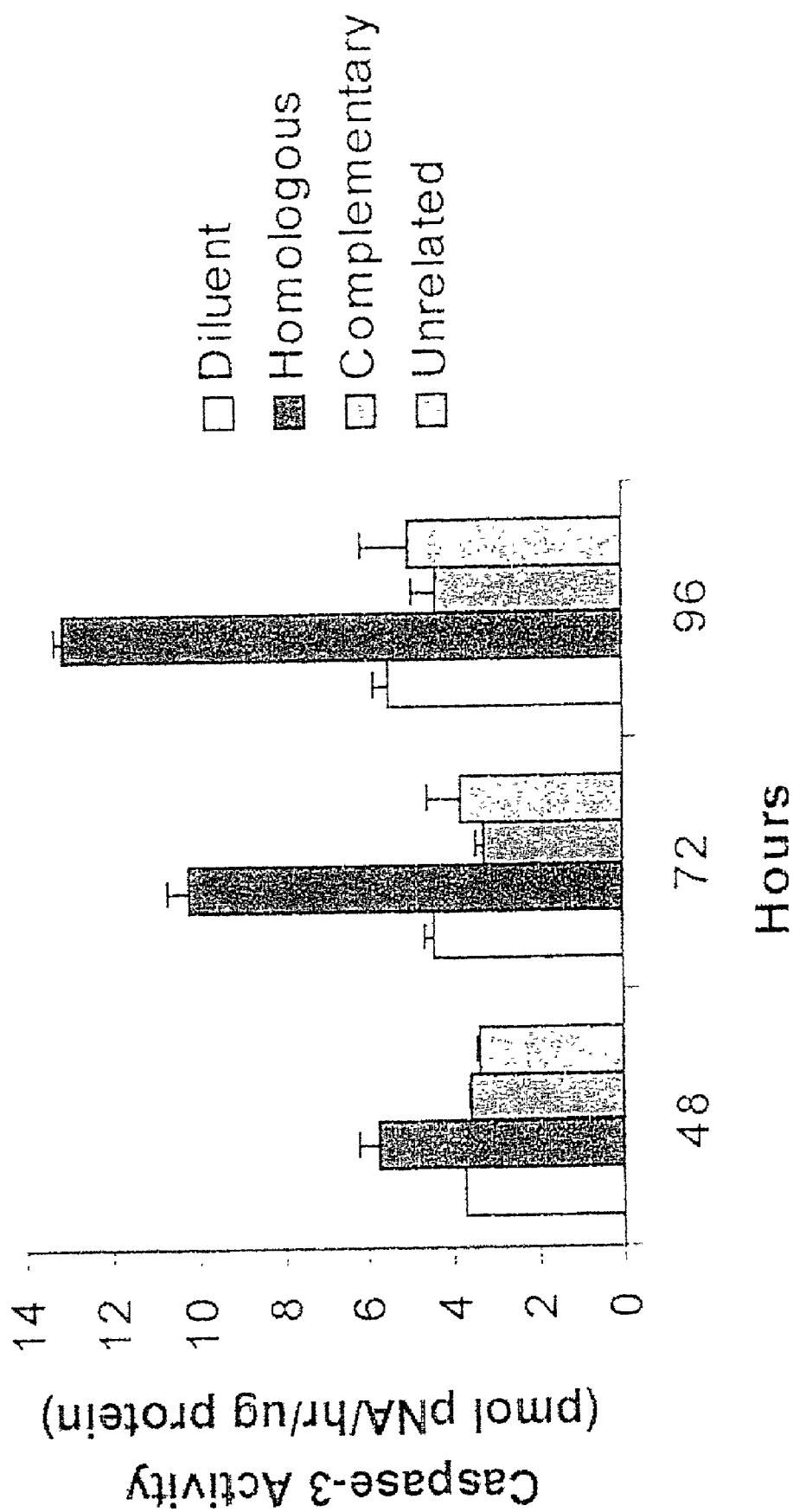
FIG. 27 is a bar graph showing the results of an assay for caspase-3 activity in Jurkat cells treated with (bars, as shown left to right): diluent, oligonucleotide homologous to telomere sequence, oligonucleotide complementary to telomere sequence, or an unrelated oligonucleotide. Caspase-3 activity (in pmol pNA/hr/µg protein resulting from the assay) is plotted for 48, 72 and 96 hours of incubation of the cells with the oligonucleotides.

Apoptosis was also detected by the DNA end-labeling TUNEL assay. Jurkat cells were treated with 40 µM oligonucleotides for 72 hours. Cells were then collected and the TUNEL assay was carried out. Only Jurkat cells treated with the overhang homolog SEQ ID NO:5 displayed an increase in fluorescence due to end-label incorporation as seen by FACS analysis and confocal microscopy. The activation of caspase-3, another marker of apoptosis, was also examined. Duplicate cultures of Jurkat cells were cultured and treated with oligonucleotides as described above for 48, 72 and 96 hours and caspase-3 activity was measured. The activity of caspase-3 was 50% higher after 48 hours of treatment with the telomere overhang homolog, compared to controls, and 3–4 fold higher in these cells at 72 and 96 hours (FIG. 27). Thus, the oligonucleotide homologous to the telomere 3' overhang specifically induces an S phase arrest and apoptosis in these cells.

Example 29

Demonstration of a Role for p73 in Apoptosis

The p53 transcription factor and tumor suppression protein was specifically implicated in the apoptosis following telomere loop disruption [Karlseder, J., et al., (1999), *Science* 283, 1321–1325]. However, although a role for p53 in apoptosis of murine embryonic fibroblasts after telomere loop disruption was demonstrated experimentally, the implied role for p53 in apoptosis of cells with presumptively compromised p53 in the same studies was not addressed [Karlseder, J., et al., (1999), *Science* 283, 1321–1325]. Because the p53 homolog p73 has also been shown to mediate apoptosis in several cell types [Lissy, N. A., et al., (2000), *Nature* 407: 642–644, Irwin, M., et al., (1997), *Nature* 407: 645–648], and because the telomere homolog DNA induced both proteins, experiments were designed to explore the contribution of this protein to oligonucleotide-induced cell death.

Because HTLV-1 infection has been shown to impair the p73 pathway [Lemasson, I. and Nyborg, J. K. (2001, *J Biol Chem* 276, 15720–15727, Kaida, A., et al., (2000), *Oncogene* 19, 827–830] as well as that of p53 [Akagi, T., et al., (1997), *FEBS Lett* 406, 263–266], a human melanoma line MM-AN known to express wild type p53 was selected for study. Matched cultures of human melanoma cell line MN-AN (obtained from H. R. Beyers, Boston University) were grown in DMEM with 5% FBS and treated with 40 µM 11mer-1, 11mer-2 or diluent alone for 24–48 hours and harvested at intervals for FACS analysis and western blotting.

Like the Jurkat cells, the MM-AN cells first entered an S-phase arrest, and by 72 hours a substantial portion of the cells were undergoing apoptosis, as indicated by their sub-$G_0/G_1$ DNA content. Proteins were analyzed by denaturing polyacrylamide gel electrophoresis (SDS-PAGE), using 10% polyacrylamide, and western blot analysis was done with an E2F1-specific monoclonal antibody (KH95 Santa Cruz Biotechnology, Santa Cruz, Calif.), and p73 analyzed using a polyclonal antibody (AB-4 from Oncogene Research Products, San Diego, Calif.). Western blot analysis revealed the same pattern of induction for E2F1 and p73 as observed for Jurkat cells, consistent with a causal role for these proteins in the observed apoptosis. In order to determine the contribution of p73 to cell death, MM-AN melanoma cells were stably transfected with a dominant negative p73 (p73DN) (Irwin et al., *Nature* 402:645–648) construct or empty vector as a control (p73$^{DN}$-containing vector a gift from Dr. William Kaelin, Dana Farber Institute, Boston) and paired cultures were supplemented with 40 µM 11mer-1 or diluent alone, then harvested at 72 hours for FACS analysis. Cells expressing p73$^{DN}$ underwent apoptosis at half the rate of control cells, confirming a substantial, but not exclusive role for the p73 protein in the process. Furthermore, by western blot, the differentiation markers Mart-1, tyrosinase, TRP-1 and gp-100 were upregulated 48–72 hours after T-oligo treatment of MM-AN melanoma cells. The above-mentioned differentiation markers are expressed in normal human melanocytes. It appears that the loss of expression of these antigens is a mechanism that a subset of human melanomas uses to escape immunosurveillance defenses. Several peptides from these antigens are targets of tumor infiltrating cytotoxic lymphocytes. Encouraging results have been obtained in vivo with different vaccination strategies using antigenic peptides from the above antigens.

Example 30

Effect of the T-oligo on Tumorigenicity of MM-AN Cells in SCID Mice

To study the effect of T-oligo on the tumorigenicity of MM-AN cells, cells were grown in DMEM with 5% fetal bovine serum (FBS) and treated with 40 µM of T-oligo, complement, or diluent alone for 48 hours. The cells were then harvested with trypsin/EDTA and the percent viability determined by trypan blue exclusion. All cell populations at the time of injection had a viability of greater than 90%. The tumorigenicity of these melanoma cells was determined by injecting $1 \times 10^6$ viable cells in balanced salt solution subcutaneously over the right scapular region of SCID mice (3 groups of 5 mice) to produce tumors. The animals were sacrificed by $CO_2$ inhalation 18 days after treatment and the tumor size evaluated with calipers. Tumors were processed for hematoxylin and eosin staining and the melanocytic origin of the tumors was confirmed by immunohistochemical staining of the lesion using HMB-45 monoclonal antibody, which recognizes gp-100, a conventional marker for human melanoma.

Figure 28:
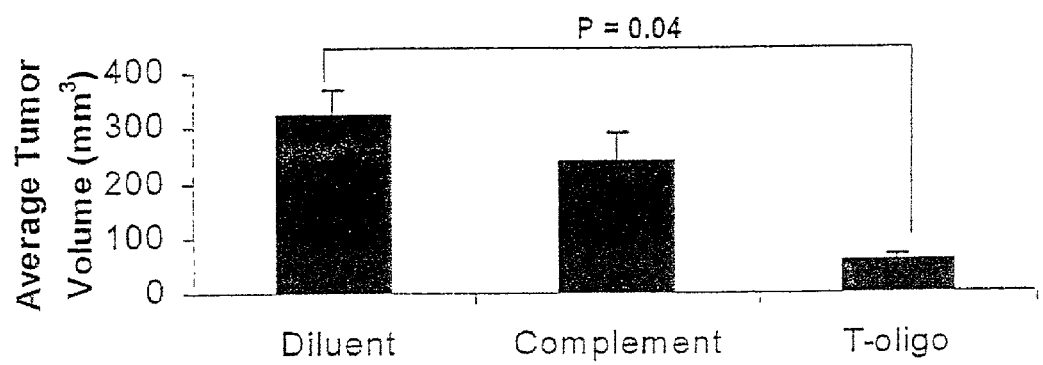
FIG. 28 is a bar graph depicting the average volume of primary tumors that resulted in SCID (severe combined immunodeficiency) mice injected with MM-AN cells pre-treated with diluent, "complement" oligonucleotide with sequence pCTAACCCTAAC (SEQ ID NO:9), or "T-oligo" with sequence pGTTAGGGTTAG (SEQ ID NO:5).

Tumors were palpable at the site injected with cells pretreated with diluent by day 10 and day 12 in the other groups. On day 18, animals were sacrificed and all tumors removed and measured. Mean tumor volume in the diluent-treated group was 322±45 mm$^3$ vs. 56±13 mm$^3$ in the T-oligo treated group (p=0.04). The animals treated with the control oligonucleotide had a tumor volume of 238±50 mm$^3$, not statistically less than the diluent control (FIG. 28). Hematoxylin and eosin staining revealed large tumors present within the subcutis composed of large epitheloid cells with abundant pigmented cytoplasm and large irregular nuclei demonstrating hyperchromasia and large nucleoli. The tumors were identified as melanoma by positive immunohistochemical staining with HMB-45, confirming their melanocytic origin.

To study the effect of T-oligo on the metastatic potential of melanoma cells, cultures of MM-AN cells were treated for 48 hours with T-oligo, complement or diluent alone and harvested as described above. $1 \times 10^6$ cells in balanced salt solution were injected into the lateral tail vein of 5-week old SCID mice (3 groups of 5 mice). After 40 days, mice were sacrificed by $CO_2$ inhalation, an autopsy performed and organs examined macroscopically for visible metastatic lesions.

Figure 29:
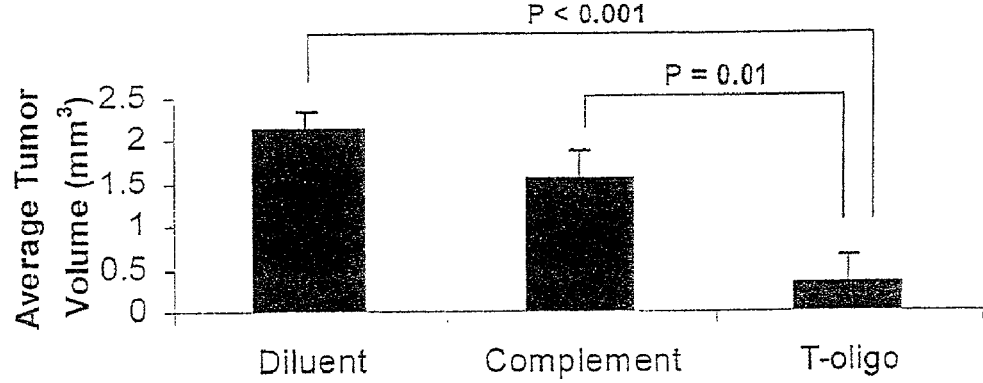
FIG. 29 is a bar graph depicting the average volume of metastatic tumors that resulted in SCID mice injected with MM-AN cells pre-treated with diluent, "complement" oligonucleotide, or "T-oligo." See Example 30.
Figure 31C:
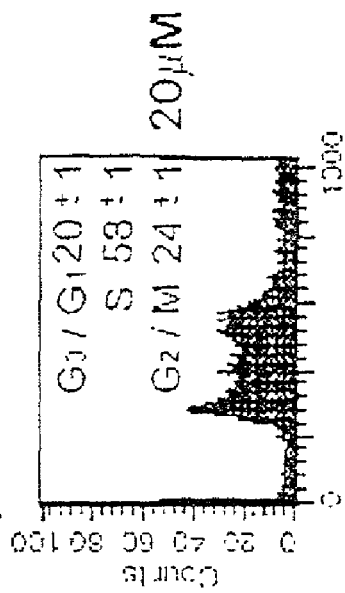
FIGS. 31A–31E are profiles of fluorescence intensity as determined by fluorescence activated cell sorting, for the following additions to Jurkat cells.
Figure 31E:
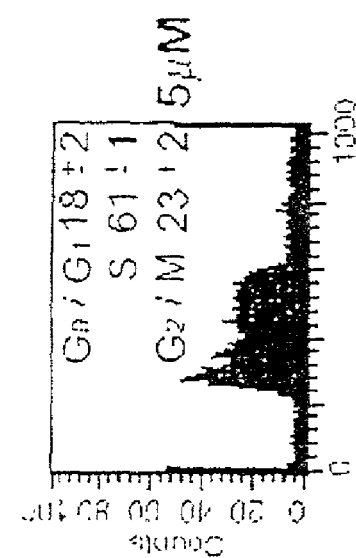
Figure 31B:
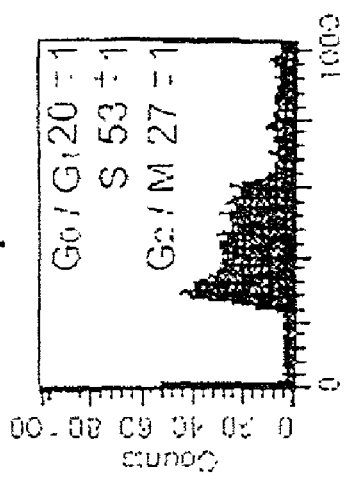
Figure 31D:
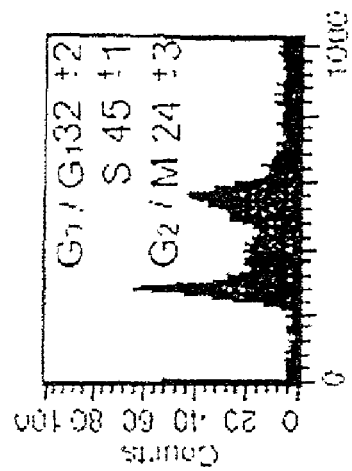
Figure 31A:
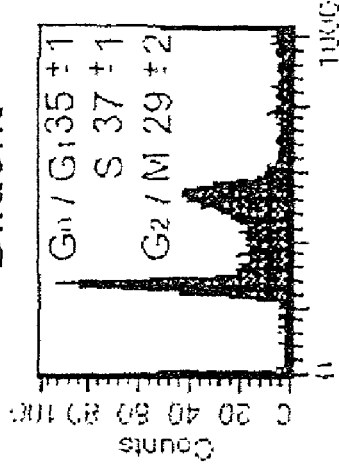

All five animals treated with diluent alone or control oligonucleotide developed multiple metastases in comparison to one of five animals in the T-oligo-treated group. Metastases were seen in the adrenal gland, bone, brain, brown fat, kidney, liver, lung, pancreas and additional sites of the control animals. The average number of visible tumors per animal was 0.8 in the T-oligo pretreated group compared to 15.8 (p=0.003) and 9.6 (p=0.05) in the diluent and control oligo pretreated groups, respectively. The average volume of the macroscopic metastastic tumors was also found to be significantly reduced in the T-oligo treated animals by about 85% and 80% compared to the diluent treated and complement treated animals, respectively (FIG. 29).

TABLE 2

Effect of T-oligo on Macroscopic Metastasis

| Site | Animals with tumors: Diluent | Total tumors: Diluent | Animals with tumors: Control oligo | Total tumors: Control oligo | Animals with tumors: T-oligo | Total: T-oligo |
|---|---|---|---|---|---|---|
| Adrenal | 1/5 | 3 | 2/5 | 3 | 1/5 | 2 |
| Bone | 4/5 | 10 | 1/5 | 3 | 0/5 | 0 |
| Brain | 3/5 | 8 | 3/5 | 3 | 1/5 | 2 |
| Brown fat | 5/5 | 21 | 3/5 | 8 | 0/5 | 0 |
| Kidney | 3/5 | 13 | 4/5 | 7 | 0/5 | 0 |

TABLE 2-continued

Effect of T-oligo on Macroscopic Metastasis

| Site | Animals with tumors: Diluent | Total tumors: Diluent | Animals with tumors: Control oligo | Total tumors: Control oligo | Animals with tumors: T-oligo | Total: T-oligo |
|---|---|---|---|---|---|---|
| Liver | 1/5 | 9 | 2/5 | 4 | 0/5 | 0 |
| Lung | 1/5 | 3 | 3/5 | 6 | 0/5 | 0 |
| Pancreas | 3/5 | 4 | 4/5 | 7 | 0/5 | 0 |
| Miscellaneous | 3/5 | 8 | 1/5 | 7 | 0/5 | 0 |
| Total Tumor Load (5 animals) | | 79 | | 48 | | 4 |
| Average tumors per animal | | 15.8 | | 9.6 | | 0.8 |
| METASTASIS FREE | 0/5 | | 0/5 | | 4/5 | |

Example 31

Activity Depends on Homology to Telomere Overhang Sequence

To further confirm the specificity of these responses to the telomere overhang sequence, three variations were tested. Like 11 mer-1, its permutation pGGGTTAGGGTT (SEQ ID NO:13) is an exact homolog of the overhang and hence, predicted to be equally active. A second oligonucleotide, pTAGATGTGGTG (SEQ ID NO:14) is equally as G-rich (5 of 11 bases) as 11mer-1 and has 55% homology to the overhang, similar to the 9-mer oligonucleotide, pGAGTAT-GAG (SEQ ID NO:1), recently shown to induce p53 and pigmentation, and to enhance DNA repair capacity (see Example 12). A third oligonucleotide, pCGGGCTTATTG (SEQ ID NO:15), also has 55% homology to the overhang, but differs from the other oligonucleotides in that it contains 18% cytosine bases that are not present in the overhang sequence. These oligonucleotides were added individually to cultures of Jurkat cells at a final concentration of 10 μM. Cells were collected after 72 hours and processed for FACS analysis. Each experimental condition was done in triplicate. The data shown in FIGS. 30A–30H are from one representative experiment of two. By 72 hours, 2% of the diluent-treated cells and cells treated with cytosine-containing oligonucleotide were apoptotic by FACS analysis. However, 13% of the homolog-treated and 10% of the partial homolog-treated cells were apoptotic. After 96 hours, 28% of the homolog-treated cells were apoptotic, compared to 16% of the partial homolog-treated cells, and 2–4% of cells in cultures treated with the cytosine-containing oligonucleotide or diluent alone. In separate paired cultures, the two complete telomere overhang homologs [pGTTAGGGTTAG (SEQ ID NO:5) and pGGGTTAGGGTT (SEQ ID NO:13)] were shown to be equal in activity. The data suggest that oligonucleotide activity is a function of telomere homology rather than, for example, G content primarily. Furthermore, the presence of cytosine in the oligonucleotide greatly diminishes its activity independent of degree homology. Although pTAGATGTGGTG (SEQ ID NO:14) and pCGGGCTTATTG (SEQ ID NO:15) share comparable homology with the telomere overhang, the latter oligonucleotide failed to induce apoptosis and only induced a moderate S-phase arrest. This is consistent with work described in Example 12 comparing 2–20 base oligonucleotides in their ability to induce other UV-mimetic DNA damage responses.

To determine if pTT, representing 33% of the 6 base telomere tandem repeat sequence, induces an S-phase arrest in Jurkat cells in the same way as the full telomere repeat sequence, we compared the effects of pTT and 11mer-1 on Jurkat cells. In order to determine relative efficacy of pTT and 11mer-1, cultures of Jurkat cells were treated with diluent, 20 μM or 5 μM pTT or 11 mer-1 for 72 hours and collected for FACS analysis. Each experimental condition was performed in triplicate. The percentage of cells in each phase of the cell cycle, indicated as an average and standard deviation, was determined from the triplicate results. One representative experiment of three is shown in FIGS. 31A–31E. At a concentration of 20 μM, the cell cycle profiles of pTT- and 11mer-1-treated Jurkat cells were nearly identical, with 53±1% and 58±1%, respectively, of the treated cells in the S-phase at 72 hours. However, at 5 μM, 61% of the 11mer-1 treated cells had accumulated in the S-phase within 72 hours, compared to 45% of the pTT-treated cells and 36% of the diluent-treated cells. Although Jurkat cells treated with a higher 11mer-1 dose (40 μM, FIG. 19F) also showed a comparable percentage of cells in S phase at 72 hours (38%), these cultures additionally contained 13% apoptotic ($<G_0$) cells. No apoptosis was detected in Jurkat cultures treated with 20 μM pTT even at 96 hours. Thus, pTT and the telomere overhang homolog have similar effects on the cell cycle in Jurkat cells, although higher concentrations of the incomplete sequence are needed. These data, together with those in FIG. 30, as well as other data for other oligonucleotides 2–20 bases in length (Example 12) further suggest that the ability of these oligonucleotides to induce DNA damage responses is directly related to their degree of homology to the telomere repeat sequence, although many sequences with only partial homology also have useful effects.

Example 32

Induction of S-phase Arrest, E2F1, and p53 Protein Levels, and Phosphorylation of p53 in Normal Human Fibroblasts Preconfluent cultures of normal neonatal human fibroblasts were treated with the oligonucleotides (40 μM) or diluent alone and collected 24 hours later for FACS analysis (FIGS. 32A–32D) or western blot. The averages and standard deviations presented in FIGS. 32A–32D were determined from triplicate samples. One representative experiment of three is presented. Normal neonatal human fibroblasts respond within 24 hours to the telomere overhang homolog oligonucleotide, 11mer-1, by activation of an S-phase checkpoint, but no apoptotic cells were detected up to 72 hours after treatment. Control 11-base oligonucleotides complementary (11mer-2) or unrelated (11mer-3) to the telomere overhang had no effect on the cells. The selective effect of the telomere homolog oligonucleotide cannot be attributed to selective uptake, as comparable uptake has been shown among same length oligonucleotides regardless of sequence.

Activation of p53 as indicated by phosphorylation on serine-15 was determined by western blot analysis, using the phospho-p53 (ser-15) specific antibody 16G8. The blot was then stripped and re-probed with the pantropic p53 DO-1. Lanes of the gel contained protein from fibroblasts treated with diluent alone, 11mer-1 or 11mer-2, collected at 24, 48 or 72 hours. As a positive control, fibroblasts from another donor were either sham- or X-irradiated (10 Gy) and collected after 3 hours. Densitometric analysis showed a 170–250% increase in E2F1 in 11mer-1 treated fibroblasts compared to diluent or 11mer-2 treated controls at 24 hours. p53 increased by 60–300% at 48 hours and 240–380% at 72 hours after 11mer-1 treatment compared to diluent or 11mer-2 treated controls. All values were normalized to β-actin and are based on two independent experiments. Western analysis of the treated fibroblasts showed that p53 and E2F1 are selectively induced by the telomere overhang homolog.

An increase in E2F1 was seen as early as 4 hours after addition of the 11-mer-1, peaked 12–24 hours after, and subsequently returned to control levels. The E2F1 transcription factor is known to cooperate with p53 in induction of apoptosis (Kowalik, T. F., et al., 1995, *J Virol* 69: 2491–2500, Kowalik, T. F., et al., 1998, *Cell Growth Differentiation* 9: 113–118) and to induce a senescent phenotype in human fibroblasts in a p53-dependent manner (Dimri, G. P., et al., 2000, *Mol Cell Biol* 20: 273–285). Furthermore, E2F1 is induced by DNA damage from IR in a manner dependent on the ATM kinase (Lin, W. C., et al, 2001, *Genes and Dev.* 15: 1833–1844). To determine whether 11mer-1, like pTT (Eller, M. S., et al., 1997, *Proc Natl Acad Sci USA* 94: 12627–12632, Maeda, T., et al., 1999, *Mutat Res* 433: 137–145), activates as well as induces p53, we also examined p53 phosphorylation, a marker of transcriptional activation of p53 after various forms of DNA damage (Lambert, P., et al., 1998, *J Biol Chem* 273: 33048–33053, Dumaz, N. and D. W. Meek. 1999. *EMBO J* 18: 7002–7010, Tibbetts, R. S., et al., 1999, *Genes Dev* 13: 152–157, Caspari, T., 2000, *Curr Biol* 10: 315–317, Unger, T., et al., 1999, *Oncogene* 18: 3205–3212). There was a striking and selective increase in p53 protein phosphorylated at serine 15 in response to the 11mer, first detected at 4 hours and sustained through at least 48 hours.

Example 33 p53 Phosphorylation and E2F1 Induction Are Dependent on ATM

Because the serine 15 site on p53 is known to be phosphorylated in an ATM-dependent manner after exposure to ionizing radiation (IR), we wished to examine the role of ATM in E2F1 induction and p53 serine 15 phosphorylation in response to the 11 mer-1. Fibroblasts from a patient with ataxia telangiectasia (AT) known to lack functional ATM protein, and age-matched normal control fibroblasts (N) were treated with either diluent, 40 μM 11mer-1, sham irradiation or IR (10 Gy). Cells were collected 3 hours (sham or IR) or 48 hours (diluent, 11mer-1) for western blot analysis to detect serine 15-phosphorylated p53 and total p53. In normal fibroblasts, the 11mer-1 induced a 10–15 fold increase in the level p53 phosphorylation on serine 15 compared to diluent-treated controls. In contrast, treatment of AT fibroblasts with the 11mer-1 resulted in less than a 50% increase. The 11 mer-1 minimally induced the level of total p53 in these normal fibroblasts from a young adult donor, in contrast to the induction of p53 in newborn fibroblasts, consistent with the previously described reduced response to UV-induced DNA damage for adult versus newborn cells. As expected, AT fibroblasts showed only minimal phosphorylation of p53 serine 15 in response to IR. The 11mer-1 also induced E2F1 levels in normal control fibroblasts, but not in AT fibroblasts. These data demonstrate a requirement for the ATM kinase in these responses to telomere overhang DNA and are consistent with ATM-dependent p53 induction by TRF2$^{DN}$ (Karlseder, J. et al., 1999, *Science* 283: 1321–1325).

Example 34

Cell Cycle Arrest Is Not Dependent On p53

In order to determine whether these oligonucleotides similarly affect other human cell types and to investigate the role of p53, we treated a squamous cell carcinoma line (SCC12F) (Rheinwald, J. G., et al., 1983, *Human carcinogenesis*. pp. 86–96. Academic Press (New York)) that overexpresses a presumptively mutated p53 (Eller, M. S. and B. A. Gilchrest. 2000, *Pigment Cell Res.* 13: 94–97) and a p53-null osteosarcoma cell line (Saos-2) (Wang, L. H., et al., 1998, *Anticancer Res* 18: 321–325) with either diluent alone, 11mer-1, 11mer-2 or 11mer-3. Cultures were analyzed by FACS after 48 hours (FIGS. 33A–33H). As with the Jurkat cells and normal fibroblasts, the telomere overhang homolog selectively induced an S-phase arrest in both of these cell types within 48 hours. Although the percentage of cells in the S-phase in 11mer-1-treated SCC12F and Saos-2 cells was virtually identical (53±6% and 52±1%, respectively), the $G_0/G_1$ and $G_2/M$ content of the two cell types were somewhat different. This may reflect differential uptake of the oligonucleotide leading to dose-dependent differences, and/or different pathways acting in these cells to control the cell cycle. No apoptotic response to the oligonucleotides was detected in either cell type within 72 hours. These data demonstrate that the 11mer-1 affects cells of both epithelial and mesenchymal origin and that the S-phase arrest in response to 11mer-1 is not dependent on p53. However, because many cell types with wild type p53 are relatively resistant to apoptosis after DNA damage (Sionov, R. V. and Y. Haupt. 1999. *Oncogene* 18: 6145–6157), the data do not address the role of p53 in the apoptotic response to 11mer-1, which notably occurs in Jurkat cells that express a presumptively compromised p53 (Akagi, T., et al., 1997, *FEBS* 406: 263–266).

Example 35

Cells Lacking Functional p95/Nbs1 Do Not Activate the S-phase Checkpoint In Response to the Telomere Overhang Homolog Because of the demonstrated role of p95/Nbs1 in the S-phase arrest in response to IR and its known association with telomeric DNA, we next examined its role in the S-phase arrest seen in response to the telomere overhang homolog. Fibroblasts were obtained from an NBS (Nijmegen breakage syndrome) patient, in which p95/Nbs1 was below the level of detection. Preconfluent cultures or normal (control) fibroblasts and NBS fibroblasts were treated with 40 µM of the oligonucleotides and collected after 48 hours for FACS analysis (FIGS. 34A–34H). The averages and standard deviations were calculated from triplicate cultures of each condition. FACS profiles from one representative experiment of three are shown. As expected, 11 mer-1-treated normal cells exhibit an S phase growth arrest within 24 hours, while the same cells treated with diluent alone, 11mer-2 or 11mer-3 are unaffected.

Unrelated oligonucleotide-treated and diluent-treated NBS cells display an FACS profile similar to that of the normal cells arrested in the S phase and, compared to the diluent-treated NBS cells, their proliferation is minimally affected by the 11mer-1. These data suggest that p95/Nbs1 has a previously unidentified role in normal progression of the S phase and that DNA synthesis is protracted in the absence of functional p95/Nbs1. Also of interest, the 8% increase in the number of S-phase cells in 11mer-1-treated NBS cultures compared to diluent-treated cells, although not statistically significant (p<0.08), suggests that factors other than p95/Nbs1 may contribute to the arrest following DNA damage or 11mer-1 treatment. For example, unscheduled E2F1 activity during the S-phase has been shown to lead to activation of an S-phase checkpoint (Krek, W., et al., 1995, *Cell* 83: 1149–1158).

Phosphorylation of p95/Nbs1 by ATM, causally related to activation of the S-phase checkpoint after DNA damage, can be detected by PAGE as a subtle slowing of the protein migration in the gel (Lim, D. S., et al., 2000, *Nature* 404: 613–617, Zhao, S., et al., 2000, *Nature* 405:473–477, Wu, X., et al., 2000, *Nature* 405: 477–482). Western blot analysis detects such a shift in p95/Nbs1 migration in protein harvested from Jurkat cells 48, 72 and 96 hours after addition of the 11mer-1 but not 11mer-2 or 11mer-3. This change in apparent molecular weight of p95/Nbs1, presumably from covalent modification of the protein, coincides with the S-phase arrest as determined by FACS analysis. This shift in p95/Nbs1 migration also occurs in these cells after IR, as previously reported and ascribed to protein phosphorylation (Lim, D. S., et al., 2000, *Nature* 404: 613–617, Zhao, S., et al., 2000, *Nature* 405: 473–477, Wu, X., et al., 2000, *Nature* 405: 477–482). SCC12F cells respond identically to addition of the 11 mer-1, again in a time frame in agreement with their activation of the S-phase checkpoint. The shift in SCC12F cells is more apparent with immunoprecipitated p95/Nbs1 from 1 1mer-1-treated and irradiated cells and is eliminated by treatment of the immunoprecipitated protein with a serine/threonine phosphatase as was reported for p95/Nbs1 phosphorylated in response to IR (Lim, D. S., et al., 2000, *Nature* 404: 613–617). Probing a western blot of proteins from diluent- and oligonucleotide-treated fibroblasts with a phospho-p95/Nbs1-specific antibody further demonstrates that phosphorylation of p95/Nbs1 is induced by the telomere overhang homolog oligonucleotide 11mer-1.

Example 36

Telomere Disruption by TRF2$^{DN}$ Leads to Modification of p95/Nbs1

Karlseder et al. (Karlseder, J., 1999, *Science* 283: 1321–1325) previously demonstrated that ectopic expression of TRF2$^{DN}$, which disrupts the telomere loop and exposes the 3' overhang, induces an increase in p53 and apoptosis in certain cell types. In order to see if p95/Nbs1 modification is also induced by telomere disruption, neonatal human fibroblasts were transiently transfected with the TRF2$^{DN}$ expression vector or a (control) vector without the TRF$^{DN}$ insert. Cells were collected up to 40 hours after transfection and p95/Nbs1 was analyzed by Western blot using a phospho-p95-specific antibody. By 24 hours post transfection, a distinct shift in p95/Nbs1 mobility is detected, similar to that seen after exposure to IR (10 Gy). This shift to a higher molecular weight is still apparent after 40 hours. These data demonstrate that both telomere disruption and treatment with a homolog of the telomere 3' overhang induce modification of p95/Nbs1 and hence, support our hypothesis that exposure of the 3' overhang is the primary signal for the DNA damage responses observed after various manipulations of the telomere.

Example 37

Telomere Overhang Oligonucleotide Does Not Decrease Telomere Length or Alter the 3' Overhang To eliminate the possibility that the 11mer-1 oligonucleotide acts indirectly by disrupting the telomere loop structure, leading to critical telomere shortening and/or degradation of the 3' overhang as reported after TRF2$^{DN}$ transfection (Karlseder, J., 1999, *Science* 283: 1321–1325), we analyzed mean telomere length after treatment of normal human fibroblasts with the oligonucleotides for 5 days, longer than necessary to induce p53 and the S phase checkpoint. Normal human fibroblasts were treated with either diluent alone, 40 µM 11mer-1, 11mer-2 or 11mer-3 for 5 days. The fibroblasts were harvested and the genomic DNA was isolated. Telomere length analysis was performed for diluent-treated cells, 11 mer-1-treated cells, 11mer-2-treated cells, 11mer-3-treated cells, and late passage fibroblasts (population doubling >50), and compared with high molecular weight and low molecular weight telomere markers. The MTL values (in kilobases) for each experimental condition, calculated as described by Harley, et al. (Harley, C. B. et al., *Nature* 345:458–460, 1990), were as follows: 10.59 (diluent), 12.25 (11mer-1), 10.45 (11mer-2), 10.22 (11mer-3), 8.86 (senescent), 10.19 (high molecular weight standard), 4.04 (low molecular weight standard). The 3' overhang assay was carried out on newborn fibroblasts treated for 3, 5, or 7 days with 40 µM 11mer-1.

None of the oligonucleotides reduced mean telomere length (MTL). Indeed, 11mer-1-treated cells showed a modest increase in MTL of approximately 20% during the 5-day experiment. Furthermore, treatment of fibroblasts with the 11mer-1 oligonucleotide for up to 7 days did not result in degradation of the telomere 3' overhang as was observed following telomere disruption by TRF2$^{DN}$ (Karlseder, J., 1999, *Science* 283:1321–1325). These data strongly suggest that the 11mer-1 does not affect telomere integrity, but likely mimics the signal created by this process. Similarly, the 11mer-1 effects cannot be attributed to inhibition of telomerase, for example by acting as a pseudosubstrate and hence preventing telomere elongation, because normal human fibroblasts, cells in which the effects are readily observed, do not express the catalytic subunit TERT (Greider, C. W. 1996, *Annu Rev Biochem* 65: 337–365). Furthermore, telomere erosion due to telomerase inhibition would be expected to exert effects only after an extended period of time, more than 50 population doublings in previous reports (Naka, K., et al., 1999, *Biochem Biophys Res Comm* 255: 753–758, Marusic, L., et al., 1997, *Mol Cell Biol* 17: 6394–6401, Hande, M. P., et al., 1999, *J Cell Bio* 144: 589–601), far greater than the 24–48 hours reported here, and is in any case not observed.

Example 38

Oligonucleotide Treatment of in Situ Melanoma in SCID Mice by Various Delivery Methods (Hypothetical)

MM-AN cells will be grown in DMEM with 5% FBS, the cells will then be harvested with trypsin/EDTA, and the percent viability will be determined by trypan blue exclusion. Only cell populations with 90% or greater viability will be used for the experiments. The tumorigenicity of these melanoma cells will be determined by subcutaneously injecting $1 \times 10^6$ viable cells in balanced salt solution into the hind limb of SCID mice to produce subcutaneous tumors. For these studies, 3 groups of mice (5 mice/group) will be used. Group 1 will be given IP injections of 200 µg T-oligo five times weekly, starting 24 hours after injection of cells group 2 will be given IP injections with 200 µg of the control oligonucleotide five times weekly and group 3 will be injected with diluent. Oligonucleotides delivered IP have been found to be effective in reducing the size of subcutaneous melanoma in mice (Massod, R., et al., *Blood* 96:1904–1913, 2001). The size of the tumors will be monitored by twice weekly examination of the mice and measurement of the tumors with calipers. The mice will be killed 4 weeks after injection and the tumors will be processed for hematoxylin and eosin staining.

MM-AN melanoma cells will be treated and harvested as described above. Instead of delivering the oligonucleotide IP it will be delivered by an Alzet pump. 500 µg/per day of T-oligo or control oligo or diluent will be infused for 4 weeks. The size of the tumor will be evaluated as described above. Alzet pumps have been found effective in treating subcutaneous melanoma tumors in mice (Hijiya, N., et al. *Proc. Natl. Acad. Sci. USA* 91:4499–4503, 1994).

MM-AN melanoma cells will be treated and harvested as described above. Group 1 will be given IV injections of 200 µg T-oligo three times weekly, group 2 will be given IV injections with 200 µg of control oligonucleotide three times weekly, and group 3 will be injected with diluent. Mice will be killed 4 weeks after injection and the size of the tumors will be evaluated as described above.

Example 39

Oligonucleotide Effect on Melanoma Metastasis and Tumorigenicity (Hypothetical)

The pilot experiment protocol which results in maximum tumor regression will be selected. MM-AN melanoma cells will be treated and harvested as described above. $1 \times 10^6$ cells in balanced salt solution will be injected into the lateral tail vein of 4 week old SCID mice. There will be 3 groups of 25 mice for each of the above treatment groups. Group 1 will be injected with T-oligo; group 2 will be injected with the control oligonucleotide and group 3 will be injected with diluent. All treatments will begin 24 hours after injecting the cells. After 6 weeks, the mice will be killed by $CO_2$ inhalation, an autopsy will be performed and organs will be examined macroscopically for visible lesions. Particular emphasis will be given to liver, pancreas and brain because these organs have been shown to be the primary sites of metastasis of MM-AN cells. For examination and sectioning, organs will be rinsed in PBS and fixed in 10% formalin for 48 hours. Organs will be examined under a dissecting microscope and the number of tumor nodules counted. The histological characteristics of tumors will be examined with hematoxylin and eosin-stained sections of tissue fixed in formalin and embedded in paraffin.

MM-AN melanoma cells will be treated and harvested as described above. The pilot experiment protocol which resulted in maximum tumor regression will be selected. The tumorigenicity of these melanoma cells will be determined by intradermally injecting $1 \times 10^6$ viable cells in balanced salt solution into the hind limb region of SCID mice to produce subcutaneous tumors. The size of the tumor will be monitored by twice weekly examination of the mice and measurement of tumors with calipers. The mice will be killed 4 weeks after injection and the tumors will be removed, measured and processed for hematoxylin and eosin staining. Three groups of mice will be used. Group 1 will be treated with T-oligo, group 2 will be treated with control oligonucleotide, and group 3 will be treated with diluent. Apoptosis will be determined in tumors by TUNEL in the groups of mice discussed above. The expression of differentiation markers gp-100, TRP-1 and Mart-1 will also be studied in tumors from the three groups of mice studied above.

Example 40

Telomere Homolog Oligonucleotides Less Than 6 Nucleotides in Length Inhibit Proliferation of a Human Osteosarcoma Cell Line Human Saos-2 cells were plated in DME with 10% fetal bovine serum in p35 culture dishes, and dosed with 40 µM 5mer (TTAGG), 3mer (TTA) 11mer-1 (GTTAGGGTTAG; SEQ ID NO:5) or diluent alone as control, and cultured for an additional 36 hours after addition of oligonucleotides or diluent. Cells were then collected by trypsinization and counted by Coulter Counter. The FIG. 36 graph represents averages of cell population doublings after additions, with standard error of mean, for duplicate cultures.

Equivalents

While this invention has been particularly shown and described with references to preferred embodiments thereof, it will be understood by those skilled in the art that various changes in form and details may be made therein without departing from the scope of the invention encompassed by the appended claims.

What is claimed is:

1. A composition comprising an oligonucleotide and a physiologically acceptable carrier, wherein the oligonucleotide is pGAGTATGAG (SEQ ID NO:1).

2. A method of preventing or reducing DNA damage in cells of a mammal, wherein said DNA damage is caused by radiation or DNA-damaging chemicals, comprising contacting said cells in vitro with a composition comprising at least one oligonucleotide, wherein the oligonucleotide comprises SEQ ID NO: 1.

3. The method of claim 2, wherein the cells are epithelial cells.

4. The method of claim 2, wherein said oligonucleotide is single-stranded.

5. The method of claim 2, wherein the oligonucleotide comprises a 5' phosphate.

6. The method of claim 2, wherein the composition comprises the oligonucleotide at a concentration of about 1 µM to about 500 µM.

7. The method of claim 2, wherein the composition comprises a physiologically acceptable carrier.

8. A composition comprising an oligonucleotide and a physiologically acceptable carrier, wherein the oligionucliotide comprises SEQ ID NO: 1.

9. The composition of claim 8, wherein the oligonucleotide comprises a 5' phosphate.

10. The composition of claim 8 which comprises more than one oligonucleotide.

* * * * *